United States Patent
Roth et al.

(10) Patent No.: US 7,030,196 B2
(45) Date of Patent: Apr. 18, 2006

(54) PROCESS FOR REDUCING THE MOLECULAR WEIGHT OF POLYPROPYLENE

(75) Inventors: Michael Roth, Lautertal (DE); Rudolf Pfaendner, Rimbach (DE); Peter Nesvadba, Marly (CH); Marie-Odile Zink, Steinbach (FR)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/275,495

(22) PCT Filed: May 14, 2001

(86) PCT No.: PCT/EP01/05447

§ 371 (c)(1),
(2), (4) Date: Nov. 5, 2002

(87) PCT Pub. No.: WO01/90113

PCT Pub. Date: Nov. 29, 2001

(65) Prior Publication Data

US 2003/0216494 A1    Nov. 20, 2003

(30) Foreign Application Priority Data

May 19, 2000    (EP) .................................. 00810443

(51) Int. Cl.
*C08C 19/22* (2006.01)
*C08F 8/32* (2006.01)

(52) U.S. Cl. ...................... 525/375; 525/194; 525/240; 525/331.7; 525/333.7

(58) Field of Classification Search ............... 524/99, 524/100, 102, 414, 415, 417, 427, 432, 433, 524/442; 526/328.5; 525/194, 240, 331.7, 525/333.7, 375

See application file for complete search history.

(56) References Cited

U.S. PATENT DOCUMENTS

| | | | |
|---|---|---|---|
| 3,857,907 A | | 12/1974 | Martin et al. ............... 260/982 |
| 4,680,325 A | * | 7/1987 | Dunski et al. .............. 524/101 |
| 5,004,770 A | | 4/1991 | Cortolano et al. ............ 524/99 |
| 5,910,549 A | * | 6/1999 | Matyjaszewski et al. ... 526/217 |
| 5,948,836 A | * | 9/1999 | Bonora ........................ 524/99 |
| 6,479,608 B1 | | 11/2002 | Nesvadba et al. ....... 526/328.5 |
| 6,583,245 B1 | * | 6/2003 | Steinmann et al. ...... 526/218.1 |
| 6,664,353 B1 | * | 12/2003 | Nesvadba et al. .......... 526/217 |
| 6,797,375 B1 | * | 9/2004 | Pearson et al. ............. 428/343 |

FOREIGN PATENT DOCUMENTS

| | | | |
|---|---|---|---|
| DE | 2013666 | | 10/1970 |
| DE | 19949352 | | 4/2000 |
| EP | 0135280 | | 3/1985 |
| GB | 2 300 192 | * | 10/1996 |
| WO | 85/04664 | | 10/1985 |
| WO | 97/49737 | | 12/1997 |
| WO | 98/13392 | | 4/1998 |
| WO | 98/31739 | | 7/1998 |
| WO | 99/00427 | | 1/1999 |
| WO | 00/07981 | | 2/2000 |
| WO | 200039209 | * | 6/2000 |
| WO | 00/63260 | | 10/2000 |
| WO | 01/20078 | | 3/2001 |

* cited by examiner

*Primary Examiner*—Helen L. Pezzuto
(74) *Attorney, Agent, or Firm*—Joseph C. Suhadolnik

(57) ABSTRACT

The invention relates to the use of known hydroxylamine esters selected from the group consisting of HALS (sterically hindered amine) compounds and novel hydroxylamine esters for the controlled degradation of polypropylene.

15 Claims, No Drawings

PROCESS FOR REDUCING THE MOLECULAR WEIGHT OF POLYPROPYLENE

The invention relates to novel hydroxylamine esters and polymerizable compositions comprising these hydroxylamine esters and an ethylenically unsaturated monomer or oligomer. The invention further relates to the use of hydroxylamine esters as polymerization initiators and to the use of hydroxylamine esters for the controlled degradation of polypropylene and for the controlled build-up of the molecular weight or crosslinking of polyethylene.

Free-radical polymerization is among the most important methods of building up a relatively long carbon chain. It is employed in process technology for preparing commercially important polymers such as polystyrene, PVC, polyacrylates, polymethacrylates, PAN and other polymers. For technical details, reference may be made to the still relevant standard work G. Odian, *Principles of Polymerization*, McGraw-Hill New York 1970, and also to H.-G. Elias, *Makromoleküle, 6th Edition, Volume I*, Wiley-VCH, DE-Weinheim 1999, ISBN 3-527-29872-X; K. Hatada, T. Kitayama, O. Vogl, *Macromolecular Design of Polymeric Materials*, Marcel Dekker New York 1997, ISBN 0-8247-9465-6; M. K. Mishra, Y. Yagci, *Handbook of Radical Vinyl Polymerization*, Marcel Dekker New York 1998, ISBN 0-8247-9464-8.

Free-radical polymerizations are started using initiators. Initiators which have become established in process technology are azo compounds, dialkyl peroxides, diacyl peroxides, hydroperoxides, thermolabile C—C-dimers, redox systems and photoinitiators.

Despite their widespread use, these initiators have various disadvantages. Thus, for example, peroxides are extremely readily ignitable and sustain fire. Other classes of substances are potential explosion hazards, so that their use, storage and transport has to involve costly safety precautions.

There is therefore a general need for advantageous initiators useful in process technology which have a satisfactory safety profile for free-radical polymerization processes. EP-A-735 052 describes a process for preparing thermoplastic polymers having a low poly-dispersity, which comprises free-radical polymerizations by addition of customary free-radical initiators in combination with stable free radicals as polymerization regulators to the monomers. WO 98/30601 describes nitroxyl radicals (>N—O.compounds) based on imidazolidinones and derived from alkoxyamines and their use as polymerization initiators. WO 98/44008 likewise describes nitroxyls based on morpholinones, piperazinones and piperazinediones. WO 00/07981 describes open-chain alkoxyamines and their use as polymerization initiators. The published German patent application 199 49 352.9 describes further 5- and 6-membered heterocyclic alkoxyamines which are substituted in one or both α-positions and display steric hindrance owing to the size of these substituents.

Regardless of these proposed possibilities, which are a representative selection of the prior art, for improving the procedures for free-radical polymerizations, there continues to be a need for new polymerization initiators which can be used safely and allow a controlled reaction.

It has surprisingly been found that open-chain and cyclic hydroxylamines of various structures are particularly suitable as polymerization initiators if they are esterified by acyl radicals.

The invention provides compounds a) of the formula:

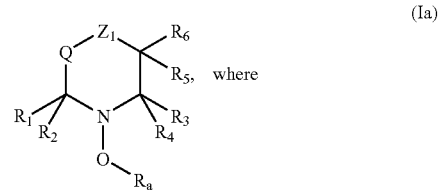

(Ia)

where $R_a$ is an acyl radical selected from the group consisting of —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl and —C(=O)—N($C_1$–$C_6$alkyl)$_2$;

$R_1$–$R_4$ are each $C_1$–$C_6$alkyl;

$R_5$ and $R_6$ are each, independently of one another, hydrogen, $C_1$–$C_6$alkyl or $C_6$–$C_{10}$aryl; or $R_5$ and $R_6$ are together oxygen;

Q is a direct bond or a bivalent radical —($CR_7R_8$)— or —($CR_7R_8$—$CR_9R_{10}$)—, where $R_7$, $R_8$, $R_9$ and $R_{10}$ are each, independently of one another, hydrogen or $C_1$–$C_6$alkyl; and $Z_1$ is oxygen or a bivalent radical —$NR_{11}$—, where $R_{11}$ is hydrogen, $C_1$–$C_6$alkyl, $C_6$–$C_{10}$aryl or the acyl radical $R_a$ having one of the abovementioned meanings; or b) of the formula Ia, where $R_a$ is an acyl radical selected from the group consisting of —P(=O)—$C_1$–$C_{19}$alkyl, —P(=O)$_2$—$C_1$–$C_{19}$alkyl, —P(=O)—$C_6$–$C_{10}$aryl, —P=O(—$C_1$–$C_{19}$alkyl)$_2$, —P=O(—$C_6$–$C_{10}$aryl)$_2$, —P(=O)—O—$C_1$–$C_6$alkyl, —P(=O)—O—$C_6$–$C_{10}$aryl, —P=O(—$C_1$–$C_6$alkyl)$_2$, —P=O(—O—$C_6$–$C_{10}$aryl)$_2$, —P(—O—$C_1$–$C_6$alkyl)$_2$ and —P(—O—$C_6$–$C_{10}$aryl)$_2$;

$R_1$–$R_4$ are each $C_1$–$C_6$alkyl;

$R_5$ and $R_6$ are each, independently of one another, hydrogen, $C_1$–$C_6$alkyl or $C_6$–$C_{10}$aryl; or $R_5$ and $R_6$ are together oxygen;

Q is a direct bond or a bivalent radical —($CR_7R_8$)— or —($CR_7R_8$—$CR_9R_{10}$)—, where $R_7$, $R_8$, $R_9$ and $R_{10}$ are each, independently of one another hydrogen or $C_1$–$C_6$alkyl; and $Z_1$ is oxygen or a bivalent radical —$NR_{11}$— or —($CR_{12}R_{13}$)—, where $R_{11}$ is hydrogen, $C_1$–$C_6$alkyl or $C_6$–$C_{10}$aryl or, independently of one another, one of the radicals $R_{12}$ and $R_{13}$ is hydrogen or $C_1$–$C_6$alkyl and the other is $C_1$–$C_6$alkyl, $C_1$–$C_6$alkoxy, $C_6$–$C_{10}$aryloxy, acyloxy selected from the group consisting of —O—C(=O)—H, —O—C(=O)—$C_1$–$C_{19}$alkyl, —O—C(=O)—$C_1$–$C_{54}$alkenyl, —O—C(=O)—$C_6$–$C_{10}$aryl, —O—C(=O)—$C_1$–$C_{36}$alkenyl-$C_6$–$C_{10}$aryl, —O—C(=O)—O—$C_1$–$C_{19}$alkyl, —O—C(=O)—O—$C_6$–$C_{10}$aryl, —O—C(=O)—NH—$C_1$–$C_6$alkyl, —O—C(=O)—NH—$C_6$–$C_{10}$aryl and —O—C(=O)—N($C_1$–$C_6$alkyl)$_2$, $C_1$–$C_6$alkylamino, di-$C_1$–$C_6$alkylamino, $C_6$–$C_{10}$arylamino, acylamino selected from the group consisting of —NH—C(=O)—H, —NH—C(=O)—$C_1$–$C_{19}$alkyl, —NH—C(=O)—$C_1$–$C_{54}$alkenyl, —NH—C(=O)—C$_6$–C$_{10}$aryl, —NH—C(=O)—C$_1$–C$_{36}$alkenyl-C$_6$–C$_{10}$aryl, —NH—C(=O)—O—C$_1$–C$_{19}$alkyl, —NH—C(=O)—O—C$_6$–C$_{10}$aryl, —NH—C(=O)—NH—C$_1$–C$_6$alkyl, —NH—C(=O)—NH—C$_6$–C$_{10}$aryl and —NH—C(=O)—N(C$_1$–C$_6$alkyl)$_2$, diacylamino selected from the group consisting of —N[—C(=O)—C$_1$–C$_{19}$alkyl]$_2$ and —N[—C(=O)—C$_6$–C$_{10}$aryl]$_2$, or N-acyl-N—C$_1$–C$_6$alkylamino; or the two radicals R$_{12}$ and R$_{13}$ are together oxo; or c) of the formula:

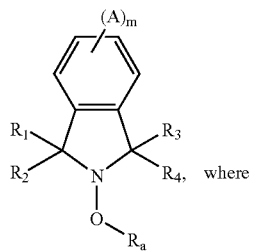

(Ib)

R$_a$ is an acyl radical selected from the group consisting of —C(=O)—H, —C(=O)—C$_1$–C$_{19}$alkyl, —C(=O)—C$_2$–C$_{19}$alkenyl, —C(=O)—C$_2$–C$_4$alkenyl-C$_6$–C$_{10}$aryl, —C(=O)—C$_6$–C$_{10}$aryl, —C(=O)—O—C$_1$–C$_6$alkyl, —C(=O)—O—C$_6$–C$_{10}$aryl, —C(=O)—NH—C$_1$–C$_6$alkyl, —C(=O)—NH—C$_6$–C$_{10}$aryl and —C(=O)—N(C$_1$–C$_6$alkyl)$_2$;

R$_1$–R$_4$ are each C$_1$–C$_6$alkyl;

A is a substituent on the phenyl rings; and m is zero or an integer from one to four; or d) of the formula:

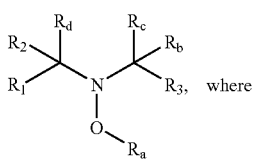

(Ic)

R$_a$ is an acyl radical selected from the group consisting of —C(=O)—H, —C(=O)—C$_1$–C$_{19}$alkyl, —C(=O)—C$_2$–C$_{19}$alkenyl, —C(=O)—C$_2$–C$_4$alkenyl-C$_6$–C$_{10}$aryl, —C(=O)—C$_6$–C$_{10}$aryl, —C(=O)—O—C$_1$–C$_6$alkyl, —C(=O)—O—C$_6$–C$_{10}$aryl, —C(=O)—NH—C$_1$–C$_6$alkyl, —C(=O)—NH—C$_6$–C$_{10}$aryl, —C(=O)—N(C$_1$–C$_6$alkyl)$_2$, —P(=O)—C$_1$–C$_{19}$alkyl, —P(=O)$_2$—C$_1$–C$_{19}$alkyl, —P(=O)—C$_6$–C$_{10}$aryl, —P=O(—C$_1$–C$_{19}$alkyl)$_2$, —P=O(—C$_6$–C$_{10}$aryl)$_2$, —P(=O)—O—C$_1$–C$_6$alkyl, —P(=O)—O—C$_6$–C$_{10}$aryl, —P=O(—O—C$_1$–C$_6$alkyl)$_2$, —P=O(—O—C$_6$–C$_{10}$aryl)$_2$, —P(—O—C$_1$–C$_6$alkyl)$_2$ and —P(—O—C$_6$–C$_{10}$aryl)$_2$;

R$_b$ is as defined for R$_a$ or is carbamoyl, C$_1$–C$_6$akylcarbamoyl or di-C$_1$–C$_6$alkylcarbamoyl;

R$_c$ and R$_d$ are each, independently of one another, hydrogen, C$_1$–C$_6$alkyl or C$_6$–C$_{10}$aryl; and R$_1$–R$_3$ are each, independently of one another, C$_1$–C$_6$alkyl or C$_6$–C$_{10}$aryl.

These compounds are suitable as polymerization initiators, particularly for use in polymerization processes, since they allow the formation of particularly pure polymers and copolymers.

The term polymer encompasses oligomers, cooligomers, polymers and copolymers, for example random block, multi-block, star or gradient copolymers.

A further advantageous property of the novel compounds in process technology is their suitability as additives in processes for lowering the molecular weight of polymers, in particular polypropylenes, and in processes for achieving a controlled increase in the molecular weight of or crosslinking of polyethylene.

The terms and expressions used in the description of the invention preferably have the following meanings:

In the embodiment a), C$_1$–C$_{19}$alkyl in the hydroxylamine esters (Ia) is, for example, C$_1$–C$_6$alkyl, e.g. methyl, ethyl, n-propyl or isopropyl or n-, sec- or tert-butyl or straight-chain or branched pentyl or hexyl, or C$_7$–C$_{19}$alkyl, e.g. straight-chain or branched heptyl, octyl, isooctyl, nonyl, tert-nonyl, decyl or undecyl, or straight-chain C$_{11}$–C$_{19}$alkyl, which together with the —(C=O)— radical forms C$_{14}$–C$_{20}$-alkanoyl having an even number of C-atoms, e.g. lauroyl (C12), myristoyl (C14), palmitoyl (C16) or stearoyl (C18).

C$_6$–C$_{10}$Aryl is, for example, carbocyclic monoaryl or diaryl, preferably monoaryl, e.g. phenyl, which may be monosubstituted or disubstituted by suitable substituents, e.g. C$_1$–C$_4$alkyl, e.g. methyl, ethyl or tert-butyl, C$_1$–C$_4$alkoxy, e.g. methoxy or ethoxy, or halogen, e.g. chlorine. In the case of disubstitution, the 2- and 6-positions are preferred.

The acyl radical R$_a$ selected from the group consisting of —C(=O)—H, —C(=O)—C$_1$–C$_{19}$alkyl, —C(=O)—C$_2$–C$_{19}$alkenyl, —C(=O)—C$_2$–C$_4$alkenyl-C$_6$–C$_{10}$aryl, —C(=O)—C$_6$–C$_{10}$aryl, —C(=O)—O—C$_1$–C$_6$alkyl, —C(=O)—O—C$_6$–C$_{10}$aryl, —C(=O)—NH—C$_1$–C$_6$alkyl, —C(=O)—NH—C$_6$–C$_{10}$aryl and —C(=O)—N(C$_1$–C$_6$alkyl)$_2$ may be substituted on the free valences by suitable substituents, e.g. fluorine or chlorine, and is preferably formyl, acetyl, trifluoroacetyl, pivaloyl, acryloyl, methacryloyl, oleoyl, cinnamoyl, benzoyl, 2,6-xyloyl, tert-butoxycarbonyl, ethylcarbamoyl or phenylcarbamoyl.

C$_1$–C$_6$Alkyl as R$_1$–R$_4$ is preferably C$_1$–C$_4$alkyl, in particular C$_1$–C$_2$alkyl, e.g. methyl or ethyl.

In preferred embodiments, R$_1$–R$_4$ are methyl or ethyl. Alternatively, from one to three substituents R$_1$–R$_4$ are ethyl. The remaining substituents are then methyl.

R$_5$ and R$_6$ are preferably hydrogen. C$_1$–C$_6$Alkyl or C$_6$–C$_{10}$aryl as R$_5$ and R$_6$ are preferably methyl or phenyl.

R$_5$ and R$_6$ are preferably oxygen when Z is the bivalent radical —NR$_{11}$— (R$_{11}$=H or C$_1$–C$_4$alkyl). Q is then a direct bond (five-membered ring) or the bivalent radical —(CR$_7$R$_8$)— (six-membered ring).

R$_7$, R$_8$, R$_9$ and R$_{10}$ in the bivalent radicals —(CR$_7$R$_8$)— or —(CR$_7$R$_8$—CR$_9$R$_{10}$)— are preferably hydrogen, but can also be C$_1$–C$_4$alkyl as defined above, e.g. methyl.

In the bivalent radical —NR$_{11}$—, R$_{11}$ is hydrogen, C$_1$–C$_6$alkyl as defined above, in particular methyl or tert-butyl, aryl, e.g. phenyl, or the acyl radical R$_a$ as defined above, in particular formyl, acetyl, trifluoroacetyl, pivaloyl, benzoyl, 2,6-xyloyl, tert-butoxycarbonyl, ethylcarbamoyl or phenylcarbamoyl.

In the embodiment b), the acyl radical R$_a$ in the hydroxylamine ester (Ia) is selected from the group consisting of —P(=O)—C$_1$–C$_{19}$alkyl, —P(=O)$_2$—C$_1$–C$_{19}$alkyl, —P(=O)—C$_6$–C$_{10}$aryl, —P=O(—C$_1$–C$_{19}$alkyl)$_2$, —P=O(—$C_6$–$C_{10}$aryl)$_2$, —P(=O)—O—$C_1$–$C_6$alkyl, —P(=O)—O—$C_6$–$C_{10}$aryl, —P=O(—O—$C_1$–$C_6$alkyl)$_2$, —P=O(—O—$C_6$–$C_{10}$aryl)$_2$, —P(—O—$C_1$–$C_6$alkyl)$_2$ and —P(—O—$C_6$–$C_{10}$aryl)$_2$. $C_1$–$C_{19}$Alkyl and $C_6$–$C_{10}$aryl are as defined above under a), e.g. methyl or phenyl.

$R_1$–$R_4$ are as defined above under a).

Likewise, $R_5$, $R_6$, Q, $R_7$, $R_8$, $R_9$ and $R_{10}$ are as defined above under a).

$Z_1$ in both the embodiment b) and the embodiment a) may be oxygen or the bivalent radical —$NR_{11}$—. Alternatively, in the embodiment b) $Z_1$ can also be the bivalent radical —($CR_{12}R_{13}$)—, where one of the radicals $R_{12}$ and $R_{13}$ is hydrogen or $C_1$–$C_6$alkyl and the other is $C_1$–$C_6$alkyl, $C_1$–$C_6$alkoxy, e.g. methoxy, ethoxy or n-propoxy, $C_6$–$C_{10}$aryloxy, acyloxy selected from the group consisting of —O—C(=O)—H, —O—C(=O)—$C_1$–$C_{19}$alkyl, —O—C(=O)—$C_1$–$C_{54}$alkenyl, —O—C(=O)—$C_6$–$C_{10}$aryl, —O—C(=O)—$C_1$–$C_{36}$alkenyl-$C_6$–$C_{10}$aryl, —O—C(=O)—O—$C_1$–$C_6$alkyl, —O—C(=O)—O—$C_6$–$C_{10}$aryl, —O—C(=O)—NH—$C_1$–$C_6$alkyl, —O—C(=O)—NH—$C_6$–$C_{10}$aryl and —O—C(=O)—N($C_1$–$C_6$alkyl)$_2$, $C_1$–$C_6$alkylamino, di-$C_1$–$C_6$alkylamino, $C_6$–$C_{10}$arylamino, acylamino selected from the group consisting of —NH—C(=O)—H, —NH—C(=O)—$C_1$–$C_{19}$alkyl, —NH—C(=O)—$C_1$–$C_{54}$alkenyl, —NH—C(=O)—$C_6$–$C_{10}$aryl, —NH—C(=O)—$C_1$–$C_{36}$alkenyl-$C_6$–$C_{10}$aryl, —NH—C(=O)—O—$C_1$–$C_{19}$alkyl, —NH—C(=O)—O—$C_6$–$C_{10}$aryl, —NH—C(=O)—NH—$C_1$–$C_6$alkyl, —NH—C(=O)—NH—$C_6$–$C_{10}$aryl and —NH—C(=O)—N($C_1$–$C_6$alkyl)$_2$, diacylamino selected from the group consisting of —N[—C(=O)—$C_1$–$C_{19}$alkyl]$_2$ and —N[—C(=O)—$C_6$–$C_{10}$aryl]$_2$ or N-acyl-N—$C_1$–$C_6$alkylamino.

Examples of acyloxy are formyloxy, acetoxy, trifluoroacetoxy, pivaloyloxy, benzoyloxy, 2,6-xyloyloxy, tert-butoxycarbonyloxy, ethylcarbamoyloxy or phenylcarbamoyloxy.

Examples of —O—C(=O)—$C_1$–$C_{54}$alkenyl or —O—C(=O)—$C_1$–$C_{36}$alkenyl-$C_6$–$C_{10}$aryl are acid radicals derived from unsaturated dimeric or trimeric acids having a large number of C-atoms, e.g. of the formulae:

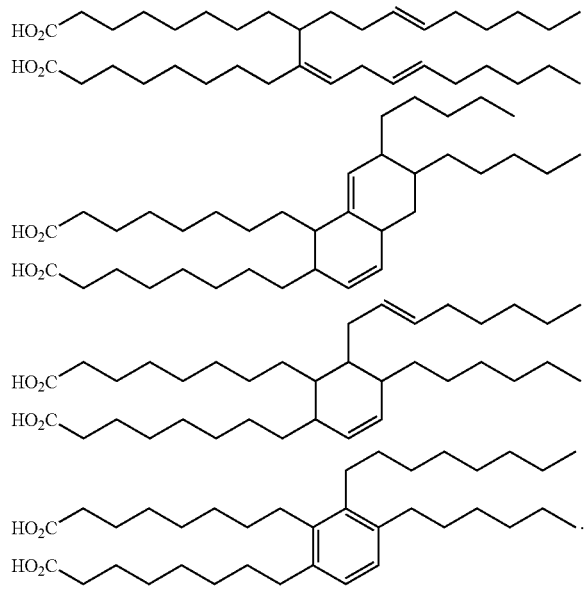

Examples of acylamino are acetylamino, pivaloylamino and tert-butoxycarbonylamino.

Examples of diacylamino are N-acetyl-N-pivaloylamino and diacetylamino.

In the embodiment c), the acyl radical $R_a$ in the hydroxylamine ester (Ib) is selected from the group consisting of —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl and —C(=O)—N($C_1$–$C_6$alkyl)$_2$. These meanings correspond to the definition of the acyl radical $R_a$ in the embodiment a). The acyl radical $R_a$ can be substituted on its free valences by suitable substituents, e.g. fluorine or chlorine, and is preferably formyl, acetyl, trifluoroacetyl, pivaloyl, benzoyl, 2,6-dimethylbenzoyl, tert-butoxycarbonyl, ethylcarbamoyl or phenylcarbamoyl.

$C_1$–$C_6$Alkyl as $R_1$–$R_4$ is, as in the embodiment a), preferably $C_1$–$C_4$alkyl, in particular methyl or ethyl.

The phenyl ring is preferably unsubstituted (m=0). When the phenyl ring is substituted, suitable substituents A on the phenyl ring are, in particular, functional groups selected from the group consisting of amino, $C_1$–$C_4$alkylamino, e.g. methylamino or ethylamino, $C_1$–$C_4$-dialkylamino, e.g. dimethylamino or diethylamino, hydroxy, oxo, thio, —$NO_2$, carboxy and halogen or are substituents selected from the group consisting of $C_1$–$C_{20}$alkyl as defined above and $C_2$–$C_{20}$alkenyl, e.g. vinyl or allyl.

The embodiment d) encompasses open-chain hydroxylamine esters (Ic), where $R_a$ is an acyl radical selected from the group consisting of —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl and —C(=O)—N($C_1$–$C_6$alkyl)$_2$. These meanings correspond to the definitions of the acyl radical $R_a$ in the embodiment a). In a preferred embodiment, $R_a$ is an acyl radical selected from the group consisting of —P(=O)—$C_1$–$C_{19}$alkyl, —P(=O)$_2$—$C_1$–$C_{19}$alkyl, —P(=O)—$C_6$–$C_{10}$aryl, —P=O(—$C_1$–$C_{19}$alkyl)$_2$, —P=O(—$C_6$–$C_{10}$aryl)$_2$, —P(=O)—O—$C_1$–$C_6$alkyl, —P(=O)—O—$C_6$–$C_{10}$aryl, —P=O(—O—$C_1$–$C_6$alkyl)$_2$, —P=O(—O—$C_6$–$C_{10}$aryl)$_2$, —P(—O—$C_1$–$C_6$alkyl)$_2$ and —P(—O—$C_6$–$C_{10}$aryl)$_2$. These meanings correspond to the definitions of the acyl radical $R_a$ with phosphorus-containing acyl groups in the embodiment b).

$R_c$ and $R_d$ and also $C_1$–$C_6$alkyl or $C_6$–$C_{10}$aryl groups $R_1$–$R_3$ are, for example, methyl, ethyl, n-propyl or isopropyl, n-butyl, isobutyl, tert-butyl, phenyl or naphthyl.

A preferred embodiment of the invention provides compounds a) of the formula Ia, where
  $R_a$ is an acyl radical selected from the group consisting of —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—NH—$C_1$–$C_6$alkyl, —C(=O)—NH—$C_6$–$C_{10}$aryl and —C(=O)—N($C_1$–$C_6$alkyl)$_2$;
  $R_1$–$R_4$ are each $C_1$–$C_2$alkyl;
  $R_5$ and $R_6$ are each, independently of one another, hydrogen or $C_1$–$C_6$alkyl or $R_5$ and $R_6$ are together oxygen;
  Q is a single bond or a bivalent radical —($CR_7R_8$)— or —($CR_7R_8$—$CR_9R_{10}$)—, where $R_7$, $R_8$, $R_9$ and $R_{10}$ are each hydrogen; and
$Z_1$ is oxygen or a bivalent radical —$NR_{11}$—, where
$R_{11}$ is hydrogen, $C_1$–$C_6$alkyl or $C_6$–$C_{10}$aryl; or b) of the formula Ia, where
$R_a$ is an acyl radical selected from the group consisting of
—P(=O)—$C_1$–$C_{19}$alkyl, —P(=O)$_2$—$C_1$–$C_{19}$alkyl, —P(=O)—$C_6$–$C_{10}$aryl, —P=O(—$C_1$–$C_{19}$alkyl)$_2$ and —P=O(—$C_6$–$C_{10}$aryl)$_2$;
$R_1$–$R_4$ are each $C_1$–$C_2$alkyl;
$R_5$ and $R_6$ are each, independently of one another, hydrogen, $C_1$–$C_6$alkyl or $R_5$ and $R_6$ are together oxygen;
Q is a single bond or a bivalent radical —(CR$_7$R$_8$)— or —(CR$_7$R$_8$—CR$_9$R$_{10}$)—, where
$R_7$, $R_8$, $R_9$ and $R_{10}$ are each hydrogen; and
$Z_1$ is oxygen or a bivalent radical —$NR_{11}$— or —(CR$_{12}$R$_{13}$)—, where
$R_{11}$ is hydrogen, $C_1$–$C_6$alkyl or $C_6$–$C_{10}$aryl or, independently of one another,
one of the radicals $R_{12}$ and $R_{13}$ is hydrogen and the other is acyloxy selected from the group consisting of —O—C(=O)—$C_1$–$C_{19}$alkyl, —O—C(=O)—$C_6$–$C_{10}$aryl, —O—C(=O)—O—$C_1$–$C_6$alkyl, —O—C(=O)—O—$C_6$–$C_{10}$aryl, —O—C(=O)—NH—$C_1$–$C_6$alkyl, —O—C(=O)—NH—$C_6$–$C_{10}$aryl and —O—C(=O)—N($C_1$–$C_6$alkyl)$_2$; or c) of the formula Ib, where
$R_a$ is an acyl radical selected from the group consisting of —C(=O)—$C_1$–$C_{19}$alkyl, —C(=O)—$C_6$–$C_{10}$aryl, —C(=O)—O—$C_1$–$C_6$alkyl, —C(=O)—NH—$C_1$–$C_6$alkyl, —C(=O)—NH—$C_6$–$C_{10}$aryl and —C(=O)—N($C_1$–$C_6$alkyl)$_2$;
$R_1$–$R_4$ are each $C_1$–$C_2$alkyl; and
m is zero; or d) of the formula Ic, where
$R_a$ is an acyl radical selected from the group consisting of —C(=O)—$C_1$–$C_{19}$alkyl, —C(=O)—$C_6$–$C_{10}$aryl, —C(=O)—O—$C_1$–$C_6$alkyl, —C(=O)—NH—$C_1$–$C_6$alkyl, —C(=O)—NH—$C_6$–$C_{10}$aryl and —C(=O)—N($C_1$–$C_6$alkyl)$_2$, —P(=O)—$C_1$–$C_{19}$alkyl, —P(=O)$_2$—$C_1$–$C_{19}$alkyl, —P(=O)—$C_6$–$C_{10}$aryl, —P=O(—$C_1$–$C_{19}$alkyl)$_2$, —P=O(—$C_6$–$C_{10}$aryl)$_2$, —P(=O)—O—$C_1$–$C_6$alkyl, —P(=O)—O—$C_6$–$C_{10}$aryl, —P=O(—O—$C_1$–$C_6$alkyl)$_2$, —P=O(—O—$C_6$–$C_{10}$aryl)$_2$, —P(—O—$C_1$–$C_6$alkyl)$_2$ and —P(—O—$C_6$–$C_{10}$aryl)$_2$;
$R_b$ is as defined for $R_a$ or is carbamoyl, $C_1$–$C_6$alkylcarbamoyl or di-$C_1$–$C_6$alkylcarbamoyl;
$R_c$ and $R_d$ are each, independently of one another, hydrogen, $C_1$–$C_6$alkyl or $C_6$–$C_{10}$aryl; and
$R_1$–$R_3$ are each $C_1$–$C_2$alkyl or $C_6$–$C_{10}$aryl.

A particularly preferred embodiment of the invention provides compounds a) of the formula Ia, where
$R_a$ is an acyl radical selected from the group consisting of —C(=O)—$C_1$–$C_{19}$alkyl, benzoyl and —C(=O)—O—$C_1$–$C_6$alkyl;
$R_1$–$R_4$ are each $C_1$–$C_2$alkyl;
$R_5$ and $R_6$ are each, independently of one another, hydrogen or methyl or $R_5$ and $R_6$ are together oxygen;
Q is a direct bond or a bivalent radical —(CR$_7$R$_8$)— or —(CR$_7$R$_8$—CR$_9$R$_{10}$)—, where
$R_7$, $R_8$, $R_9$ and $R_{10}$ are each hydrogen; and
$Z_1$ is oxygen or a bivalent radical —$NR_{11}$—, where
$R_{11}$ is hydrogen, $C_1$–$C_6$alkyl or $C_6$–$C_{10}$aryl; or b) of the formula Ia, where
$R_a$ is an acyl radical selected from the group consisting of —P(=O)$_2$—$C_1$–$C_{19}$alkyl, —P=O(—$C_1$–$C_{19}$alkyl)$_2$ and —P=O(—$C_6$–$C_{10}$aryl)$_2$;
$R_1$–$R_4$ are each $C_1$–$C_2$alkyl;
$R_5$ and $R_6$ are each, independently of one another, hydrogen, $C_1$–$C_6$alkyl or $R_5$ and $R_6$ are together oxygen;
Q is a direct bond or a bivalent radical —(CR$_7$R$_8$)— or —(CR$_7$R$_8$—CR$_9$R$_{10}$)—, where
$R_7$, $R_8$, $R_9$ and $R_{10}$ are each hydrogen; and
$Z_1$ is oxygen or a bivalent radical —$NR_{11}$— or —(CR$_{12}$R$_{13}$)—, where
$R_{11}$ is hydrogen, $C_1$–$C_6$alkyl or $C_6$–$C_{10}$aryl or, independently of one another,
one of the radicals $R_{12}$ and $R_{13}$ is hydrogen and the other is acyloxy selected from the group consisting of —O—C(=O)—$C_1$–$C_{19}$alkyl, benzoyl, —O—C(=O)—O—$C_1$–$C_6$alkyl and benzyloxycarbonyloxy; or c) of the formula Ib, where
$R_a$ is an acyl radical selected from the group consisting of —C(=O)—$C_1$–$C_{19}$alkyl, benzoyl and —C(—O)—O—$C_1$–$C_6$alkyl;
$R_1$–$R_4$ are each $C_1$–$C_2$alkyl; and
m is zero; or d) of the formula Ic, where
$R_a$ is an acyl radical selected from the group consisting of —C(=O)—$C_1$–$C_{19}$alkyl, benzoyl, —C(=O)—O—$C_1$–$C_6$alkyl, —P(=O)$_2$—$C_1$–$C_{19}$alkyl, —P=O(—$C_1$–$C_{19}$alkyl)$_2$ and —P=O(—$C_6$–$C_{10}$aryl)$_2$;
$R_b$ is as defined for $R_a$ or is carbamoyl, $C_1$–$C_6$alkylcarbamoyl or di-$C_1$–$C_6$alkylcarbamoyl;
$R_c$ and $R_d$ are each, independently of one another, hydrogen, $C_1$–$C_6$alkyl or $C_6$–$C_{10}$aryl; and
$R_1$–$R_3$ are each, independently of one another, $C_1$–$C_2$alkyl or $C_6$–$C_{10}$aryl.

The above-described compounds according to the embodiments a)–d) are novel and can be prepared by methods known per se. The compounds are present as polymerization auxiliaries or polymerization initiators in polymerizable compositions which comprise at least one ethylenically unsaturated, polymerizable monomer or oligomer and a compound according to one of the above-described embodiments a) to d).

The invention therefore further provides a composition comprising
A) at least one ethylenically unsaturated, polymerizable monomer or oligomer; and
B) at least one of the above-described compounds a)–d).

Suitable ethylenically unsaturated monomers or oligomers can be polymerized in a manner known per se using the methods of free-radical polymerization.

Monomers suitable for free-radical polymerization are, for example, ethylenically unsaturated polymerizable monomers selected from the group consisting of alkenes, conjugated dienes, styrenes, acrolein, vinyl acetate, vinylpyrrolidone, vinylimidazole, maleic anhydride, acrylic acid, acrylic acid derivatives, vinyl halides and vinylidene halides.

Examples of alkenes and conjugated alkenes are ethylene, isoprene, 1,3-butadiene and α-$C_5$–$C_{18}$alkenes.

Suitable styrenes may be substituted on the phenyl group by from one to three substituents selected from the group consisting of hydroxy, $C_1$–$C_4$alkoxy, e.g. methoxy or ethoxy, halogen, e.g. chlorine, amino and $C_1$–$C_4$alkyl, e.g. methyl or ethyl.

Suitable acrylic acid derivatives are selected, for example, from the group consisting of $C_1$–$C_4$alkylacrylic acids, amides, nitriles, anhydrides and salts of acrylic acid and of $C_1$–$C_4$alkylacrylic acids, $C_1$–$C_{24}$alkyl acrylates and $C_1$–$C_{24}$alkyl $C_1$–$C_4$alkylacrylates.

Particularly preferred acrylic acid derivatives are methacrylic acid or salts thereof, acrylic anhydride and methacrylic anhydride, $C_1$–$C_{24}$alkyl acrylates and methacrylates, mono- or di-$C_1$–$C_4$alkylamino-$C_2$–$C_4$alkyl acrylates and methacrylates, hydroxy-$C_2$–$C_4$alkyl acrylates and methacrylates, ($C_1$–$C_4$alkyl)$_3$silyloxy-$C_2$–$C_4$alkyl acrylates and methacrylates, ($C_1$–$C_4$alkyl)$_3$silyl-$C_2$–$C_4$alkyl acrylates and methacrylates, heterocyclyl-$C_2$–$C_4$alkyl acrylates and methacrylates, acrylic and methacrylic esters having poly-$C_2$–$C_4$alkylene glycol ester groups which may in turn be esterified by substituted $C_1$–$C_{24}$alkoxy groups, acrylamides and methacrylamides, mono- or di-$C_1$–$C_4$alkylamides of acrylic and methacrylic acids, amino-$C_2$–$C_4$alkylamides of acrylic and methacrylic acids and acrylonitrile.

Suitable salts of acrylic acid or methacrylic acid are, for example, ($C_1$–$C_4$alkyl)$_4$ammonium or ($C_1$–$C_4$alkyl)$_3$NH salts, e.g. the tetramethylammonium, tetraethylammonium, trimethylammonium or triethylammonium salt, the trimethyl-2-hydroxyethylammonium or triethyl-2-hydroxyethylammonium salt, the dimethyl-2-hydroxyethylammonium or diethyl-2-hydroxyethylammonium salt.

Suitable $C_1$–$C_{24}$alkyl acrylates and methacrylates are esterified by, for example, methyl, ethyl, n-butyl, isobutyl, tert-butyl, 2-ethylhexyl, isobornyl, isodecyl, lauryl, myristyl, stearyl or behenyl.

Examples of mono- or di-$C_1$–$C_4$alkylamino-$C_2$–$C_4$alkyl acrylates and methacrylates are 2-monomethylaminoethyl acrylate or methacrylate, 2-dimethylaminoethyl acrylate or methacrylate and the corresponding 2-monoethylaminoethyl or 2-diethylaminoethyl esters and also 2-tert-butylaminoethyl acrylate or methacrylate.

Examples of hydroxy-$C_2$–$C_4$alkyl acrylates and methacrylates are 2-hydroxyethyl acrylate or methacrylate (HEA, HEMA) and 2-hydroxypropyl acrylate or methacrylate (HPA, HPMA).

Examples of silyloxy-$C_2$–$C_4$alkyl acrylates and methacrylates are 2-trimethylsilyloxyethyl acrylate or methacrylate (TMS-HEA, TMS-HEMA). Examples of ($C_1$–$C_4$alkyl)$_3$silyl-$C_2$–$C_4$alkyl acrylates and methacrylates are 2-trimethylsilylethyl acrylate or methacrylate and 3-trimethylsilyl-n-propyl acrylate or methacrylate.

Acrylic or methacrylic esters having poly-$C_2$–$C_4$alkylene glycol ester groups which may in turn be esterified by substituted $C_1$–$C_{24}$alkoxy groups have the formula:

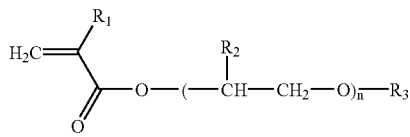

where $R_1$ and $R_2$ are each, independently of one another, hydrogen or methyl and $R_3$ is $C_1$–$C_{24}$alkyl, e.g. methyl, ethyl, n-propyl or isopropyl, n-butyl, isobutyl or tert-butyl, n-pentyl or neopentyl, lauryl, myristyl or stearyl, or aryl-$C_1$–$C_{24}$alkyl, e.g. benzyl or phenyl-n-nonyl, or else $C_1$–$C_{24}$alkylaryl or $C_1$–$C_{24}$alkylaryl-$C_1$–$C_{24}$alkyl.

Examples of heterocycyl-$C_2$–$C_4$alkyl acrylates and methacrylates are 2-(N-morpholinyl, -2-pyridyl, -1-imidazolyl, -2-oxo-1-pyrrolidinyl, -4-methylpiperidin-1-yl or -2-oxoimidazolidin-1-yl)ethyl acrylate or methacrylate.

Examples of the abovementioned mono- or di-$C_1$–$C_4$alkylamides of acrylic acid and methacrylic acid, di-$C_1$–$C_4$alkylamino-$C_2$–$C_4$alkylamides of acrylic acid and methacrylic acid or amino-$C_2$–$C_4$alkylamides of acrylic acid and methacrylic acid are N,N-dimethylacrylamide, N,N-dimethyl(meth)acrylamide, 2-(N,N-dimethylaminoethyl) acrylamide, 2-(N,N-dimethylaminoethyl)methacrylamide, 2-aminoethylacrylamide and 2-aminoethylmethacrylamide.

The abovementioned acrylic acid derivatives are present in the polymerizable composition as monomers or in admixture with acrylic acid.

In the composition, the component B) is present in a ratio to the component A) of from 0.01 to 30 mol %, preferably from 0.05 to 10 mol %, particularly preferably from 0.1 to 1.0 mol %.

A preferred composition according to the invention is a composition comprising

A) at least one ethylenically unsaturated, polymerizable monomer or oligomer selected from the group consisting of monomeric and oligomeric alkenes, styrenes, conjugated dienes, acrolein, vinyl acetate, vinylpyrrolidone, vinylimidazole, maleic anhydride, acrylic acid, $C_1$–$C_4$alkylacrylic acids, amides, nitriles, anhydrides and salts of acrylic acid and $C_1$–$C_4$alkylacrylic acids, $C_1$–$C_{24}$alkyl acrylates, $C_1$–$C_{24}$alkyl-$C_1$–$C_4$alkylacrylates, vinyl halides and vinylidene halides; and B) at least one of the abovementioned compounds a)–d).

The above-described compositions may further comprise customary additives, which may, as an alternative, also be added after the polymerization. Such additives can be added in small amounts, e.g. UV-absorbers or light stabilizers, e.g. compounds selected from the group consisting of hydroxyphenylbenzotriazoles, hydroxyphenylbenzophenones, oxalamides and hydroxyphenyl-s-triazines. Particularly suitable light stabilizers are those selected from the group consisting of sterically hindered amines (HALS), e.g. of the 2-(2-hydroxyphenyl)- 1,3,5-triazine or 2-hydroxyphenyl-2H-benzotriazole type. Examples of light stabilizers of the 2-(2-hydroxyphenyl)-1,3,5-triazine type are known from the patent literature, e.g. U.S. Pat. No. 4,619,956, EP-A-434 608, U.S. Pat. No. 5,198,498, U.S. Pat. No. 5,322,868, U.S. Pat. No. 5,369,140, U.S. Pat. No. 5,298,067, WO-94/18278, EP-A-704 437, GB-A-2,297,091 or WO-96/28431.

The compositions may further comprise other customary additives, e.g. fillers such as calcium carbonate, silicates, glass or glass fibre material, talcum, kaolin, mica, barium sulphate, metal oxides and hydroxides, carbon black, graphite, pulverized wood and pulverized or fibrous material from other natural products, synthetic fibres, plasticizers, lubricants, emulsifiers, pigments, fluidizers, catalysts, optical brighteners, flame retardants, antistatics or blowing agents.

The abovementioned polymers can be present in the composition in concentrations of from about 0.01 to 99.0% by weight, preferably from 0.1 to 95% by weight, in particular from 1.0 to 90.0% by weight, especially from 5.0 to 80.0% by weight, based on the monomer content of the composition.

The invention further provides a process for preparing the above-described oligomer, cooligomer, polymer or copolymer by free-radical polymerization using either the above-described novel compounds according to the embodiments a)–d) or known hydroxylamines wherein the hydroxy group is esterified by the defined acyl radicals $R_a$.

A preferred embodiment provides a process for preparing an oligomer, a cooligomer, a polymer or a copolymer by free-radical polymerization, characterised in that a composition comprising
- α) at least one ethylenically unsaturated, polymerizable monomer or oligomer; and
- β) one of the above-defined novel compounds a)–d)

is subjected to the reaction conditions of a free-radical polymerization.

The invention likewise provides a process for preparing an oligomer, a cooligomer, a polymer or a copolymer by free-radical polymerization, characterised in that a composition comprising
- α) an ethylenically unsaturated, polymerizable monomer or oligomer; and
- β) at least one compound of the formula Ia, where
  $R_a$ is an acyl radical selected from the group consisting of —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl, —C(=O)—N($C_1$–$C_6$alkyl)$_2$, —P(=O)—$C_1$–$C_{19}$alkyl, —P(=O)$_2$—$C_1$–$C_{19}$alkyl, —P(=O)—$C_6$–$C_{10}$aryl, —P=O(—$C_1$–$C_{19}$alkyl)$_2$, —P=O(—$C_6$–$C_{10}$aryl)$_2$, —P(=O)—O—$C_1$–$C_6$alkyl, —P(=O)—O—$C_6$–$C_{10}$aryl, —P=O(—O—$C_1$–$C_6$alkyl)$_2$, —P=O(—O—$C_6$–$C_{10}$aryl)$_2$, —P(—O—$C_1$–$C_6$alkyl)$_2$ and —P(—O—$C_6$–$C_{10}$aryl)$_2$;
  $R_1$–$R_4$ are each $C_1$–$C_6$alkyl;
  $R_5$ and $R_6$ are each, independently of one another, hydrogen, $C_1$–$C_6$alkyl or $C_6$–$C_{10}$aryl; or
  $R_5$ and $R_6$ are together oxygen;
  Q is a direct bond or a bivalent radical —($CR_7R_8$)— or —($CR_7R_8$—$CR_9R_{10}$)—, where
  $R_7$, $R_8$, $R_9$ and $R_{10}$ are each, independently of one another, hydrogen or $C_1$–$C_6$alkyl; and
  $Z_1$ is oxygen or a bivalent radical —$NR_{11}$— or —($CR_{12}R_{13}$)—, where
  $R_{11}$ is hydrogen, $C_1$–$C_6$alkyl, $C_6$–$C_{10}$aryl or the acyl radical $R_a$ having the above meanings; or, independently of one another,
  $R_{12}$ and $R_{13}$ are each hydrogen or $C_1$–$C_6$alkyl; or
  one of the radicals $R_{12}$ and $R_{13}$ is hydrogen or $C_1$–$C_6$alkyl and the other is $C_1$–$C_6$alkyl, $C_1$–$C_6$alkoxy, aryloxy, acyloxy selected from the group consisting of —O—C(=O)—H, —O—C(=O)—$C_1$–$C_{19}$alkyl, —O—C(=O)—$C_1$–$C_{54}$alkenyl, —O—C(=O)—$C_6$–$C_{10}$aryl, —O—C(=O)—$C_1$–$C_{36}$alkenyl-$C_6$–$C_{10}$aryl, —O—C(=O)—O—$C_1$–$C_6$alkyl, —O—C(=O)—O—$C_6$–$C_{10}$aryl, —O—C(=O)—NH—$C_1$–$C_6$alkyl, —O—C(=O)—NH—$C_6$–$C_{10}$aryl and —O—C(=O)—N($C_1$–$C_6$alkyl)$_2$, $C_1$–$C_6$alkylamino, di-$C_1$–$C_6$alkylamino, $C_6$–$C_{10}$arylamino, acylamino selected from the group consisting of —NH—C(=O)—H, —NH—C(=O)—$C_1$–$C_{19}$alkyl, —NH—C(=O)—$C_1$–$C_{54}$alkenyl, —NH—C(=O)—$C_6$–$C_{10}$aryl, —NH—C(=O)—$C_1$–$C_{36}$alkenyl-$C_6$–$C_{10}$aryl, —NH—C(=O)—O—$C_1$–$C_{19}$alkyl, —NH—C(=O)—O—$C_6$–$C_{10}$aryl, —NH—C(=O)—NH—$C_1$–$C_6$alkyl, —NH—C(=O)—NH—$C_6$–$C_{10}$aryl and —NH—C(=O)—N($C_1$–$C_6$alkyl)$_2$, diacylamino selected from the group consisting of —N[—C(=O)—$C_1$–$C_{19}$alkyl]$_2$, —N[—C(=O)—$C_6$–$C_{10}$aryl]$_2$, —N[—C(=O)—$C_1$–$C_6$alkylene-C(=O)—], —N[—C(=O)—$C_2$–$C_6$alkenylene-C(=O)—] and phthalimido or N-acyl-N—$C_1$–$C_6$alkylamino;
  or the two radicals $R_{12}$ and $R_{13}$ are together oxo; or of the formula Ib, where
  $R_a$ is an acyl radical selected from the group consisting of —C(=O)—H, —C(=O)—$C_1$–$C_{19}$alkyl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl and —C(=O)—N($C_1$–$C_6$alkyl)$_2$;
  $R_1$–$R_4$ are each $C_1$–$C_6$alkyl;
  A is a substituent on the phenyl ring; and
  m is an integer from one to four; or of the formula Ic, where
  $R_a$ is an acyl radical selected from the group consisting of —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl, —C(=O)—N($C_1$–$C_6$alkyl)$_2$, —P(=O)—$C_1$–$C_{19}$alkyl, —P(=O)$_2$—$C_1$–$C_{19}$alkyl, —P(=O)—$C_6$–$C_{10}$aryl, —P=O(—$C_1$–$C_{19}$alkyl)$_2$, —P=O(—$C_6$–$C_{10}$aryl)$_2$, —P(=O)—O—$C_1$–$C_6$alkyl, —P(=O)—O—$C_6$–$C_{10}$aryl, —P=O(—O—$C_1$–$C_6$alkyl)$_2$, —P=O(—O—$C_6$–$C_{10}$aryl)$_2$, —P(—O—$C_1$–$C_6$alkyl)$_2$ and —P(—O—$C_6$–$C_{10}$aryl)$_2$;
  $R_b$ is hydrogen, carbamoyl, $C_1$–$C_6$alkylcarbamoyl, di-$C_1$–$C_6$alkylcarbamoyl or is as defined for $R_a$;
  $R_c$ and $R_d$ are each, independently of one another, hydrogen, $C_1$–$C_{20}$alkyl or $C_6$–$C_{10}$aryl; and
  $R_1$–$R_3$ are each, independently of one another, hydrogen or $C_1$–$C_6$alkyl or $C_6$–$C_{10}$aryl;

is subjected to the reaction conditions of a free-radical polymerization.

In the hydroxylamine esters (Ia), diacylamino as $R_{12}$ or $R_{13}$ is, for example, —N[—C(=O)—$C_1$–$C_6$alkylene-C(=O)—], e.g. of the partial formula:

or —N[—C(=O)—$C_2$–$C_6$alkenylene-C(=O)—], e.g. of the partial formula:

or the phthalimido group:

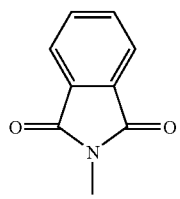

The free-radical polymerization is carried out by dissociation of the initiators defined above by treatment with ultrasound, heating or action of electromagnetic radiation in the range from γ-rays to microwaves. The initiator is preferably dissociated thermally, preferably at a temperature of from 50° C. to 160° C., in particular from 80° C. to 150° C. After the polymerization step has been completed, the reaction mixture can be allowed to cool to a temperature below 60° C., preferably room temperature.

In an alternative embodiment of the process the polymerisation is effected in the presence of an energy intensive light source providing light in the near infrared range (NIR) of about 800–1200 nm. Such light sources are commercially available from AdPhos (cf. www.adphos.de). The high thermal energy of such light sources is particularly suitable for the preparation of thermally curable lacquers (especially powder coatings or adhesives) in the presence of the of the polymerisation initiators defined above. Additional components in these lacquers are the ones conventionally used in the preparation of clear or pigment coatings.

The polymerization process can be carried out in the presence of water or an organic solvent or mixtures thereof. It is possible to add additional cosolvents or surfactants, for example glycols or ammonium salts of carboxylic acids, to the reaction mixture. The abovementioned monomers or oligomers can be present in the reaction mixture in a concentration of from 1.0 to 99.9% by weight, preferably from 5.0 to 99.9% by weight, particularly preferably from 50.0 to 99.9% by weight, based on the monomer content of the polymer. Suitable organic solvents are alkanes (hexane, heptane, octane, isooctane), hydrocarbons (benzene, toluene, xylene), halogenated hydrocarbons (chlorobenzene), alkanols (methanol, ethanol, ethylene glycol, ethylene glycol monomethyl ether), esters (ethyl acetate) or ethers (diethyl ether, dibutyl ether, ethylene glycol dimethyl ether, tetrahydrofuran) or mixtures thereof.

When using water as solvent, a water-miscible or hydrophilic solvent can be added to the reaction mixture. Care should be taken to ensure that the reaction mixture remains as a single homogeneous phase during the polymerization reaction and no precipitation or phase separation takes place. Suitable cosolvents can be selected from the group consisting of aliphatic alcohols, glycols, ethers, glycol ethers, pyrrolidines, N-alkylpyrrolidinones, polyethylene glycols, polypropylene glycols, amides, carboxylic acids and their salts, esters, organic sulfides, sulfoxide, sulfones, alcohol derivatives, hydroxyether derivatives, e.g. butyl carbitol or cellosolve, amino alcohols, ketones, derivatives and mixtures thereof, e.g. methanol, ethanol, propanol, dioxane, ethylene glycol, propylene glycol, diethylene glycol, glycerol, dipropylene glycol, tetrahydrofuran or other water-soluble or water-miscible solvents or mixtures thereof.

Hydrophilic monomers, polymers and copolymers can be separated from the reaction mixture using customary methods, for example by distillation, precipitation, extraction, alteration of the pH or other customary separation methods.

The polymers which can be prepared by the process of the invention may have a number average molecular weight of from 1 000 to 400 000 g/mol, preferably from 2 000 to 250 000 g/mol and particularly preferably from 2 000 to 200 000 g/mol. The number average molecular weight can be determined by gel permeation chromatography (GPC), matrix-aided LASER desorption/ionization mass spectrometry (MALDI-MS) or, when the initiator bears a group distinguishable from the monomers, by NMR spectroscopy or other customary methods.

The present invention therefore also provides for the preparation of novel oligomers, cooligomers, polymers or copolymers, for example random block, multiblock, star or gradient copolymers.

The polymers which can be prepared by the process of the invention and the compositions of the present invention can be used for a variety of applications in process technology, e.g. as adhesives, laundry detergent auxiliaries, detergents, dispersants, emulsifiers, surfactants, antifoams, adhesion promoters, corrosion inhibitors, viscosity improvers, lubricants, flow improvers, thickeners, crosslinkers, as additives for water treatment, electronic materials, paints and varnishes, coatings, inks, photographic developers, superabsorbents, cosmetics, preservatives or as biocides or modifiers and auxiliaries for asphalt, textiles, ceramic and wood.

The invention further provides a generally applicable, inventive process for lowering the molecular weight of polypropylene, propylene copolymers or polypropylene blends using either the above-described novel compounds or known hydroxylamines esters, wherein the hydroxy group is esterified by the defined acyl radicals $R_a$.

The controlled preparation of polyolefin grades (polymer types having different molar masses, melt viscosities, densities, molar mass distributions, etc.) by customary compounding methods, for example by extrusion or injection moulding, is a process employed by polymer manufacturers and polymer processors/compounders.

The setting of the desired parameters, for example the melt viscosity, by means of this polymer process step is critically dependent on the controlled reactivity and mode of action of the additives employed.

The use of free-radical formers for modifying the melt viscosity (rheology) of polyolefins is a generally known method. Whether it results in a lowering of the molecular weight (degradation) or an increase in the molecular weight (crosslinking) depends primarily on the chemical structure of the polyolefin.

The reaction of a polymer of the polypropylene type with a free-radical former during a polymer-processing process generally results in a polymer degradation whereas polymers of the polyethylene type tend to crosslinking. Examples which may be mentioned here are polyethylene types which are obtainable by means of Phillips catalysts (LDPE) or metallocene catalysts (LLDPE). Exceptions are the polyethylene types prepared by the Ziegler process, which likewise tend to undergo chain degradation when processed in the presence of free-radical formers.

In the case of copolymers and terpolymers or copolymer blends, high proportions of propylene produce polypropylene-like behaviour, while high proportions of ethylene result in polyethylene-like behaviour. If the abovementioned copolymers and terpolymers or copolymer blends comprise proportions of multiply unsaturated olefins, the probability of crosslinking decreases with decreasing concentration of free double bonds.

The controlled degradation of polypropylene (PP) to give a product having a lower molecular weight and a narrower molecular weight distribution is a commercially important process for producing 'controlled rheology' polypropylene (CR-PP). While specific PP grades ("reactor grades") are obtainable by optimization of the synthesis process or the catalyst systems (metallocene catalyst, Ziegler catalyst), standard PP grades are frequently modified in process technology by means of a processing step following the synthesis.

Known degradation processes proceed either thermally, in particular at temperatures above 280° C., or in the presence of free-radical generators. In process technology, the free-radical-induced process is carried out in extruders or injection-moulding machines at temperatures above 180° C. Free-radical generators used are organic peroxides which are added during the processing step in diluted form (PP Mastermix, diluted in oil, stabilized on inorganic supports) or directly as a liquid. Under the given processing conditions, the peroxide disintegrates into free radicals which initiate the chain cleavage reactions and form polymers having the desired Theological properties (melt viscosities). The degradation of a PP to form a product having a lower molecular weight (higher melt flow rate (MFR)) is generally referred to as a viscosity-breaking or vis-breaking process.

CR-PP grades are mainly used for fibre applications and injection-moulding applications in which low melt viscosities are a prerequisite for economical processing. A wide range of melt viscosities or molecular weights is nowadays required in process technology.

A further parameter which, in addition to the molecular weight, influences the processing behaviour of the polymer is the molecular weight distribution (MWD). While polymer grades having broad MWDs display improved orientation behaviour of the polymer chains at low pull off speeds in a fibre spinning process, the reverse is the case for high pull off speeds and broad MWDs. For this reason, narrow MWDs are essential at high pull off speeds in order to achieve improved continuity in the spinning process.

The use of peroxides is a drawback, since only a restricted "processing temperature window" is available because of their decomposition temperatures, which are generally below the customary temperatures of polymer processing. In addition, strict safety regulations have to be adhered to during storage, handling and processing of peroxides. A further disadvantage of peroxides is the impossibility of decomposition-free melt compounding with polymers.

Apart from peroxides, other sources of free radicals are also known, e.g. C-radical generators based on cumyl systems, but these can be used only at temperatures above 280° C. WO 97/49737 describes a process for reducing the molecular weight of polymers at temperatures above 280° C. using NOR-HALS compounds containing the group:

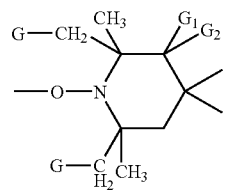

where G is hydrogen or methyl and $G_1$ and $G_2$ are each hydrogen, methyl or are together oxo. These known NOR-HALS compounds produce appreciable polymer degradation only at temperatures above 280° C. Since most polymers are processed below this temperature at 160–280° C., there is a particular need for compounds which can be used at correspondingly lower temperatures.

It is therefore an object of the invention to provide compounds which are suitable for processes for preparing CR-PP and which solve the problems associated with the unfavourably high process temperatures or the use of peroxides, e.g. safety problems.

It has surprisingly been found that open-chain and cyclic hydroxylamines of various structures are particularly suitable as free-radical formers if they are esterified by acyl radicals on the >NO—H group.

The invention also relates to process for reducing the molecular weight of polypropylene, propylene copolymers or polypropylene blends, characterised in that at least one hydroxylamine ester or a polymer of a hydroxylamine ester of the formula:

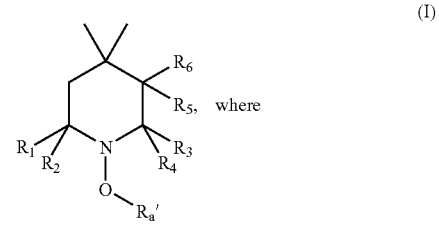

$R_a'$ is a monoacyl or diacyl radical;
$R_1$–$R_4$ are each $C_1$–$C_6$alkyl; and
$R_5$ and $R_6$ are each, independently of one another, hydrogen, $C_1$–$C_6$alkyl or $C_6$–$C_{10}$aryl; or
$R_5$ and $R_6$ are together oxygen, is added to the polypropylene, propylene copolymer or polypropylene blend to be degraded and the mixture is heated.

Preference is given to the process using compounds (I), in which $R_a$ is $C_2$–$C_{18}$alkanoyl or $C_3$–$C_6$alkenoyl.

A monoacyl radical $R_a'$ may be, for example, the acyl radical derived from a monobasic organic acid comprising C radicals and an acid function, e.g. one of the above-defined acyl radicals of the partial formulae —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl and —C(=O)—N($C_1$–$C_6$alkyl)$_2$.

When $R_a'$ is a monoacyl radical, hydroxylamine esters (I) are monomeric or dimeric structures. Thus, dimeric structures have suitable bivalent substituents in the 4-position and these are in turn substituted in the terminal position by compounds (I) via their 4-position (α,ω-substitution).

The term hydroxylamine ester encompasses both monomeric and oligomeric compounds and also polymers formed by compounds of the formula I.

A diacyl radical $R_a'$ may be, for example, the diacyl radical derived from a monobasic organic acid having C radicals and two acid functions, e.g. a diacyl radical derived from an aliphatic, aromatic or cycloaliphatic dicarboxylic acid.

Suitable aliphatic dicarboxylic acids have from 2 to 40 C-atoms, e.g. oxalic acid, malonic acid, dimethylmalonic acid, succinic acid, pimelic acid, adipic acid, trimethyladipic acid, sebacic acid, azelaic acid and dimeric acid (dimerization products of unsaturated aliphatic carboxylic acids such as oleic acid), alkylated malonic and succinic acids, e.g. octadecylsuccinic acid.

Suitable cycloaliphatic dicarboxylic acids are, for example, 1,3-cyclobutanedicarboxylic acid, 1,3-cyclopentanedicarboxylic acid, 1,3- and 1,4-cyclohexanedicarboxylic acid, 1,3- and 1,4-(dicarboxymethyl)cyclohexane or 4,4'-dicyclohexyldicarboxylic acid.

Suitable aromatic dicarboxylic acids are, for example, terephthalic acid, isophthalic acid, o-phthalic acid, and also 1,3-, 1,4-, 2,6- or 2,7-naphthalenedicarboxylic acid, 4,4'-biphenyldicarboxylic acid, bis(4-carboxyphenyl) sulfone, 4,4'-benzophenonedicarboxylic acid, 1,1,3-trimethyl-5-carboxy-3-(p-carboxyphenyl)indane, bis(4-carboxyphenyl) ether, bis(p-carboxyphenyl) methane or bis(p-carboxyphenyl)ethane.

Preference is given to aromatic dicarboxylic acids, in particular terephthalic acid, isophthalic acid and 2,6-naphthalenedicarboxylic acid.

Further suitable dicarboxylic acids are ones containing —CO—NH— groups. These are described in DE-A-2,414,349. Also suitable are dicarboxylic acids containing N-heterocyclic rings, e.g. those derived from carboxyalkylated, carboxyphenylated or carboxylbenzylated monoamine-s-triazinedicarboxylic acids (cf. DE-A-2,121,184 and 2,533,675), monohydantoins or bishydantoins, halogenated or unhalogenated benzimidazoles or parabaric acid. The carboxyalkyl groups may contain from 3 to 20 C-atoms.

When $R_a'$ is a diacyl radical and a suitable functional group, e.g. hydroxy or amino, is present in the 4-position, compounds of the formula I are polymeric structures, e.g. polyesters, polyesteramides, polyurethanes, polycarbonates or polyimide esters.

The process is of particular importance when using compounds (I) belonging to the group consisting of sterically hindered amine derivatives, e.g. compounds of the formula:

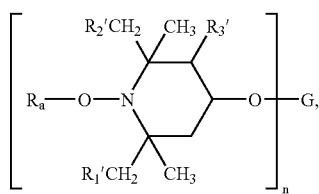

(IA)

where n is an integer from 1 to 4, $R_a$ is acyl and $R_1'$, $R_2'$ and $R_3'$ are each, independently of one another, hydrogen or methyl; and G has the following meanings:

when n=1,
hydrogen, $C_1$–$C_{18}$alkyl which may be interrupted by one or more oxygen atoms, 2-cyanoethyl, benzyl, glycidyl, the monovalent radical of an aliphatic, cycloaliphatic, araliphatic, unsaturated or aromatic carboxylic acid, carbamic acid or phosphorus-containing acid or a monovalent silyl radical, preferably the acyl radical of an aliphatic carboxylic acid having from 2 to 18 C-atoms, of a cycloaliphatic carboxylic acid having from 7 to 15 C-atoms, of an α,β-unsaturated carboxylic acid having from 3 to 5 C-atoms or of an aromatic carboxylic acid having from 7 to 15 C-atoms, where the carboxylic acid may be substituted in the aliphatic, cycloaliphatic or aromatic part by from 1 to 3 —COOZ$^1$ groups, where $Z^1$ is hydrogen, $C_1$–$C_{20}$alkyl, $C_3$–$C_{12}$alkenyl, $C_5$–$C_7$cycloalkyl, phenyl or benzyl; or when n=2,
$C_2$–$C_{12}$alkylene, $C_4$–$C_{12}$alkenylene, xylylene, the divalent acid radical of an aliphatic, cycloaliphatic, araliphatic or aromatic dicarboxylic acid, dicarbamic acid or phosphorus-containing acid, or a divalent silyl radical, preferably the acyl radical of an aliphatic dicarboxylic acid having from 2 to 36 C-atoms, of a cycloaliphatic or aromatic dicarboxylic acid having from 8 to 14 C-atoms or of an aliphatic, cycloaliphatic or aromatic dicarbamic acid having from 8 to 14 C-atoms, where the dicarboxylic acid may be substituted in the aliphatic, cycloaliphatic or aromatic part by 1 or 2 —COOZ$^1$ groups, where $Z^1$ is as defined above; or when n=3,
the trivalent acid radical of an aliphatic, cycloaliphatic or aromatic tricarboxylic acid, where the radical may be substituted in the aliphatic, cycloaliphatic or aromatic part by —COOZ$^1$, where $Z^1$ is as defined above, or the trivalent acid radical of an aromatic tricarbamic acid or a phosphorus-containing acid, or a trivalent silyl radical; or, when n=4,
the tetravalent acid radical of an aliphatic, cycloaliphatic or aromatic tetracarboxylic acid.

G defined as $C_1$–$C_{18}$Alkyl may, for example, have the meanings indicated above for alkyl and may additionally be, for example, n-tridecyl, n-tetradecyl, n-hexadecyl or n-octadecyl.

A monovalent acyl radical of a carboxylic acid as G may be, for example, the acyl radical of acetic acid, hexanoic acid, stearic acid, acrylic acid, methacrylic acid, benzoic acid or β-(3,5-di-tert-butyl-4-hydroxyphenyl)propionic acid; preferably the acyl radical of stearic acid, acrylic acid or methacrylic acid.

A monovalent silyl radical G may be, for example, a radical —$(C_nH_{2n})$—Si(Z')$_2$Z", where n is an integer from 2 to 5 and Z' and Z" are each, independently of one another $C_1$–$C_4$alkyl or $C_1$–$C_4$alkoxy.

A divalent acid radical of a dicarboxylic acid as G may be, for example, the acid radical of malonic acid, succinic acid, glutaric acid, adipic acid, suberic acid, sebacic acid, maleic acid, itaconic acid, phthalic acid, dibutylmalonic acid, dibenzylmalonic acid, butyl(3,5-di-tert-butyl-4-hydroxybenzyl)malonic acid or bicycloheptenedicarboxylic acid.

A trivalent radical of a tricarboxylic acid as G may be, for example, the acid radical of trimellitic acid, citric acid or nitrilotriacetic acid.

A tetravalent radical of a tetracarboxylic acid as G may be, for example, the tetravalent acid radical of butane-1,2,3,4-tetracarboxylic acid or of pyromellitic acid.

A divalent radical of a dicarbamic acid as G may be, for example, the hexamethylenedicarbamic acid radical or the 2,4-toluylenedicarbamic acid radical.

Preferred compounds are compounds (IA), in which n is 1 or 2, $R_1'$, $R_2'$ and $R_3'$ are each hydrogen and $R_a$ is $C_2$–$C_{18}$alkanoyl or $C_3$–$C_6$alkenoyl and G is the acyl radical of an aliphatic monocarboxylic acid having from 12 to 18 C-atoms or the diacyl radical of an aliphatic dicarboxylic acid having from 4 to 12 C-atoms.

Further sterically hindered amine derivatives are compounds of the formula:

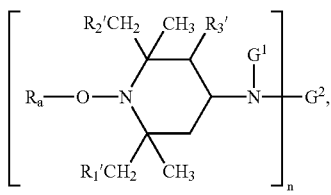

(IB)

where n is 1 or 2 and $R_a$, $R_1'$, $R_2'$ and $R_3'$ are as defined under the formula IA;

$G^1$ is hydrogen, $C_1$–$C_{12}$alkyl, $C_2$–$C_5$hydroxyalkyl, $C_5$–$C_7$cycloalkyl, $C_7$–$C_8$aralkyl, $C_2$–$C_{18}$alkanoyl, $C_3$–$C_5$alkenoyl or benzoyl or a group:

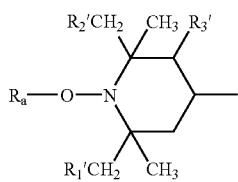

where $R_a$, $R_1'$, $R_2'$ and $R_3'$ are as defined above; and $G^2$ has the following meanings:

when n=1,
  hydrogen, $C_1$–$C_{18}$alkyl, $C_3$–$C_8$alkenyl, $C_5$–$C_7$cycloalkyl, $C_1$–$C_4$alkyl which bears a hydroxy, cyano, alkoxycarbonyl or carbamido group as substituent, glycidyl or a group —CH$_2$—CH(OH)-Z or CONH-Z, where Z is hydrogen, methyl or phenyl; or when n=2,
  $C_2$–$C_{12}$alkylene, $C_6$–$C_{12}$arylene, xylylene or —CH$_2$CH(OH)—CH$_2$— or —CH$_2$—CH(OH)—CH$_2$—O-D-O— group, where D is $C_2$–$C_{10}$alkylene, $C_6$–$C_{15}$arylene, $C_6$–$C_{12}$cycloalkylene;

or, provided that $G^1$ is not alkanoyl, alkenoyl or benzoyl, $G^2$ may also be 1-oxo-$C_2$–$C_{12}$alkylene, the divalent radical of an aliphatic, cycloaliphatic or aromatic dicarboxylic acid or dicarbamic acid or the —CO— group;

or, when n=1, $G^1$ and $G^2$ may together be the divalent radical of an aliphatic, cycloaliphatic or aromatic 1,2-dicarboxylic acid or 1,3-dicarboxylic acid.

$C_1$–$C_{12}$Alkyl and $C_1$–$C_{18}$alkyl substituents are as defined above under the formula (IA).

$C_5$–$C_7$Cycloalkyl is preferably cyclohexyl.

A $C_7$–$C_8$aralkyl group $G^1$ is preferably 2-phenylethyl or benzyl.

A $C_2$–$C_5$hydroxyalkyl group $G^1$ is preferably 2-hydroxyethyl or 2- or 3-hydroxypropyl.

A $C_2$–$C_{18}$alkanoyl group $G^1$ may be, for example, propionyl, butyryl, octanoyl, dodecanoyl, hexadecanoyl, octadecanoyl, preferably acetyl.

A $C_3$–$C_5$alkenoyl group $G^1$ is preferably acryloyl.

A $C_2$–$C_8$alkenyl group $G^2$ may be, for example, allyl, methallyl, 2-butenyl, 2-pentenyl, 2-hexenyl or 2-octenyl.

A hydroxy-, cyano-, alkoxycarbonyl- or carbamido-substituted $C_1$–$C_4$alkyl group $G^2$ may be, for example, 2-hydroxyethyl, 2-hydroxypropyl, 2-cyanoethyl, methoxycarbonylmethyl, 2-ethoxycarbonylethyl, 2-aminocarbonylpropyl or 2-(dimethylaminocarbonyl) ethyl.

A $C_2$–$C_{12}$alkylene group $G^2$ may be, for example, ethylene, propylene, 2,2-dimethylpropylene, tetramethylene, hexamethylene, octamethylene, decamethylene or dodecamethylene.

A $C_6$–$C_{15}$arylene group $G^2$ may be, for example, o-, m- or p-phenylene, 1,4-naphthylene or 4,4'-biphenylene.

A $C_6$–$C_{12}$-cycloalkylene group $G^2$ is preferably cyclohexylene.

Further sterically hindered amine derivatives are compounds of the formula:

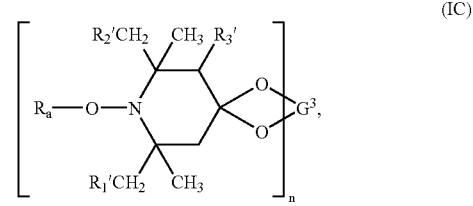

(IC)

where n is 1 or 2 and $R_a$, $R_1'$, $R_2'$ and $R_3'$ are as defined under the formula IA; and $G^3$ is $C_2$–$C_8$alkylene, $C_2$–$C_8$hydroxyalkylene or $C_4$–$C_{22}$acyloxyalkylene when n=1 or is the group (—CH$_2$)$_2$C(CH$_2$—)$_2$ when n=2.

A $C_2$–$C_8$alkylene or $C_2$–$C_8$hydroxyalkylene group $G^3$ may be, for example, ethylene, 1-methylethylene, propylene, 2-ethylpropylene or 2-ethyl-2-hydroxymethylpropylene.

A $C_4$–$C_{22}$-acyloxyalkylene group $G^3$ may be, for example, 2-ethyl-2-acetoxymethylpropylene.

Further sterically hindered amine derivatives are compounds of the formulae:

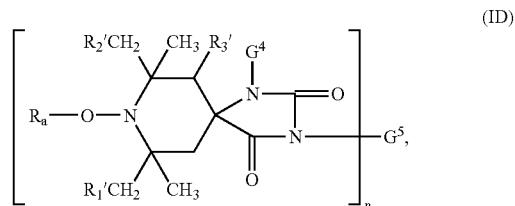

(ID)

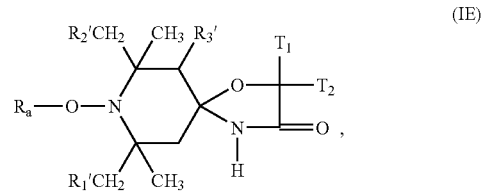

(IE)

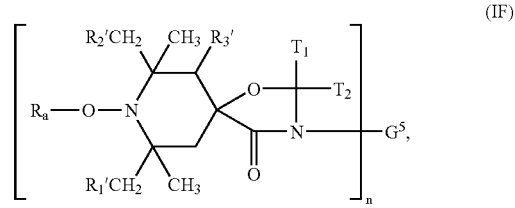

(IF)

where n is 1 or 2 and $R_a$, $R_1'$, $R_2'$ and $R_3'$ are as defined under the formula IA; and $G^4$ is hydrogen, $C_1$–$C_{12}$alkyl, allyl, benzyl, glycidyl or $C_2$–$C_6$alkoxyalkyl; and $G^5$ has the following meanings:
when n=1,
hydrogen, $C_1$–$C_{12}$alkyl, $C_3$–$C_5$alkenyl, $C_7$–$C_9$aralkyl, $C_5$–$C_7$cycloalkyl, $C_2$–$C_4$hydroxyalkyl, $C_2$–$C_6$alkoxyalkyl, $C_6$–$C_{10}$aryl, glycidyl or a group: —($CH_2$)$_p$—COO-Q or —($CH_2$)P—O—CO-Q, where p is 1 or 2 and Q is $C_1$–$C_4$alkyl or phenyl; or
when n=2,
$C_2$–$C_{12}$alkylene, $C_4$–$C_{12}$alkenylene, $C_6$–$C_{12}$arylene, the group —$CH_2$—CH(OH)—$CH_2$—O-D-O—$CH_2$—CH(OH)—$CH_2$—, where D is $C_2$–$C_{10}$-alkylene, $C_6$–$C_{15}$arylene or $C_6$–$C_{12}$-cycloalkylene, or the group —$CH_2$CH(OZ')$CH_2$—(O$CH_2$—CH(OZ')$CH_2$)$_2$—,
where Z' is hydrogen, $C_1$–$C_{18}$alkyl, allyl, benzyl, $C_2$–$C_{12}$-alkanoyl or benzoyl.

$T^1$ and $T^2$ are each, independently of one another, hydrogen, $C_1$–$C_{18}$alkyl, $C_6$–$C_{10}$aryl or $C_7$–$C_9$aralkyl, each of which may be substituted by halogen or $C_1$–$C_4$-alkyl, or $T^1$ and $T^2$ together with the carbon atom connecting them form a $C_5$–$C_{14}$cycloalkane ring.

The substituents $C_1$–$C_{12}$alkyl are, for example, methyl, ethyl, n-propyl, isopropyl, n-butyl, sec-butyl, tert-butyl, n-hexyl, n-octyl, 2-ethylhexyl, n-nonyl, n-decyl, n-undecyl or n-dodecyl.

Substituents defined as $C_1$–$C_{18}$-alkyl may be, for example, the abovementioned groups or, for example, n-tridecyl, n-tetradecyl, n-hexadecyl or n-octadecyl.

$C_2$–$C_6$Alkoxyalkyl is, for example, methoxymethyl, ethoxymethyl, propoxymethyl, tert-butoxymethyl, 2-ethoxyethyl, 2- or 3-ethoxy-n-propyl, 2-n-butoxyethyl, 2-tert-butoxyethyl, 2-isopropoxyethyl or 2- or 3-n-propoxy-n-propyl.

A $C_3$–$C_5$alkenyl group $G^5$ may be, for example, 1-propenyl, allyl, methallyl, 2-butenyl or 2-pentenyl.

$C_7$–$C_9$Aralkyl groups $G^5$, $T^1$ and $T^2$ are preferably 2-phenethyl or benzyl. When $T^1$ and $T^2$ together with the carbon atom form a cycloalkane ring, this ring may be, for example, a cyclopentane, cyclohexane, cyclooctane or cyclododecane ring.

A $C_2$–$C_4$hydroxyalkyl group $G^5$ may be, for example, 2-hydroxyethyl, 2- or 3-hydroxy-n-propyl or 2-, 3- or 4-hydroxy-n-butyl.

A $C_6$–$C_{10}$aryl group $G^5$, $T^1$ and $T^2$ is preferably phenyl or α- or β-naphthyl, each of which may be substituted by halogen or $C_1$–$C_4$alkyl.

A $C_2$–$C_{12}$alkylene group $G^5$ may be, for example, ethylene, propylene, 2,2-dimethylpropylene, tetramethylene, hexamethylene, octamethylene, decamethylene or dodecamethylene.

A $C_4$–$C_{12}$alkenylene group $G^5$ is preferably 2-butenylene, 2-pentenylene or 3-hexenylene.

A $C_6$–$C_{12}$arylene group $G^5$ may be, for example, o-, m- or p-phenylene, 1,4-naphthylene or 4,4'-biphenylene.

A $C_{2-12}$alkanoyl group Z' is, for example, preferably acetyl and may also be propionyl, butyryl, n-octanoyl or n-dodecanoyl.

$C_2$–$C_{10}$Alkylene, $C_6$–$C_{15}$arylene and $C_6$–$C_{12}$cycloalkylene groups D are as defined under formula IB.

Further sterically hindered amine derivatives are compounds of the formula:

(IG)

where n=1 or 2 and $G^6$ is a group:

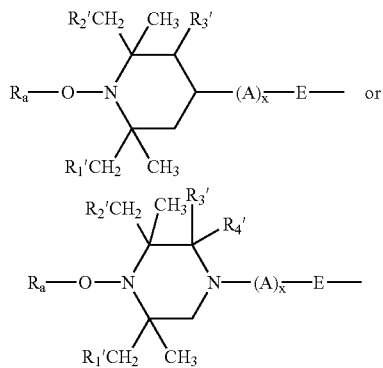

where $R_a$, $R_1'$, $R_2'$ and $R_3'$ are as defined under the formula IA, and $R_3'$ and $R_4'$ are each hydrogen or methyl or together form the substituent =O;

E is —O— or —N$G^1$-, where G' is as defined under the formula IB;

A is $C_2$–$C_6$-alkylene or —($CH_2$)$_3$—O—, and x is either 0 or 1;

$G^1$ is preferably hydrogen, $C_1$–$C_{12}$alkyl, $C_2$–$C_5$hydroxyalkyl or $C_5$–$C_7$cycloalkyl;

$G^7$ is identical to $G^6$ or is one of the groups —N$G^9G^{10}$, —O$G^{11}$, —NHCH$_2$O$G^{11}$ or —N(CH$_2$O$G^{11}$)$_2$;

when n=1, $G^8$ is identical to $G^6$ or $G^7$; and, when n=2, $G^8$ is the group -E-B-E-, where B is $C_2$–$C_8$-alkylene or $C_2$–$C_8$-alkylene interrupted by 1 or 2 —N$G^9$-groups, and $G^9$ is $C_1$–$C_{12}$alkyl, cyclohexyl, benzyl or $C_1$–$C_4$hydroxyalkyl or groups:

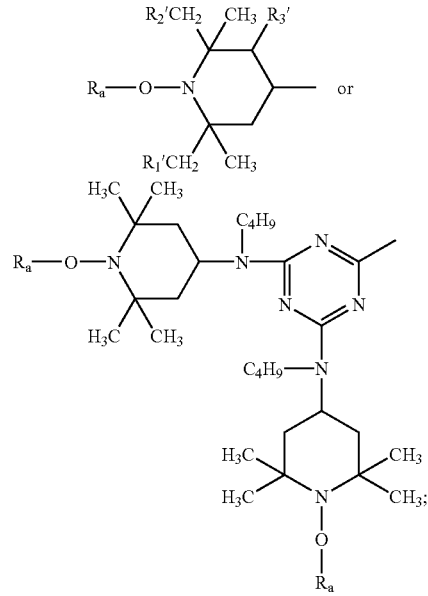

$G^{10}$ is $C_1$–$C_{12}$-alkyl, cyclohexyl, benzyl or $C_1$–$C_4$-hydroxyalkyl, and $G^{11}$ is hydrogen, $C_1$–$C_{12}$-alkyl or phenyl; and $G^9$ and $G^{10}$ are together, for example, $C_4$–$C_5$-alkylene, $C_4$–$C_5$oxaalkylene, e.g. tetramethylene, pentamethylene or 3-oxapentamethylene, or the corresponding $C_4$–$C_5$thiaalkylene, e.g. the group

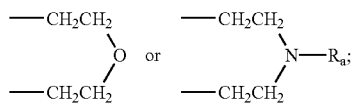

$C_1$–$C_{12}$Alkyl is, for example, methyl, ethyl, n-propyl, n-butyl, sec-butyl, tert-butyl, n-hexyl, n-octyl, 2-ethylhexyl, n-nonyl, n-decyl, n-undecyl or n-dodecyl.

$C_1$–$C_4$Hydroxyalkyl is, for example, 2-hydroxyethyl, 2- or 3-hydroxypropyl or 2-, 3- or 4-hydroxy-n-butyl.

A $C_2$–$C_6$alkylene group A, may be, for example, ethylene, propylene, 2,2-dimethylpropylene, tetramethylene or hexamethylene.

Polyesters (I) are, for example, compounds of the formula:

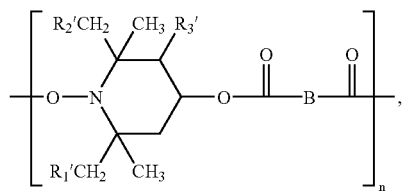

(IH)

where n is an integer greater than two and $R_1'$, $R_2'$ and $R_3'$ are as defined under the formula IA; and B is a bivalent substituent, e.g. $C_1$–$C_{12}$alkylene, e.g. methylene, ethylene, propylene, 2,2-dimethylpropylene or tetramethylene, hexamethylene, octamethylene, decamethylene or dodecamethylene, $C_6$–$C_{15}$arylene, e.g. a group:

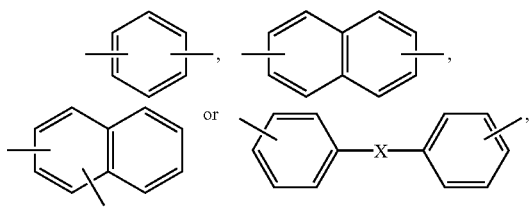

where X is a bivalent substituent, e.g. $C_1$–$C_{12}$alkylene as defined above, —O—, —(C=O)—, —S— or —S(=O)$_2$—.

Polyesters of compounds of the formula I may also be, for example, copolymers of polyesters (IH) in which the group:

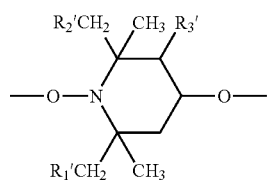

is partially replaced by suitable diols, which are derived, for example, from aliphatic, cycloaliphatic or aromatic diols.

The aliphatic diols may contain from 2 to 12 C-atoms, the cycloaliphatic diols may contain from 5 to 8 C-atoms and the aromatic diols may contain from 6 to 15 C-atoms.

Polyoxyalkylene glycols having molecular weights in the range from 150 to 40 000 are also possible.

Aromatic diols are compounds in which two hydroxy groups are bound to an aromatic hydrocarbon radical or to different aromatic hydrocarbon radicals.

It is also possible for the polyesters to be branched by means of small amounts, e.g. from 0.1 to 3 mol %, based on the dicarboxylic acids present, of more than bifunctional monomers (e.g. pentaerythritol, trimellitic acid, 1,3,5-tri(hydroxyphenyl)benzene, 2,4-dihydroxybenzoic acid or 2-(4-hydroxyphenyl)-2-(2,4-dihydroxyphenyl)propane).

Suitable aliphatic diols are linear and branched aliphatic glycols, in particular those having from 2 to 12, preferably from 2 to 6, C-atoms in the molecule, e.g. ethylene glycol, 1,2- and 1,3-propylene glycol, 1,2-, 1,3-, 2,3- or 1,4-butanediol, pentyl glycol, neopentyl glycol, 1,6-hexanediol, 1,12-dodecanediol.

A suitable cycloaliphatic diol is, for example, 1,4-dihydroxycyclohexane. Further suitable diols are, for example, 1,4-bis(hydroxymethyl)cyclohexane, aromatic-aliphatic diols such as p-xylylene glycol or 2,5-dichloro-p-xylylene glycol, 2,2-(β-hydroxyethoxyphenyl)propane and also polyoxyalkylene glycols such as diethylene glycol, triethylene glycol, polyethylene glycol or polypropylene glycol. The alkylenediols are preferably linear and contain, in particular, from 2 to 4 C-atoms.

Preferred diols are alkylene diols, 1,4-dihydroxycyclohexane and 1,4-bis(hydroxymethyl)cyclohexane. Particular preference is given to ethylene glycol, 1,4-butanediol and 1,2- and 1,3-propylene glycol.

Further suitable aliphatic diols are the β-hydroxyalkylated, in particular β-hydroxyethylated, bisphenols such as 2,2-bis[4'-(β-hydroxyethoxy)phenyl]propane.

A further group of suitable aliphatic diols consists of the heterocyclic diols described in DE-A 1,812,003, 2,342,432, 2,342,372 and 2,453,326. Examples are: N,N'-bis(p-hydroxyethyl)-5,5-dimethylhydantoin, N,N'-bis(β-hydroxypropyl)-5,5-dimethylhydantoin, methylenebis[N-(β-hydroxyethyl)-5-methyl-5-ethylhydantoin], methylenebis[N-(β-hydroxyethyl)-5,5-dimethylhydantoin], N,N'-bis(β-hydroxyethyl)benzimidazolone, N,N'-bis(β-hydroxyethyl)(tetrachloro)benzimidazolone or N,N'-bis(β-hydroxyethyl)(tetrabromo)benzimidazolone.

Suitable aromatic diols are diphenols having one aromatic unit, in particular diols having two aromatic units which bear a hydroxy group on each aromatic unit. Aromatic units are to be understood as meaning aromatic hydrocarbon radicals such as phenylene or naphthylene. Apart from, for example, hydroquinone, resorcinol or 1,5-, 2,6- and 2,7-dihydroxynaphthalene, particular mention may be made of bisphenols which can be represented by the following formulae:

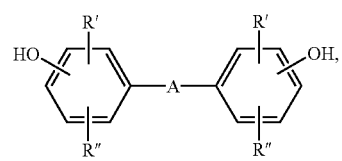

-continued

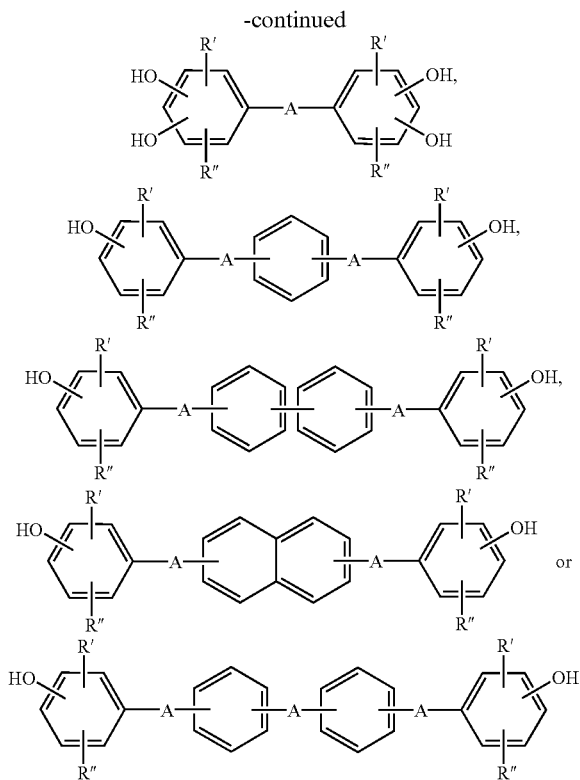

The hydroxy groups can be located in the m-position, but particularly in the p-position; R' and R" in these formulae can be alkyl having from 1 to 6 C-atoms, halogen such as chlorine or bromine and in particular hydrogen atoms. A can be a direct bond or —O—, —S—, —S(=O)$_2$—, —C(=O)—, —[P(=O)C$_1$-C$_{20}$-alkyl]-, substituted or unsubstituted alkylidene, cycloalkylidene or alkylene.

Examples of substituted or unsubstituted alkylidene are: ethylidene, 1,1- or 2,2-propylidene, 2,2-butylidene, 1,1-isobutylidene, pentylidene, hexylidene, heptylidene, octylidene, dichloroethylidene, trichlorethylidene.

Examples of substituted or unsubstituted alkylene are methylene, ethylene, phenylmethylene, diphenylmethylene and methylphenylmethylene. Examples of cycloalkylidene are cyclopentylidene, cyclohexylidene, cycloheptylidene and cyclooctylidene.

Examples of bisphenols are: bis(p-hydroxyphenyl) ether or thioether, bis(p-hydroxyphenyl) sulfone, bis(p-hydroxyphenyl)methane, 2,2'-bis(4-hydroxyphenyl)biphenyl, phenylhydroquinone, 1,2-bis(p-hydroxyphenyl)ethane, 1-phenylbis(p-hydroxyphenyl)methane, diphenylbis(p-hydroxyphenyl)methane, diphenylbis(p-hydroxyphenyl) ethane, bis(3,5-dimethyl-4-hydroxyphenyl) sulfone, bis(3,5-dimethyl-4-hydroxyphenyl)-p-diisopropylbenzene, bis(3,5-dimethyl-4-hydroxyphenyl)-m-diisopropylbenzene, 2,2-bis(3',5'-dimethyl-4'-hydroxyphenyl)propane, 1,1- or 2,2-bis(p-hydroxyphenyl)butane, 2,2-bis(p-hydroxyphenyl) hexafluoropropane, 1,1-dichloro- or 1,1,1-trichloro-2,2-bis (p-hydroxyphenyl)ethane, 1,1-bis(p-hydroxyphenyl) cyclopentane and in particular 2,2-bis(p-hydroxyphenyl) propane (bisphenol A) and 1,1-bis(p-hydroxyphenyl) cyclohexane (bisphenol C).

Polyesteramides of compounds of the formula I are, for example, compounds of the formula:

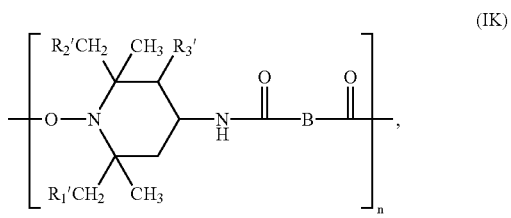

where n is a number greater than two and R$_1$', R$_2$' and R$_3$' are as defined under the formula IA; and B is a bivalent substituent having the meanings specified under the formula IH.

Polyesteramides of compounds of the formula I also include, for example, copolymers in which the group:

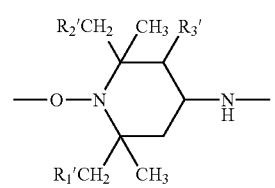

is partially replaced by the abovementioned diols or by suitable diamines derived, for example, by the abovementioned aliphatic, cycloaliphatic or aromatic diols by replacement of the hydroxy groups by amino.

Polyurethanes of compounds of the formula I are, for example, compounds of the formula:

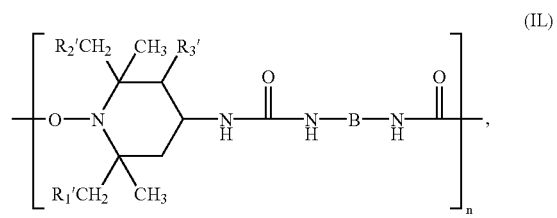

where n is an integer greater than two and R$_1$', R$_2$' and R$_3$' are as defined under the formula IA; and B is a bivalent substituent having the meanings specified under the formula IH.

Polyurethanes of compounds of the formula I also include, for example, copolymers in which the group

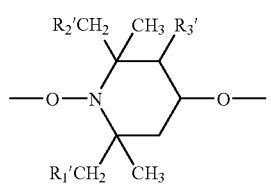

is partially replaced by suitable diols, e.g. the abovementioned diols, or diamines derived, for example, from the abovementioned aliphatic, cycloaliphatic or aromatic diols by replacement of the hydroxy groups by amino.

Polyurethanes can be prepared in a manner known per se by reacting the abovementioned cyclic hydroxylamines having a hydroxy group in the 4-position with dicarboxylic acids in which the carboxy groups are replaced by isocyanate groups.

Polycarbonates of compounds of the formula I are, for example, compounds of the formula:

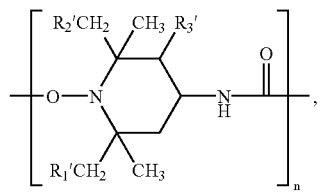
(IM)

where n is an integer greater than two and $R_1'$, $R_2'$ and $R_3'$ are as defined in the formula IA. Polycarbonates can be prepared in a manner known per se by reacting the abovementioned cyclic hydroxylamines having a hydroxy group in the 4-position with phosgene or a carbonic ester, e.g. diethyl carbonate or diphenyl carbonate.

Polyurethanes of compounds of the formula I also include, for example, copolymers in which the group

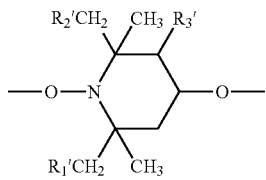

is partially replaced by suitable diols, e.g. the abovementioned diols.

Polyimide esters of compounds of the formula I are, for example, compounds of the formula:

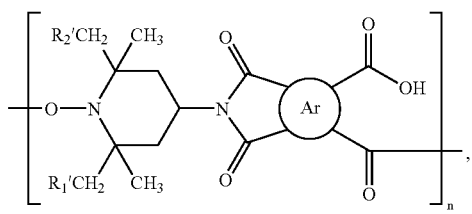
(IN)

where n is an integer greater than two and $R_1'$, $R_2'$ and $R_3'$ are as defined under the formula IA. The aromatic connecting unit has, for example, one of the following structures:

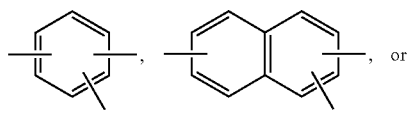, or

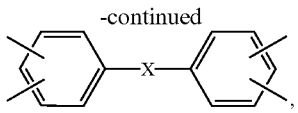, where X is, for example, —O—, —C(=O)—, —S—, —S(=O)$_2$— or $C_1$–$C_4$alkylene. Polyimide esters can be prepared in a manner known per se by reacting the above-described cyclic hydroxylamines with a tetracarboxylic anhydride.

The invention provides, in particular, a process for reducing the molecular weight of polypropylene, propylene copolymers or polypropylene blends, characterised in that at least one compound of the formula Ia, where $R_a$ is an acyl radical selected from the group consisting of —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl, —C(=O)—N($C_1$–$C_6$alkyl)$_2$, —P(=O)—$C_1$–$C_{19}$alkyl, —P(=O)$_2$—$C_1$–$C_{19}$alkyl, —P(=O)—$C_6$–$C_{10}$aryl, —P=O(—$C_1$–$C_{19}$alkyl)$_2$, —P=O(—$C_6$–$C_{10}$aryl)$_2$, —P(=O)—O—$C_1$–$C_6$alkyl, —P(=O)—O—$C_6$–$C_{10}$aryl, —P=O(—O—$C_1$–$C_6$alkyl)$_2$, —P=O(—O—$C_6$–$C_{10}$aryl)$_2$, —P(—O—$C_1$–$C_6$alkyl)$_2$ and —P(—O—$C_6$–$C_{10}$aryl)$_2$;

$R_1$–$R_4$ are each $C_1$–$C_6$alkyl;

$R_5$ and $R_6$ are each, independently of one another, hydrogen, $C_1$–$C_6$alkyl or $C_6$–$C_{10}$aryl; or $R_5$ and $R_6$ are together oxygen;

Q is a direct bond or a bivalent radical —(CR$_7$R$_8$)— or —(CR$_7$R$_8$—CR$_9$R$_{10}$)—, where $R_7$, $R_8$, $R_9$ and $R_{10}$ are each, independently of one another, hydrogen or $C_1$–$C_6$alkyl; and $Z_1$ is oxygen or a bivalent radical —NR$_{11}$— or —(CR$_{12}$R$_{13}$)—, where $R_{11}$ is hydrogen, $C_1$–$C_6$alkyl, $C_6$–$C_{10}$aryl or the acyl radical $R_a$ as defined above; or, independently of one another, $R_{12}$ and $R_{13}$ are each hydrogen or $C_1$–$C_6$alkyl, or one of the radicals $R_{12}$ and $R_{13}$ is hydrogen or $C_1$–$C_6$alkyl and the other is $C_1$–$C_6$alkyl, $C_1$–$C_6$alkoxy, $C_6$–$C_{10}$aryloxy, acyloxy selected from the group consisting of —O—C(=O)—H, —O—C(=O)—$C_1$–$C_{19}$alkyl, —O—C(=O)—$C_1$–$C_{54}$alkenyl, —O—C(=O)—$C_6$–$C_{10}$aryl, —O—C(=O)—$C_1$–$C_{36}$alkenyl-$C_6$–$C_{10}$aryl, —O—C(=O)—O—$C_1$–$C_6$alkyl, —O—C(=O)—O—$C_6$–$C_{10}$aryl, —O—C(=O)—NH—$C_1$–$C_6$alkyl, —O—C(=O)—NH—$C_6$–$C_{10}$aryl and —O—C(=O)—N($C_1$–$C_6$alkyl)$_2$, $C_1$–$C_6$alkylamino, di-$C_1$–$C_6$alkylamino, $C_6$–$C_{10}$arylamino, acylamino selected from the group consisting of —NH—C(=O)—H, —NH—C(=O)—$C_1$–$C_{19}$alkyl, —NH—C(=O)—$C_1$–$C_{54}$alkenyl, —NH—C(=O)—$C_6$–$C_{10}$aryl, —NH—C(=O)—$C_1$–$C_{36}$alkenyl-$C_6$–$C_{10}$aryl, —NH—C(=O)—O—$C_1$–$C_{19}$alkyl, —NH—C(=O)—O—$C_6$–$C_{10}$aryl, —NH—C(=O)—NH—$C_1$–$C_6$alkyl, —NH—C(=O)—NH—$C_6$–$C_{10}$aryl and —NH—C(=O)—N($C_1$–$C_6$alkyl)$_2$, diacylamino selected from the group consisting of —N[—C(=O)—$C_1$–$C_{19}$alkyl]$_2$, —N[—C(=O)—$C_6$–$C_{10}$aryl]$_2$, —N[—C(=O)—$C_1$–$C_6$alkylene-C(=O)—], —N[—C(=O)—

$C_2$–$C_6$alkenylene-C(=O)—] and phthalimido or N-acyl-N—$C_1$–$C_6$alkylamino;

or the two radicals $R_{12}$ and $R_{13}$ are together oxo; or a compound of the formula Ib, where
$R_a$ is an acyl radical selected from the group consisting of —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl and —C(=O)—N($C_1$–$C_6$alkyl)$_2$;

$R_1$–$R_4$ are each $C_1$–$C_6$alkyl;

A are substituents on the phenyl rings; and m is an integer from one to four; or a compound of the formula Ic, where
$R_a$ is an acyl radical selected from the group consisting of —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl, —C(=O)—N($C_1$–$C_6$alkyl)$_2$, —P(=O)—$C_1$–$C_{19}$alkyl, —P(=O)$_2$—$C_1$–$C_{19}$alkyl, —P(=O)—$C_6$–$C_{10}$aryl, —P=O(—$C_1$–$C_{19}$alkyl)$_2$, —P=O(—$C_6$–$C_{10}$aryl)$_2$, —P(=O)—O—$C_1$–$C_6$alkyl, —P(=O)—O—$C_6$–$C_{10}$aryl, —P=O(—O—$C_1$–$C_6$alkyl)$_2$, —P=O(—O—$C_6$–$C_{10}$aryl)$_2$, —P(—O—$C_1$–$C_6$alkyl)$_2$ and —P(—O—$C_6$–$C_{10}$aryl)$_2$;

$R_b$ is hydrogen, carbamoyl, $C_1$–$C_6$alkylcarbamoyl, di-$C_1$–$C_6$alkylcarbamoyl or is as defined for $R_a$;

$R_c$ and $R_d$ are each, independently of one another, hydrogen, $C_1$–$C_{20}$alkyl or $C_6$–$C_{10}$aryl; and $R_1$–$R_3$ are each $C_1$–$C_6$alkyl or $C_6$–$C_{10}$aryl; or a compound of the formula:

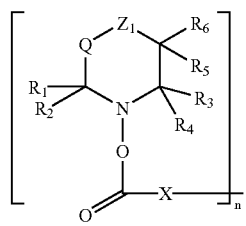

(Id)

where, n is two;

X is a direct bond or the monovalent radical of a $C_1$–$C_{18}$alkylene bridge;

$R_1$–$R_4$ are each $C_1$–$C_6$alkyl;

$R_5$ and $R_6$ are each, independently of one another, hydrogen, $C_1$–$C_6$alkyl or $C_6$–$C_{10}$aryl; or $R_5$ and $R_6$ are together oxygen;

Q is a direct bond or a bivalent radical —(CR$_7$R$_8$)— or —(CR$_7$R$_8$—CR$_9$R$_{10}$)—, where $R_7$, $R_8$, $R_9$ and $R_{10}$ are each, independently of one another, hydrogen or $C_1$–$C_6$alkyl; and $Z_1$ is oxygen or a bivalent radical —NR$_{11}$— or —(CR$_{12}$R$_{13}$)—, where $R_{11}$ is hydrogen, $C_6$–$C_{10}$aryl or $C_1$–$C_6$alkyl or, independently of one another, one of the radicals $R_{12}$ and $R_{13}$ is hydrogen or $C_1$–$C_6$alkyl and the other is $C_1$–$C_6$alkyl, $C_1$–$C_6$alkoxy, $C_6$–$C_{10}$aryloxy, acyloxy selected from the group consisting of —O—C(=O)—H, —O—C(=O)—$C_1$–$C_{19}$alkyl, —O—C(=O)—$C_1$–$C_{54}$alkenyl, —O—C(=O)—$C_6$–$C_{10}$aryl, —O—C(=O)—$C_1$–$C_{36}$alkenyl-$C_6$–$C_{10}$aryl, —O—C(=O)—O—$C_1$–$C_6$alkyl, —O—C(=O)—O—$C_6$–$C_{10}$aryl, —O—C(=O)—NH—$C_1$–$C_6$alkyl, —O—C(=O)—NH—$C_6$–$C_{10}$aryl and —O—C(=O)—N($C_1$–$C_6$alkyl)$_2$, $C_1$–$C_6$alkylamino, di-$C_1$–$C_6$alkylamino, $C_6$–$C_{10}$arylamino, acylamino selected from the group consisting of —NH—C(=O)—H, —NH—C(=O)—$C_1$–$C_{19}$alkyl, —NH—C(=O)—$C_1$–$C_{54}$alkenyl, —NH—C(=O)—$C_6$–$C_{10}$aryl, —NH—C(=O)—$C_1$–$C_{36}$alkenyl-$C_6$–$C_{10}$aryl, —NH—C(=O)—O—$C_1$–$C_{19}$alkyl, —NH—C(=O)—O—$C_6$–$C_{10}$aryl, —NH—C(=O)—NH—$C_1$–$C_6$alkyl, —NH—C(=O)—NH—$C_6$–$C_{10}$aryl and —NH—C(=O)—N($C_1$–$C_6$alkyl)$_2$, diacylamino selected from the group consisting of —N[—C(=O)—$C_1$–$C_{19}$alkyl]$_2$, —N[—C(=O)—$C_6$–$C_{10}$aryl]$_2$, —N[—C(=O)—$C_1$–$C_6$alkylene-C(=O)—], —N[—C(=O)—$C_2$–$C_6$alkenylene-C(=O)—] and phthalimido or N-acyl-N—$C_1$–$C_6$alkylamino;

or the two radicals $R_{12}$ and $R_{13}$ are together oxo; or a compound of the formula:

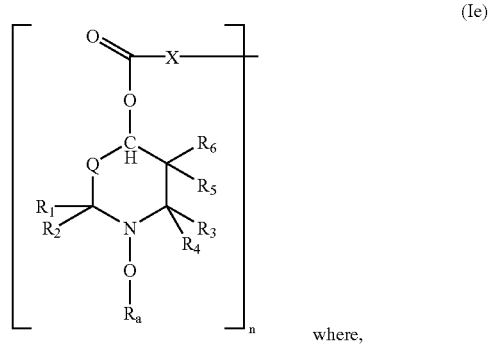

(Ie)

where, n is two $R_a$ is an acyl radical selected from the group consisting of —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl and —C(=O)—N($C_1$–$C_6$alkyl)$_2$;

X is a direct bond or the monovalent radical of a $C_1$–$C_{18}$alkylene bridge;

$R_1$–$R_4$ are each $C_1$–$C_6$alkyl;

$R_5$ and $R_6$ are each, independently of one another, hydrogen $C_1$–$C_6$alkyl or $C_6$–$C_{10}$aryl; or $R_5$ and $R_6$ are together oxygen; and Q is a direct bond or a bivalent radical —(CR$_7$R$_8$)— or —(CR$_7$R$_8$—CR$_9$R$_{10}$)—, where $R_7$, $R_8$, $R_9$ and $R_{10}$ are each, independently of one another, hydrogen or $C_1$–$C_6$alkyl;

is added to the polypropylene, polypropylene copolymer or polypropylene blend to be degraded and the mixture is heated.

The formula Id) represents bicyclic compounds in which the two halves are joined by the bivalent bridge X. When X is a direct bond, the bicyclic compound has the formula

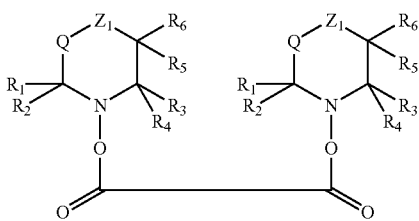

This compound is a hydroxylamine diester of oxalic acid. When X is the monovalent radical of a $C_1$–$C_{18}$alkylene bridge, the bicyclic compound is a hydroxylamine diester of a malonic acid, succinic acid or a higher dicarboxylic acid.

$R_1$–$R_4$ are as defined above.

Likewise, $R_5$, $R_6$, Q, $R_7$, $R_8$, $R_9$ and $R_{10}$ are as defined above.

$Z_1$ may be oxygen or a bivalent radical —$NR_{11}$— or —($CR_{12}R_{13}$)—, where $R_{11}$ is hydrogen, aryl, $C_1$–$C_6$alyl or, independently of one another, one of the radicals $R_{12}$ and $R_{13}$ is hydrogen or $C_1$–$C_6$alkyl and the other is $C_1$–$C_6$alkyl, $C_1$–$C_6$alkoxy, $C_6$–$C_{10}$aryloxy, acyloxy selected from the group consisting of —O—C(=O)—H, —O—C(=O)—$C_1$–$C_{19}$alkyl, —O—C(=O)—$C_1$–$C_{54}$alkenyl, —O—C(=O)—$C_6$–$C_{10}$aryl, —O—C(=O)—$C_1$–$C_{36}$alkenyl-$C_6$–$C_{10}$aryl, —O—C(=O)—O—$C_1$–$C_{19}$alkyl, —O—C(=O)—O—$C_6$–$C_{10}$aryl, —O—C(=O)—NH—$C_1$–$C_6$alkyl, —O—C(=O)—NH—$C_6$–$C_{10}$aryl and —O—C(=O)—N($C_1$–$C_6$alkyl)$_2$, $C_1$–$C_6$alkylamino, di-$C_1$–$C_6$alkylamino, $C_6$–$C_{10}$arylamino, acylamino selected from the group consisting of —NH—C(=O)—H, —NH—C(=O)—$C_1$–$C_{19}$alkyl, —NH—C(=O)—$C_1$–$C_{54}$alkenyl, —NH—C(=O)—$C_6$–$C_{10}$aryl, —NH—C(=O)—$C_1$–$C_{36}$alkenyl-$C_6$–$C_{10}$aryl, —NH—C(=O)—O—$C_1$–$C_{19}$alkyl, —NH—C(=O)—O—$C_6$–$C_{10}$aryl, —NH—C(=O)—NH—$C_1$–$C_6$alkyl, —NH—C(=O)—NH—$C_6$–$C_{10}$aryl and —NH—C(=O)—N($C_1$–$C_6$alkyl)$_2$, diacylamino selected from the group consisting of —N[—C(=b)—$C_1$–$C_{19}$alkyl]$_2$, —N[—C(=O)—$C_6$–$C_{10}$aryl]$_2$, —N[—C(=O)—$C_1$–$C_6$alkylene-C(=O)—], —N[—C(=O)—$C_2$–$C_6$alkenylene-C(=O)—] and phthalimido or N-acyl-N—$C_1$–$C_6$alkylamino as defined above; or the two radicals $R_{12}$ and $R_{13}$ are together oxo.

The addition to the propylene polymer can be carried out in all customary mixing machines in which the polymer is melted and mixed with the additives. Suitable machines are known to those skilled in the art. They are predominantly mixers, kneaders and extruders.

The process is preferably carried out in an extruder by introducing the additive during processing.

Particularly preferred processing machines are single-screw extruders, contrarotating and corotating twin-screw extruders, planetary-gear extruders, ring extruders or cokneaders. It is also possible to use processing machines provided with at least one gas removal compartment to which a vacuum can be applied.

Suitable extruders and kneaders are described, for example, in *Handbuch der Kunststoffextrusion, Vol. 1 Grundlagen*, Editors F. Hensen, W. Knappe, H. Potente, 1989, pp. 3–7, *ISBN*:3-446-14339-4 (*Vol. 2 Extrusionsanlagen* 1986, ISBN 3-446-14329-7).

For example, the screw length is 1–60 screw diameters, preferably 35–48 screw diameters. The rotational speed of the screw is preferably 10–600 rotations per minute (rpm), very particularly preferably 25–300 rpm.

The maximum throughput is dependent on the screw diameter, the rotational speed and the driving force. The process of the present invention can also be carried out at a level lower than maximum throughput by varying the parameters mentioned or employing weighing machines delivering dosage amounts.

If a plurality of components are added, these can be premixed or added individually.

The polymers need to be subjected to an elevated temperature for a sufficient period of time, so that the desired degradation occurs. The temperature is generally above the softening point of the polymers.

In a preferred embodiment of the process of the present invention, a temperature range lower than 280° C., particularly from about 160° C. to 280° C. is employed. In a particularly preferred process variant, the temperature range from about 200° C. to 270° C. is employed.

The period of time necessary for degradation can vary as a function of the temperature, the amount of material to be degraded and the type of, for example, extruder used. It is usually from about 10 seconds to 20 minutes, in particular from 20 seconds to 10 minutes.

The above-described hydroxylamine esters (I) are suitable for reducing the molecular weight of polypropylene, propylene copolymers and polypropylene blends during compounding, where they effect degradation of the polymer chains like the peroxides customarily used in the prior art.

In the process for reducing the molecular weight (degradation process), the above-described hydroxylamine esters (I) are present in concentrations, based on the amount of polymers to be degraded, of from about 0.001 to 5.0% by weight, in particular from 0.01 to 2.0% by weight and particularly preferably from 0.02 to 1.0% by weight. The hydroxylamine esters (I) can be added as individual compounds or as mixtures to the polymer to be degraded.

The polypropylene-type polymers to be degraded can encompass propylene homopolymers, propylene copolymers and polypropylene blends. Propylene copolymers may contain various proportions up to 90%, preferably up to 50%, of comonomers. Examples of comonomers are: olefins such as 1-olefins, e.g. ethylene, 1-butene, 1-pentene, 1-hexene, 1-heptene or 1-octene, isobutylene, cycloolefins, e.g. cyclopentene, cyclohexene, norbornene or ethylidenenorborne, dienes such as butadiene, isoprene, 1,4-hexadiene, cyclopentadiene, dicyclopentadiene or norbornadiene; also acrylic acid derivatives and unsaturated carboxylic arhydrides such as maleic anhydride.

Polypropylene blends which can be used are mixtures of polypropylene with polyolefins. Examples are blends of polypropylene with polyethylene selected from the group consisting of high density polyethylene (HDPE), high molecular weight high density polyethylene (HMW HDPE), ultra high molecular weight high density polyethylene (UHMW HDPE), medium density polyethylene (MDPE), low density polyethylene (LDPE), linear low density polyethylene (LLDPE), branched low density polyethylene (BLDPE) and ethylene-propylenediene terpolymers (EPDM) containing small proportions of diene.

While the sometimes volatile decomposition products (smoke) of peroxides can lead to discoloration or odour in the degraded polymers, very little discoloration and odour occur in the case of the polymers degraded by means of hydroxylamine esters (I).

Incorporation into the polymers can be carried out, for example, by mixing the above-described hydroxylamine esters (I) or mixtures thereof and, if desired, further additives into the polymers using the methods customary in process technology.

Incorporation can, alternatively, also be carried out at temperatures which do not yet cause decomposition of the polymers (latent compound). The polymers prepared in this way can subsequently be heated a second time and subjected to an elevated temperature for a sufficient period of time so that the desired polymer degradation occurs.

The NOR-compounds (I) can also be added to the polymers to be degraded in the form of a masterbatch in which these compounds are present, for example, in a concentration of from about 1 to 25% by weight. The masterbatch (concentrate) can be produced at temperatures which do not yet cause decomposition of the compounds of the present invention.

This provides a product which is defined by specific dosage amounts and may be compounded with other additives. The masterbatch can then be compounded with the polymer to be degraded at a temperature above the decomposition temperature of the hydroxylamine ester (I).

The present invention therefore further provides a concentrate in which the compounds of the invention are present in a concentration of 1–25% by weight and which can be added to the polymer to be degraded. The desired product is thus obtainable in an advantageous two-stage process.

In a specific embodiment, suitable additives, e.g. acidic earths, for example of the type Fulcat®, zeolites, hydrotalcites or metal salts, e.g. of Ca, Fe, Zn or Cu, are added to the polymers to be degraded.

It has surprisingly been found that oxides, hydroxides and carbonates of metals in the oxidation state 11 aid the degrading action. Preference is therefore given to compositions which, in addition to the above-described NOR-compounds (I), further comprise 0.1–10 parts of metal salt per part of NOR-compound (I). Particular preference is given to concentrations of 0.5–10 parts of metal salt selected from the group consisting of CaO, $CaCO_3$, ZnO, $ZnCO_3$, MgO, $MgCO_3$ or $Mg(OH)_2$ per part of NOR-compound (I).

Apart from the hydroxylamine esters, further additives can also be present in the polymer, e.g. light stabilizers of the 2-(2-hydroxyphenyl)-1,3,5-triazine type which are known from the patent literature, e.g. U.S. Pat. No. 4,619,956, EP-A-434 608, U.S. Pat. No. 5,198,498, U.S. Pat. No. 5,322,868, U.S. Pat. No. 5,369,140, U.S. Pat. No. 5,298,067, WO-94/18278, EP-A-704 437, GB-A-2,297,091 or WO-96/28431.

Further examples of additives are given below:

1. Antioxidants
1.1. Alkylated monophenols, e.g. 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which may be linear or branched in the side chain, e.g. 2,6-dinonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.
1.2. Alkylthiomethylphenols, e.g. 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol.
1.3. Hydroquinones and alkylated hydroquinones, e.g. 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.
1.4. Tocopherols, e.g. α-, β-, γ- and δ-tocopherol.
1.5. Hydroxylated diphenyl thioethers, e.g. bis(3-tert-butyl-5-methyl-2-hydroxyphenyl) thioether, bis(5-octyl-2-hydroxyphenyl) thioether, bis(5-tert-butyl-2-methyl-4-hydroxyphenyl) thioether, bis(5-tert-butyl-3-methyl-4-hydroxyphenyl) thioether, bis(2,5-di-sec-amyl-4-hydroxyphenyl) thioether, bis(2,6-dimethyl-4-hydroxyphenyl) disulfide.
1.6. Alkylidene bisphenols, e.g. 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl] terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.
1.7. O-, N- and S-Benzyl compounds, e.g. bis(3,5-di-tert-butyl-4-hydroxybenzyl) ether, octadecyl 4-hydroxy-3,5-dimethylbenzylmercaptoacetate, tridecyl 4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl) dithioterephthalate, bis(3,5-di-tert-butyl-4-hydroxybenzyl) sulfide, isooctyl 3,5-di-tert-butyl-4-hydroxybenzylmercaptoacetate.
1.8. Hydroxybenzylated malonates, e.g. dioctadecyl 2,2-bis(3,5-di-tert-butyl-2-hydroxybenzyl)malonate, dioctadecyl 2-(3-tert-butyl-4-hydroxy-5-methylbenzyl)malonate, di(dodecylmercaptoethyl) 2,2-bis(3,5-di-tert-butyl-4-hydroxybenzyl)malonate, di[4-(1,1,3,3-tetramethylbutyl)phenyl] 2,2-bis(3,5-di-tert-butyl-4-hydroxybenzyl)malonate.
1.9. Hydroxybenzyl aromatics, e.g. 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.
1.10. Triazine compounds, e.g. 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4- tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl) isocyanurate.

1.11. Acylaminophenols, e.g. 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)propionic acid with monohydric or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo-[2.2.2]octane.

1.13. Esters of β-(5-tert-butyl-4-hydroxy-3-methylphenyl) propionic acid with monohydric or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(3,5-dicyclohexyl-4-hydroxyphenyl)propionic acid with monohydric or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of 3,5-di-tert-butyl-4-hydroxyphenylacetic acid with monohydric or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.16. Amides of β-(3,5-di-tert-butyl-4-hydroxyphenyl)propionic acid, e.g. N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl] oxamide (Naugard®XL-1, Uniroyal).

1.17. Ascorbic acid (Vitamin C).

1.18. Amine antioxidants, e.g. N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, e.g. p,p'-di-tert-octyidiphenylamine, 4-n-butylaminophenol, 4-butyrylaminophenol, 4-nonanoylaminophenol, 4-dodecanoylaminophenol, 4-octadecanoylaminophenol, di(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-di[(2-methylphenyl)amino]ethane, 1,2-di(phenylamino)propane, (o-tolyl)biguanide, di[4-(1',3'-dimethylbutyl)phenyl]amine, tert-octylated N-phenyl-1-naphthylamine, mixture of monoalkylated and dialkylated tert-butyl/tert-octyldiphenylamines, mixture of monoalkylated and dialkylated nonyldiphenylamines, mixture of monoalkylated and dialkylated dodecyidiphenylamines, mixture of monoalkylated and dialkylated isopropyl/isohexyldiphenylamines, mixtures of monoalkylated and dialkylated tert-butyldiphenylamines, 2,3-dihydro-3,3-dimethyl-4H-1,4-benzothiazine, phenothiazine, mixture of monoalkylated and dialkylated tert-butyl/tert-octyl-phenothiazines, mixture of monoalkylated and dialkylated tert-octylphenothiazines, N-allylphenothiazine, N,N,N',N'-tetrapheryl-1,4-diaminobut-2-ene, N,N-bis(2,2,6,6-tetramethylpiperidin-4-yl) hexamethylenediamine, bis(2,2,6,6-tetramethylpiperidin-4-yl) sebacate, 2,2,6,6-tetramethypiperidin-4-one, 2,2,6,6-tetramethylpiperidin-4-ol.

2. UV-absorbers and Light Stabilizers 2.1. 2-(2'-Hydroxyphenyl)benzotriazoles, e.g. 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl) phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylenebis[4-(1,1,3,3-tetramethylbutyl)6-benzotriazol-2-ylphenol]; transesterification product of 2-[3'-tert-butyl-5'-(2-methoxycarbonylethyl)-2'-hydroxyphenyl]benzotriazole with polyethylene glycol 300;

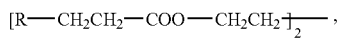

where R=3'-tert-butyl-4'-hydroxy-5'-2H-benzotriazole-2-ylphenyl; 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl)phenyl]benzotriazole.

2.2. 2-Hydroxybenzophenones, e.g. the 4-hydroxy, 4-methoxy, 4-octoxy, 4-decyloxy, 4-dodecyloxy, 4-benzyloxy, 4,2',4'-trihydroxy, 2'-hydroxy-4,4'-dimethoxy derivatives.

2.3. Esters of substituted or unsubstituted benzoic acids, e.g. 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, e.g. ethyl or isooctyl α-cyano-β,β-diphenylacrylate, methyl α-carbomethoxycinnamate, methyl or butyl α-cyano-β-methyl-p-methoxycinnamate, methyl α-carbomethoxyp-methoxycinnamate, N-(β-carbomethoxy-β-cyanovinyl)-2-methylindoline.

2.5. Nickel compounds, e.g. nickel complexes of bis[5-(1,1,3,3-tetramethylbutyl)-2-hydroxyphenyl] thioether, for example the 1:1 or 1:2 complex, with or without additional ligands such as n-butylamine, triethanolamine or N-cyclohexyldiethanolamine, nickel dibutyldithiocarbamate, nickel salts of monoalkyl 4-hydroxy-3,5-di-tert-butylbenzylphosphonates, e.g. of the methyl or ethyl ester, nickel complexes of ketoximes, e.g. of 2-hydroxy-4-methylphenylundecyl ketoxime, nickel complexes of 1-phenyl-4-lauroyl-5-hydroxypyrazole, with or without additional ligands.

2.6. Sterically hindered amines, e.g. bis(2,2,6,6-tetramethylpiperidin-4-yl) sebacate, bis(2,2,6,6-tetramethylpiperidin-4-yl) succinate, bis(1,2,2,6,6-pentamethylpiperidin-4-yl)sebacate, bis(1-octyloxy-2,2,6,6-tetramethylpiperidin-4-yl) sebacate, bis (1,2,2,6,6-pentamethylpiperidyl) n-butyl-3,5-di-tert-butyl-4-hydroxybenzylmalonate, condensation product of 1-hydroxyethyl-2,2,6,6-tetramethyl-4-hydroxypiperidine and succinic acid, linear or cyclic condensation products of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl) bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, linear or cyclic condensation products of N,N'-bis(2,2,6,6-tetramethyl-4-piperidyl)hexamethylenediamine and 4-morpholino-2,6-dichloro-1,3,5-triazine, condensation product or 2-chloro-4,6-di(4-n-butylamino-2,2,6,6-tetramethylpiperidyl)-1,3,5-triazine and 1,2-bis(3-aminopropylamino)ethane, condensation product of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, mixture of 4-hexadecyloxy- and 4-stearyloxy-2,2,6,6-tetramethylpiperidine, condensation product of N,N'-bis(2,2,6,6-tetramethyl-4-piperidyl)hexamethylenediamine and 4-cyclohexylamino-2,6-dichloro-1,3,5-triazine, condensation product of 1,2-bis(3-aminopropylamino)ethane and 2,4,6-trichloro-1,3,5-triazine and also 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, reaction product of 7,7,9,9-tetramethyl-2-cycloundecyl-1-oxa-3,8-diaza-4-oxospiro[4,5] decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexamethylenediamine, the diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic anhydride-α-olefin copolymer and 2,2,6,6-tetramethyl-4-aminopiperidine or 1,2,2,6,6-pentamethyl-4-aminopiperidine.

2.7. Oxamides, e.g. 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxamide, 2-ethoxy-5-tert-butyl-2'-ethyloxanilide and its mixture with 2-ethoxy-2'-ethyl-5,4'-di-tert-butyloxanilide, mixtures of o- and p-methoxy- and of o- and p-ethoxy-disubstituted oxanilides.

2.8. 2-(2-Hydroxyphenyl)-1,3,5-triazines, e.g. 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy) phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, e.g. N,N'-diphenyloxamide, N-salicylal-N'-salicyloyhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, oxalic acid bis(benzylidenehydrazide), oxanilide, isophthalic acid dihydrazide, sebacic acid bisphenylhydrazide, adipic acid N,N'-diacetyldihydrazide, oxalic acid N,N'-bis(salicyloyl-hydrazide), thiopropionic acid N,N'-bis(salicyloyhydrazide).

4. Phosphites and phosphonites, e.g. triphenyl phosphite, diphenyl alkyl phosphites, phenyl dialkyl phosphites, tris(nonylphenyl) phosphite, trilauryl phosphite, trioctadecyl phosphite, distearyl pentaerythritylphosphite, tris(2,4-di-tert-butylphenyl) phosphite, diisodecyl pentaerythrityldiphosphite, bis(2,4-di-tert-butylphenyl) pentaerythrityldiphosphite, bis(2,6-di-tert-butyl-4-methylphenyl) pentaerythrityldiphosphite, bisisodecyloxy pentaerythrityldiphosphite, bis(2,4-di-tert-butyl-6-methylphenyl) pentaerythrityldiphosphite, bis(2,4,6-tri-tert-butylphenyl) pentaerythrityldiphosphite, tristearyl sorbityltriphosphite, tetrakis(2,4-di-tert-butylphenyl) 4,4'-biphenylenediphosphonite, 6-isooctyloxy-2,4,8,10-tetra-tert-butyl-12H-dibenzo[d,g]-1,3,2-dioxaphosphocin, 6-fluoro-2,4,8,10-tetra-tert-butyl-12-methyl-dibenzo[d,g]-1,3,2-dioxaphosphocin, bis(2,4-di-tert-butyl-6-methylphenyl)methyl phosphite, bis(2,4-di-tert-butyl-6-methylphenyl)ethyl phosphite, 2,2',2"-nitrilo[triethyl tris-(3,3',5,5'tetra-tert-butyl-1,1'-biphenyl-2,2'-diyl) phosphite], 2-ethylhexyl (3,3',5,5'-tetra-tert-butyl-1,1'-biphenyl-2,2'-diyl) phosphite.

5. Hydroxylamines, e.g. N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow fatty amines.

6. Nitrones, e.g. N-benzyl α-phenyl nitrone, N-ethyl α-methyl nitrone, N-octyl α-heptyl nitrone, N-lauryl α-undecyl nitrone, N-tetradecyl α-tridecyl nitrone, N-hexadecyl α-pentadecyl nitrone, N-octadecyl α-heptadecyl nitrone, N-hexadecyl α-heptadecyl nitrone, N-octadecyl α-pentadecyl nitrone, N-heptadecyl α-heptadecyl nitrone, N-octadecyl α-hexadecyl nitrone, nitrones derived from N,N-dialkylhydroxylamines prepared from hydrogenated tallow fatty amines.

7. Thiosynergists, e.g. dilauryl thiodipropionate or distearyl thiodipropionate.

8. Polyamide stabilizers, e.g. copper salts in combination with iodides and/or phosphorus compounds and salts of divalent manganese.

9. Basic costabilizers, e.g. melamine, polyvinylpyrrolidone, dicyandiamide, triallylcyanurate, urea derivatives, hydrazine derivatives, amines, polyamides, polyurethanes, alkali metal and alkaline earth metal salts of higher fatty acids, e.g. calcium stearate, zinc stearate, magnesium behenate, magnesium stearate, sodium ricinoleate, potassium palmitate, antimony catecholate or zinc catecholate.

10. Nucleating agents, e.g. inorganic materials such as talc, metal oxides such as titanium dioxide or magnesium oxide, phosphates, carbonates or sulfates of, preferably, alkaline earth metals; organic compounds such as monocarboxylic acids or polycarboxylic acids and their salts, e.g. 4-tert-butylbenzoic acid, adipic acid, diphenylacetic acid, sodium succinate or sodium benzoate; polymeric compounds such as ionic copolymers ("ionomers").

11. Fillers and reinforcing materials, e.g. calcium carbonate, silicates, glass fibres, glass spheres, talc, kaolin, mica, barium sulfate, metal oxides and hydroxides, carbon black, graphite, wood flour and flours or fibres of other natural products, synthetic fibres.

12. Other additives, e.g. plasticizers, lubricants, emulsifiers, pigments, rheology modifiers, catalysts, levelling agents, optical brighteners, flame retardants, antistatics, blowing agents.

13. Benzofuranones or indolinones, as described, for example, in U.S. Pat. No. 4,325,863; U.S. Pat. No. 4,338,244; U.S. Pat. No. 5,175,312, U.S. Pat. No. 5,216,052; U.S. Pat. No. 5,252,643; DE-A-4316611; DE-A-4316622; DE-A-4 316 876; EP-A-0 589 839 or EP-A-0 591 102, or 3-[4-(2-acetoxyethoxy)phenyl]-5,7-di-tert-butyl-benzofuran-2-one, 5,7-di-tert-butyl-3-[4-(2-stearoyloxyethoxy)phenyl]-benzofuran-2-one, 3,3'-bis[5,7-di-tert-butyl-3-(4-[2-hydroxyethoxy]phenyl) benzofuran-2-one], 5,7-di-tert-butyl-3-(4-ethoxyphenyl) benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

In a specific embodiment of the invention, the polymer to be degraded is prepared with addition of the above-described hydroxylamine esters (I) together with selected antioxidants and processing stabilizers or mixtures of these. Examples of preferred compounds are:

pentaerythrityl tetrakis(3-(3,5-di-tert-butyl-4-hydroxyphenyl)propionate) (Irganox® 1010), octadecyl 3-(3,5-di-tert-butyl-4-hydroxyphenyl)propionate) (IRGANOX 1076), 3,3',3',5,5',5'-hexa-tert-butyl-α,α',α'-(mesitylene-2,4,6-triyl)tri-p-cresol (IRGANOX 1330), calcium diethyl bis(((3,5-bis(1,1-dimethylethyl)-4-hydroxyphenyl)methyl)phosphonate) (IRGANOX 1425), 1,3,5-tris(3,5-di-tert-butyl-4-hydroxybenzyl)-1,3,5-triazine-2,4,6(1H,3H,5H)trione (IRGANOX 3114);

tris(2,4-di-tert-butylphenyl) phosphite (Irgafos® 168), tris(nonylphenyl) phosphite, tetrakis(2,4-di-tert-butylphenyl) [1,1-biphenyl]-4,4'-diylbisphosphonite (IRGANOX P-EPQ), and also phosphites of the following structures:

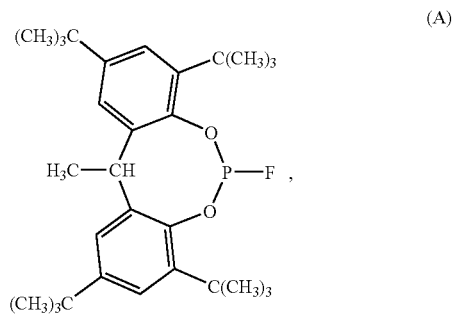

(A)

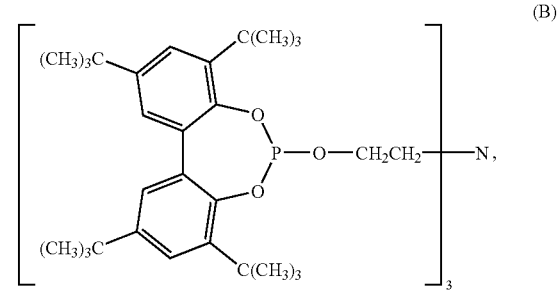

(B)

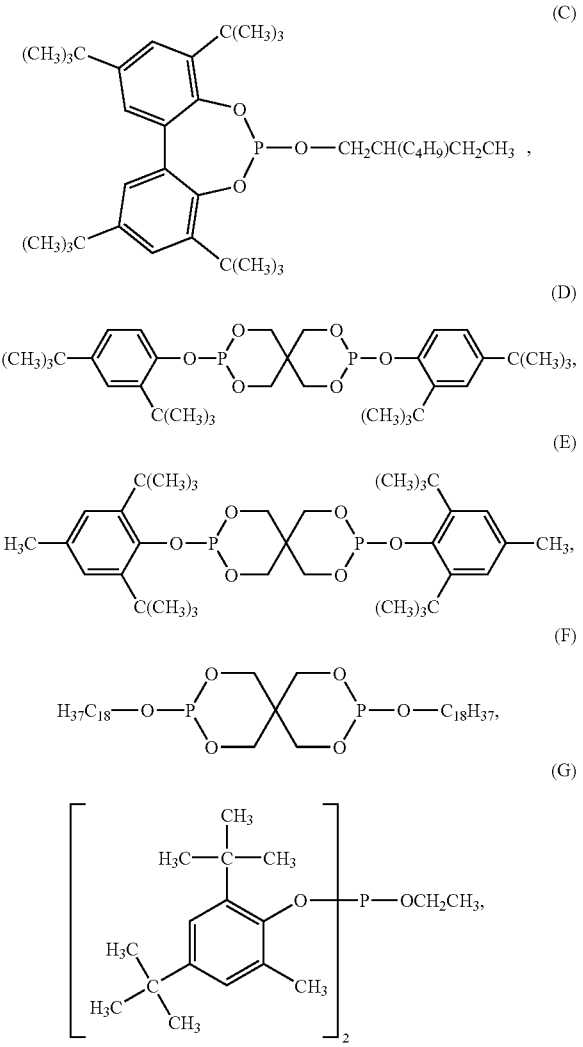

didodecyl 3,3'-thiodipropionate (IRGANOX PS 800), dioctadecyl 3,3'-thiodipropionate (IRGANOX PS 802); 5,7-di-tert-butyl-3-(3,4-dimethylphenyl)-3H-benzofuran-2-one (IRGANOX HP 136) and distearylhydroxylamine (Irgastab® FS 042).

Further additives which may be mentioned are antiacids such as calcium stearate or zinc stearate, hydrotalcites or calcium lactate, calcium lactylate from Patco (trade name Pationic).

In a specific embodiment, further sources of free radicals, e.g. a suitable bisazo compound, a peroxide or a hydroperoxide, in addition to the hydroxylamine esters (I) can be added to the polymers to be degraded.

Suitable bisazo compounds are commercially available, e.g. 2,2'-azobisisobutyronitrile, 2,2'-azobis(2-methylbutyronitrile), 2,2'-azobis(2,4-dimethylvaleronitrile), 2,2'-azobis (4-methoxy-2,4-dimethylvaleronitrile), 1,1'-azobis(1-cyclohexanecarbonitrile), 2,2'-azobis(isobutyramide) dihydrate, 2-phenylazo-2,4-dimethyl-4-methoxyvaleronitrile, dimethyl 2,2'-azobisisobutyrate, 2-(carbamoylazo)isobutyronitrile, 2,2'-azobis(2,4,4-trimethylpentane), 2,2'-azobis(2-methylpropane), 2,2'-azobis(N,N'-dimethyleneisobutyramidine) as free base or hydrochloride, 2,2'-azobis(2-amidinopropane) as free base or hydrochloride, 2,2'-azobis{2-methyl-N-[1,1-bis(hydroxymethyl)ethyl]propionamide} or 2,2'-azobis{2-methyl-N-[1,1-bis(hydroxymethyl)-2-hydroxyethyl]propionamide}.

Suitable peroxides and hydroperoxides are commercially available, e.g. acetylcyclohexanesulfonyl peroxide, diisopropyl peroxydicarbonate, tert-amyl perneodecanoate, tert-butylperneodecanoate, tert-butylperpivalate, tert-amylperpivalate, bis(2,4-dichlorobenzoyl) peroxide, diisononanoyl peroxide, didecanoyl peroxide, dioctanoyl peroxide, dilauroyl peroxide, bis(2-methylbenzoyl) peroxide, disuccinoyl peroxide, diacetyl peroxide, dibenzoyl peroxide, tert-butyl per-2-ethylhexanoate, bis(4-chlorobenzoyl) peroxide, tert-butyl perisobutyrate, tert-butyl permaleate, 1,1-bis(tert-butylperoxy)-3,5,5-trimethylcyclohexane, 1,1-bis(tert-butylperoxy)cyclohexane, tert-butyl peroxyisopropyl carbonate, tert-butyl perisononanoate, 2,5-dimethylhexane 2,5-dibenzoate, tert-butyl peracetate, tert-amyl perbenzoate, tert-butyl perbenzoate, 2,2-bis(tert-butylperoxy)butane, 2,2-bis (tert-butylperoxy)propane, dicumyl peroxide, 2,5-dimethylhexane 2,5-di-tert-butylperoxid, 3-tert-butylperoxy-3-phenyl phthalide, di-tert-amyl peroxide, α,α'-bis(tert-butylperoxyisopropyl) benzene, 3,5-bis(tert-butylperoxy)-3,5-dimethyl-1,2-dioxolane, di-tert-butyl peroxide, 2,5-dimethylhexyne 2,5-di-tert-butyl peroxide, 3,3,6,6,9,9-hexamethyl-1,2,4,5-tetraoxacyclononane, p-menthane hydroperoxide, pinane hydroperoxide, diisopropylbenzene mono-α-hydroperoxide, cumene hydroperoxide or tert-butyl hydroperoxide.

The abovementioned bisazo compounds, peroxides or hydroperoxides are added to the polymers to be degraded in amounts smaller than those customary when they are used alone in the processes of the prior art.

In a further preferred embodiment of the present invention, at least 2 free-radical initiators having different decomposition temperatures are employed, so that the degradation of the polymers may occur in 2 stages. This process is also referred to as sequential degradation.

Suitable compositions comprise, for example, the free-radical initiators of the invention and the abovementioned peroxides or a combination of the NOR-compounds described in WO 97/49737 and the hydroxylamine esters (I) described above.

It is essential that the two decomposition temperatures are sufficiently apart for effecting to a 2-stage process. For example, a peroxide having a decomposition temperature in the range of about 180–220° C. can be combined with a hydroxylamine ester (I) having a decomposition temperature in the range of about 240–280° C. or a hydroxylamine ester (I) having a decomposition temperature in the range of about 240–280° C. can be combined with an NOR-compound described in WO 97/49737 having a decomposition temperature above 300° C.

It has surprisingly been found that the degradation is advantageously be carried out in the presence of small amounts of free nitroxyl radicals. A more readily controllable degradation of the polymer is achieved, which leads to more constant melting properties. Suitable nitroxyl radicals are known and described in U.S. Pat. No. 4,581,429 or EP-A-621 878. Open-chain structures are described in WO 99/03894 and WO 00/07981. Furthermore, NO-derivatives of the piperidine type are described in WO 99/67298 and in British Patent Specification 2,335,190. Other NO-derivatives of heterocyclic compounds are described in British Patent Specification 2,342,649.

It is of course also possible to use mixtures of free-radical generators having different decomposition temperatures in the process.

A preferred embodiment of the invention relates to a process wherein a hydroxylamine ester (Ia), in which $R_a$ is an acyl radical selected from the group consisting of —C(=O)—$C_1$–$C_{19}$alkyl, trifluoroacetyl, benzoyl, —C(=O)—O—$C_1$–$C_6$alkyl, $C_1$–$C_6$alkylcarbamoyl and phenylcarbamoyl;

$R_1$–$R_4$ are each $C_1$–$C_6$alkyl;

$R_5$ and $R_6$ are each, independently of one another, hydrogen or $C_1$–$C_6$alkyl;

Q is the bivalent radical —($CR_7R_8$)—, where $R_7$ and $R_8$ are each hydrogen; and $Z_1$ is the bivalent radical —($CR_{12}R_{13}$)—, where, independently of one another, one of the radicals $R_{12}$ and $R_{13}$ is hydrogen and the other is etherified or esterified hydroxy selected from the group consisting of $C_1$–$C_6$alkoxy, benzoyloxy, —O—C(=O)—$C_1$–$C_{19}$alkyl, trifluoroacetoxy, $C_1$–$C_6$alkylcarbamoyloxy and phenylcarbamoyloxy, is added.

In this preferred embodiment, $R_1$–$R_4$ are each $C_1$–$C_6$alkyl, preferably methyl or ethyl.

$R_5$ and $R_6$ have the meanings specified above under a).

Q is the bivalent radical —($CR_7R_8$)— with hydrogen as $R_7$ and $R_8$.

$Z_1$ is the bivalent radical —($CR_{12}R_{13}$)—, where one of the radicals $R_{12}$ and $R_{13}$ is hydrogen and the other is etherified or esterified hydroxy selected from the group consisting of $C_1$–$C_6$alkoxy, e.g. methoxy, ethoxy or n-propoxy, benzoyloxy, —O—C(=O)—$C_1$–$C_{19}$alkyl, e.g. tert-butoxycarbonyloxy, trifluoroacetoxy, $C_1$–$C_6$alkylcarbamoyloxy and phenylcarbamoyloxy.

This preferred embodiment is based on the process using hydroxylamine esters (Ia), in which $R_a$ is, in particular, an acyl radical selected from the group consisting of —C(=O)—$C_1$–$C_{19}$alkyl, e.g. acetyl, pivaloyl or stearoyl, trifluoroacetyl, benzoyl, —C(=O)—O—$C_1$–$C_6$alkyl, e.g. tert-butoxycarbonyl, $C_1$–$C_6$alkylcarbamoyl, e.g. ethylcarbamoyl, and phenylcarbamoyl.

In a further preferred embodiment of the process, use is made of compounds of the above-described formula IC in which n=1:

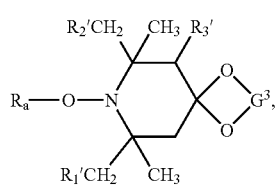

(IC')

where $R_a$, $R_1'$, $R_2'$ and $R_3'$ are as defined under the formula IA and $G^3$ is $C_2$–$C_8$alkylene, e.g. ethylene or 2,2-dimethylpropylene or 2,2-diethylpropylene or $C_4$–$C_{22}$acyloxyalkylene, e.g. 1-acetoxy-2,3-propylene, 2-$C_2$–$C_{18}$alkanoyloxymethyl-2-ethylpropylene, e.g. 2-acetoxymethyl-2-ethylpropylene or 2-palmitoyloxymethyl-2-ethylpropylene. Suitable compounds of the formula IC' have the following structural formulae:

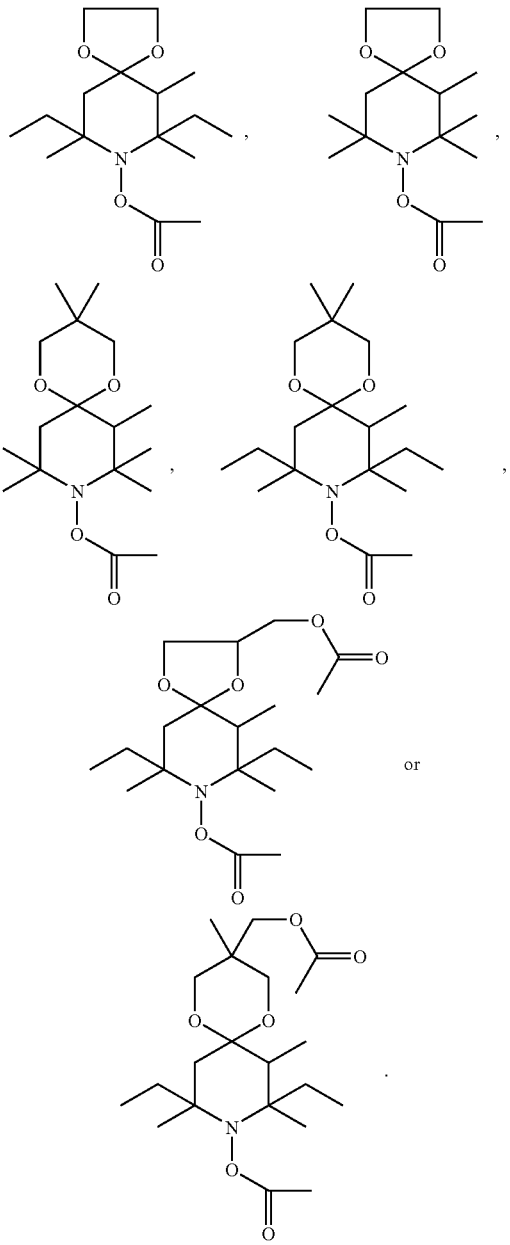

A particularly preferred embodiment relates to the process for reducing the molecular weight of polypropylene, propylene copolymers or polypropylene blends in which at least one of the abovementioned novel compounds a)–d) is added to these and the mixture is heated to temperatures below 280° C.

The invention further provides a process for achieving a controlled increase in the molecular weight or crosslinking of polyethylenes, e.g. low density polyethylene (LDPE), medium density polyethylene (MDPE), linear low density polyethylene (LLDPE), branched low density polyethylene (BLDPE) or polyethylenes produced using Phillips catalysts or polyethylene blends with polypropylene, propylene copolymers or polypropylene blends both using the above-described novel compounds and also using known hydroxylamine esters (I), in which the hydroxy group is esterified by the above-defined acyl radicals $R_a$.

A further advantageous property of the hydroxylamine esters (I) useful in process technology is their suitability for crosslinking polyethylene. The high molecular weight polyolefin grades required for pipe and cable production are synthesized mainly by crosslinking using peroxides [H. Domininghaus, *Die Kunststoffe und ihre Eigenschaften*, Springer-Verlag, Berlin, 5th edition, 1998, Chapter 2.1.1, pp. 156–159], e.g. Engel process: RAM extrusion with addition of peroxides; Sioplas process: peroxide-initiated grafting of vinylsilanes and subsequent crosslinking by means of water. If the desired parameters, for example the melt viscosity, are set by means of a polymer processing step, controlled reactivity and mode of action of the additives/additive systems added is essential for a successful reaction. While processing aids, e.g. polyethylene waxes, fluorinated polymers, metal soaps, fatty acid esters, etc., and fillers do not significantly influence the molecular weight and thus the processing behaviour of the polymers, crosslinking reactions with peroxides, multiply unsaturated olefins or unsaturated polymers generally present processing problems, e.g. very high melt viscosities, gel formation, etc., see above. Furthermore, reaction products of the peroxide and peroxide residues can cause a deterioration in the long-term stability of the polymers. Safety aspects in polymer processing with addition of peroxides also play an important role.

There is therefore a need for a simple-to-handle, effective additive system which allows controlled crosslinking, e.g. the targeted setting of the melt viscosity as a measure of the molecular weight, during polymer processing and which solves the problems associated with the use of peroxides as free-radical generators.

It has surprisingly been found that both the above-described novel compounds and also known hydroxylamine esters (I) in which the hydroxy group is esterified by the defined acyl radicals $R_a$ are suitable for achieving a controlled increase in the molecular weight/crosslinking of polyethylenes, e.g. low density polyethylene (LDPE), medium density polyethylene (MDPE), linear low density polyethylene (LLDPE), branched low density poly ethylene (BLDPE) or polyethylenes prepared using Phillips catalysts or polyethylene blends.

In the case of copolymers and terpolymers or copolymer blends, high proportions of ethylene result in polyethylene-like behaviour, while high proportions of propylene result in polypropylene-like behaviour. If the abovementioned copolymers and terpolymers or copolymer blends contain proportions of multiply unsaturated olefins, the probability of crosslinking increases with increasing concentration of free double bonds.

The degree of crosslinking of the polyethylene depends firstly on the nature of the polymer and secondly on the processing conditions (temperature) or the concentration of the additive used. A higher concentration of additive results in a higher degree of crosslinking.

The process for achieving a controlled increase in the molecular weight of polyethylenes, characterised in that a compound I, as defined above, particularly a compound (Ia), where $R_a$ is an acyl radical selected from the group consisting of —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl, —C(=O)—N($C_1$–$C_6$alkyl)$_2$, —P(=O)—$C_1$–$C_{19}$alkyl, —P(=O)$_2$—$C_1$–$C_{19}$alkyl, —P(=O)—$C_6$–$C_{10}$aryl, —P=O(—$C_1$–$C_{19}$alkyl)$_2$, —P=O(—$C_6$–$C_{10}$aryl)$_2$, —P(=O)—O—$C_1$–$C_6$alkyl, —P(=O)—O—$C_6$–$C_{10}$aryl, —P=O(—O—$C_1$–$C_6$alkyl)$_2$, —P=O(—O—$C_6$–$C_{10}$aryl)$_2$, —P(—O—$C_1$–$C_6$alkyl)$_2$ and —P(—O—$C_6$–$C_{10}$aryl)$_2$;

$R_1$–$R_4$ are each $C_1$–$C_6$alkyl;

$R_5$ and $R_6$ are each, independently of one another, hydrogen, $C_1$–$C_6$alkyl or $C_6$–$C_{10}$aryl; or $R_5$ and $R_6$ are together oxygen;

Q is a direct bond or a bivalent radical —($CR_7R_8$)— or —($CR_7R_8$13 $CR_9R_{10}$)—, where $R_7$, $R_8$, $R_9$ and $R_{10}$ are each, independently of one another, hydrogen or $C_1$–$C_6$alkyl; and $Z_1$ is oxygen or a bivalent radical —$NR_{11}$— or —($CR_{12}R_{13}$)—, where $R_{11}$ is hydrogen, $C_1$–$C_6$alkyl, $C_6$–$C_{10}$ aryl or the acyl radical $R_a$ having the abovementioned meanings; or, independently of one another, $R_{12}$ and $R_{13}$ are each hydrogen or $C_1$–$C_6$alkyl, or one of the radicals $R_{12}$ and $R_{13}$ is hydrogen or $C_0$–$C_6$alkyl and the other is $C_1$–$C_6$alkyl, $C_1$–$C_6$alkoxy, aryloxy, acyloxy selected from the group consisting of —O—C(=O)—H, —O—C(=O)—$C_1$–$C_{19}$alkyl, —O—C(=O)—$C_6$–$C_{10}$aryl, —O—C(=O)—O—$C_1$–$C_6$alkyl, —O—C(=O)—O—$C_6$–$C_{10}$aryl, —O—C(=O)—NH—$C_1$–$C_6$alkyl, —O—C(=O)—NH—$C_6$–$C_{10}$aryl and —O—C(=O)—N($C_1$–$C_6$alkyl)$_2$, $C_1$–$C_6$alkylamino, di-$C_1$–$C_6$alkylamino, $C_6$–$C_{10}$arylamino, acylamino selected from the group consisting of —NH—C(=O)—H, —NH—C(=O)—$C_1$–$C_{19}$alkyl, —NH—C(=O)—$C_6$–$C_{10}$aryl, —NH—C(=O)—O—$C_1$–$C_6$alkyl, —NH—C(=O)—O—$C_6$–$C_{10}$aryl, —NH—C(=O)—NH—$C_1$–$C_6$alkyl, —NH—C(=O)—NH—$C_6$–$C_{10}$aryl and —NH—C(=O)—N($C_1$–$C_6$alkyl)$_2$, diacylamino selected from the group consisting of —N[—C(=O)—$C_1$–$C_{19}$alkyl]$_2$, —N[—C(=O)—$C_6$–$C_{10}$aryl]$_2$, —N[—C(=O)—$C_1$–$C_6$alkylene-C(=O)—], —N[—C(=O)—$C_2$–$C_6$alkenylene-C(=O)—] and phthalimido or N-acyl-N—$C_1$–$C_6$alkylamino;

or the two radicals $R_{12}$ and $R_{13}$ are together oxo;

is added to the polyethylene or polyethylene blend whose molecular weight is to be increased.

The addition of the hydroxylamine esters (I), including the compounds IA–IN as defined above, to the ethylene polymer can be carried out in all customary mixing machines in which the polymer is melted and mixed with the additives. Suitable machines are known to those skilled in the art. These are mixers, kneaders and extruders. The process is preferably carried out by adding the additive during processing in an extruder.

Particularly preferred processing machines are single-screw extruders, corotating and counterrotating twin-screw extruders, planetary gear extruders, ring extruders or cokneaders provided with at least one gas removal compartment to which a vacuum can be applied.

Suitable extruders and kneaders are described, inter alia, in the abovementioned *Handbuch der Kunststoffextrusion*, Vol. 1, pp. 3–7.

If a plurality of components are added, these can be premixed or added individually.

The polymers are subjected to an elevated temperature for a sufficient period of time for the desired degradation to occur. In a preferred embodiment of the process of the present invention, a temperature range from about 160° C. to 300° C. is employed. In a particularly preferred process variant, the temperature range from about 170° C. to 280° C., in particular about 180–240° C., is used.

The period of time necessary for increasing the molecular weight or crosslinking can vary as a function of temperature, the amount of material whose molecular weight is to be increased and the type of any extruder employed. It is usually from about 10 seconds to 20 minutes, in particular from 20 seconds to 10 minutes.

The above-described hydroxylamine esters (I) are suitable for increasing the molecular weight of branched polyethylenes and polyethylene blends during compounding, where they, like the peroxides customarily used according to the prior art, effect crosslinking of the polymer chains.

In the process for increasing the molecular weight (crosslinking) of polyethylenes, the hydroxylamine esters (I) are present in concentrations of from about 0.01 to 10.0% by weight, in particular from 0.1 to 5.0% by weight, preferably from 0.2 to 3.0% by weight and particularly preferably from 0.1 to 2.0% by weight, based on the amount of polymer whose molecular weight is to be increased.

Suitable polymers of the polyethylene type are, for example, high density polyethylene (HDPE), high molecular weight high density polyethylene (HMW HDPE), ultrahigh molecular weight high density polyethylene (UHMW HDPE), medium density polyethylene (MDPE), low density polyethylene (LDPE), linear low density polyethylene (LL-DPE), branched low density polyethylene (BLDPE) or polyethylenes and ethylene copolymers prepared using Phillips catalysts and polyethylene blends. Ethylene copolymers can in this case contain differing proportions of comonomers. Examples which may be mentioned are: 1-olefins such as propene, 1-butene, 1-pentene, 1-hexene, 1-heptene, 1-octene or isobutylene, styrene, cycloolefins such as cyclopentene, cyclohexene or norbornene or dienes such as butadiene, isoprene, 1,4-hexadiene, cyclopentadiene, dicyclopentadiene, norbornadiene or ethylidenenorbornene.

Polyethylene blends are mixtures of polyethylenes with polyolefins. Examples are mixtures with polypropylene (PP), mixtures with various PE types, for example with: high density polyethylene (HDPE), high molecular weight high density polyethylene (HMW HDPE), ultrahigh molecular weight high density polyethylene (UHMW HDPE), medium density polyethylene (MDPE), low density polyethylene (LDPE), linear low density polyethylene (LLDPE), branched low density polyethylene (BLDPE) and, in particular, ethylene-propylene-diene terpolymers (EPDM) containing high proportions of diene.

Incorporation into the polymers can be carried out, for example, by mixing in the above-described novel or known hydroxylamine esters (I) or mixtures thereof and, if desired, further additives using methods customary in process technology.

Alternatively, incorporation can be carried out at temperatures which do not yet cause decomposition of the compounds used according to the invention (latent compound). The polymers prepared in this way can subsequently be heated a second time and subjected to an elevated temperature for a sufficient period of time for the desired increase in the molecular weight of the polymer (crosslinking) to occur.

The compounds can also be added in the form of a masterbatch containing these compounds in a concentration of, for example, from about 1 to 25% by weight to the polymers whose molecular weight is to be increased. The masterbatch (concentrate) can be prepared at temperatures which do not yet cause crosslinking of the compounds used according to the invention.

In a specific embodiment, additives and/or stabilizers as are described above for the process for degrading polypropylenes can be added to the polymer whose molecular weight is to be increased.

In a further specific embodiment, a source of free radicals, e.g. bisazo compounds, peroxides or hydroperoxides, as are described above for the process for degrading polypropylenes, can be added to the polymers whose molecular weight is to be increased in addition to the above-described hydroxylamine esters (I).

The bisazo compounds, peroxides or hydroperoxides mentioned are added to the polymers whose molecular weight is to be increased in amounts smaller than those customary when they are used alone according to processes of the prior art.

The above-described novel compounds can be prepared in a manner known per se. The preparation of these compounds is likewise the subject-matter of the invention and can be carried out, for example, by reacting an appropriate hydroxylamine of the formula:

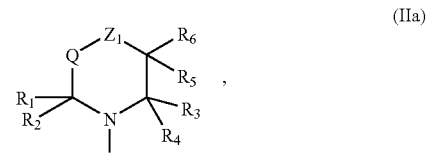

(IIa)

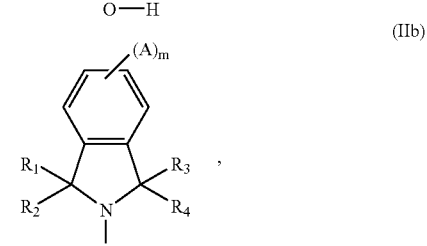

(IIb)

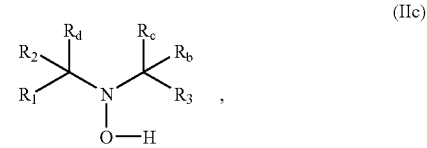

(IIc)

in a customary esterification reaction with an acid $R_a$—H which introduces the group $R_a$ and corresponds to an acyl radical selected, for example, from the group consisting of —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl and —C(=O)—N($C_1$–$C_6$alkyl)$_2$, or a reactive functional derivative thereof, e.g. the acid halide $R_a$—X, e.g. the acid chloride, or anhydride, e.g. $(R_a)_2$O.

Compounds (Ia) in which $R_a$ is an acyl radical selected from the group consisting of —P(=O)—$C_1$–$C_{19}$alkyl, —P(=O)—$C_6$–$C_{10}$aryl, —P(=O)$_2$—$C_6$–$C_{10}$aryl, —P=O(—$C_1$–$C_{19}$alkyl)$_2$, —P=O(—$C_6$–$C_{10}$aryl)$_2$, —P(=O)—O—$C_1$–$C_6$alkyl, —P(=O)—O—$C_6$–$C_{10}$aryl, —P=O(—O—$C_1$–$C_6$alkyl)$_2$, —P=O(—O—$C_6$–$C_{10}$aryl)$_2$, —P(—O—$C_1$–$C_6$alkyl)$_2$ and —P(—O—$C_6$–$C_{10}$aryl)$_2$ can likewise be prepared by esterification of the hydroxylamines with reactive functional derivatives, e.g. acid halides, of the corresponding phosphorus-containing acids.

The bicyclic compounds Id) can be prepared, for example, by reacting a hydroxylamine (IIa) with a functional derivative of a dicarboxylic acid (HOOC)₂X, capable of introducing the group

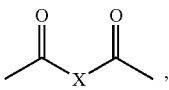

for example the dihalide (XOC)₂X, e.g. oxalyl chloride (X=0, direct bond) or adipoyl chloride (X=4).

The above-described starting materials for preparing the novel compounds are known.

The preparation of known hydroxylamine esters (Ia) which can be used in processes for preparing an oligomer, cooligomer, a polymer or a copolymer by free-radical polymerization are described, for example, in the U.S. Pat. Nos. 4,590,231, 5,300,647, 4,831,134, 5,204,473, 5,004,770, 5,096,950, 5,021,478, 5,118,736, 5,021,480, 5,015,683, 5,021,481, 5,019,613, 5,021,486, 5,021,483, 5,145,893, 5,286,865, 5,359,069, 4,983,737, 5,047,489, 5,077,340, 5,021,577, 5,189,086, 5,015,682, 5,015,678, 5,051,511, 5,140,081, 5,204,422, 5,026,750, 5,185,448, 5,180,829, 5,262,538, 5,371,125, 5,216,156, 5,300,544.

The following examples illustrate the above-described subject-matter of the invention.

EXAMPLES

A) Preparation of Compounds

A 1: N-tert-Butyl-N-(1-tert-butylaminocarbonyl-1-methylethyl)hydroxylamine ester of acetic acid (101)

5.2 ml (0.055 mol) of acetic anhydride are added dropwise while cooling to a solution of 11.5 g (0.05 mol) of N-tert-butyl-N-(1-tert-butylaminocarbonyl-1-methylethyl) hydroxylamine), whose preparation is described in Example A2 of the WO 00/07891, and 0.5 g of 4-dimethylaminopyridine in 50 ml of pyridine. The mixture is stirred for another 18 hours at room temperature, then diluted with 500 ml of water and extracted with 2×50 ml of tert-butylmethyl ether. The organic phase is washed with 5% HCl and water and dried over MgSO₄. Distilling off the solvent on a rotary evaporator gives 25.3 g (93%) of the compound 101, which is in the form of a colourless liquid.

Calculated for $C_{14}H_{28}N_2O_3$: 61.73% C, 10.36% H, 10.28% N; found: 61.65% C, 10.37% H, 10.14% N.

A 2: N-tert-Butyl-N-(1-tert-butylaminocarbonyl-1-methylethyl)hydroxylamine ester of benzoic acid (102)

Repeating the procedure of Example A 1 using benzoyl chloride gives an 80% yield of the compound 102 which is obtained in the form of colourless crystals; melting point: 61–64° C. (hexane).

$^1$H-NMR (CDCl₃, 300 MHz): 1.27 s (t-Bu), 1.29 s (Me), 1.39 s (t-Bu), 1.49 s (Me), 7.45–8.08 m (5 ArH), 7.79 bs (NH).

A 3: 2,2,5,5-Tetramethyl-4-oxo-imidazolidin-1-yl acetate (103)

44.7 g (0.23 mol) of 39% peracetic acid are added dropwise to a suspension of 28.2 g (0.2 mol) of 2,2,5,5-tetramethyl-4-oxoimidazolidine (prepared as described by T. Toda et al.: *Bull. Chem. Soc.* Japan 44 3345 (1971)) in 200 ml of ethyl acetate while cooling in ice. The suspension is stirred for another 20 hours at room temperature and then filtered. The filter cake is washed with a little ethyl acetate and dried. This gives 18.9 g of 1-hydroxy-2,2,5,5-tetramethyl-4-oxoimidazolidine as a white powder; melting point: 240–245° C.; MS (EI): m/e=158 (M+).

Using this hydroxylamine compound in a procedure otherwise similar to the preparation of the compound 101 gives an 84% yield of the title compound 103 which is obtained in the form of colourless crystals; melting point: 188–190° C. (dichloromethane/hexane).

Calculated for $C_9H_{16}N_2O_3$: 53.99% C, 8.05% H, 13.99% N; found: 54.37% C, 7.90% H, 13.90% N.

A 4: 1,1,3,3-Tetramethyl-1,3-dihydroisoindol-2-yl 2,4,6-trimethylbenzoate (104)

6.6 g (0.035 mol) of 1,1,3,3-tetramethyl-1,3-dihydroisoindole N-oxide are hydrogenated to saturation in 66 ml of ethanol over 0.12 g of PtO₂ at atmospheric pressure. The catalyst is filtered off and the solvent is evaporated on a rotary evaporator, after which the crystalline residue is recrystallized from a little dichloromethane. This gives 5.2 g (78%) of N-hydroxy-1,1,3,3-tetramethyl-1,3-dihydroisoindole which is obtained in the form of colourless crystals; melting point: 128–130° C.

Calculated for $C_{12}H_{17}NO$: 75.35% C, 8.96% H, 7.32% N; found: 75.19% C, 8.95% H, 7.23% N.

Using this hydroxylamine compound and 2,4,6-trimethylbenzoyl chloride in a procedure otherwise similar to that for preparing the compound 101 gives a 92% yield of the compound 104 which is obtained in the form of colourless crystals; melting point: 181–183° C. (dichloromethane/methanol).

Calculated for $C_{22}H_{27}NO_2$: 78.30% C, 8.06% H, 4.15% N; found: 78.46% C, 8.12% H, 4.02% N.

A 5: 1-Acetoxy-2,2,6,6-tetramethylpiperidin-4-yl benzoate (105)

Using 1-hydroxy-4-benzoyloxy-2,2,6,6-tetramethylpiperidine (prepared as described by: T. Kurumada et. al., *J. Polym. Sci., Polym. Chem. Ed.* (1984), 22(1), 277–81) in a procedure otherwise similar to that for preparing the compound 101 gives a 90% yield of the compound 105 which is obtained in the form of colourless crystals; melting point: 110–112° C. (acetonitrile).

Calculated for $C_{18}H_{25}NO_4$: 67.69% C, 7.89% H, 4.39% N; found: 67.61% C, 7.77% H, 4.38% N.

A 6: 4-Acetoxy-2,2,6,6-tetramethylpiperidin-1-yl acetate (106)

Using 1,4-dihydroxy-2,2,6,6-tetramethylpiperidine, prepared as described by: Paleos C. M. et al., *J. Chem. Soc., Chem. Commun.* (1977), (10), 345–6, in a procedure otherwise similar to the preparation of the compound 101 gives a 40% yield of the compound 106 which is obtained in the form of colourless crystals; melting point: 70–73° C. (acetonitrile).

$^1$H-NMR (300 MHz, CDCl₃): 5.13–5.03 m (1H), 2.11 s (CH₃), 2.04 s (CH₃), 1.95–1.74 m (4H), 1.25 s (2×CH₃), 1.11 s (2×CH₃).

A 7: 1-(2,2-Dimethylpropionyloxy)-2,2,6,6-tetramethylpiperidin-4-yl benzoate (107)

Using 1-hydroxy-4-benzoyloxy-2,2,6,6-tetramethylpiperidine (prepared as described by: Kurumada T. et. al., loc. cit.) and pivaloyl chloride in a procedure otherwise similar to the preparation of the compound 101 gives a 70% yield of the compound 107 which is obtained in the form of colourless crystals; melting point: 107–110° C. (hexane).

Calculated for $C_{21}H_{31}NO_4$: 69.78% C, 8.64% H, 3.8% N; found: 69.69% C, 8.54% H, 3.86% N.

A 8: 4-(2,2-Dimethylpropionyloxy)-2,2,6,6-tetramethylpiperidin-1-yl 2,2-dimethylpropionate (108)

Using 1,4-dihydroxy-2,2,6,6-tetramethylpiperidine, prepared as described by: Paleos C. M. et al., loc. cit., and pivaloyl chloride in a procedure otherwise similar to the preparation of the compound 101 gives a 67% yield of the compound 108 which is obtained in the form of colourless crystal; melting point: 43–46° C. (pentane).

$^1$H-NMR (300 MHz, CDCl$_3$): 5.09–5.01 m (1H), 1.92–1.74 m (4H), 1.28 s (t-Bu), 1.26 s (2×CH$_3$), 1.18 s (t-Bu), 1.08 s (2×CH$_3$).

A 9: 2,2,6,6-Tetramethyl-1-octadecanoyloxypiperidin-4-yl benzoate (109)

Using 1-hydroxy-4-benzoyloxy-2,2,6,6-tetramethylpiperidine, prepared as described by Kurumada T. et. al., loc.cit., and stearoyl chloride in a procedure otherwise similar to the preparation of the compound 101 gives a 60% yield of the compound 109 which is obtained in the form of colourless crystals; melting point: 85–89° C. (acetonitrile).
Calculated for $C_{34}H_{57}NO_4$: 75.09% C, 10.56% H, 2.58% N; found: 75.00% C, 10.22% H, 2.57% N.

A 10: 2,2,6,6-Tetramethyl-4-propoxypiperidin-1-yl 2,2-dimethylpropionate (110)

21.4 g (0.1 mol) of 4-propoxy-2,2,6,6-tetramethylpiperidine N-oxide (for preparation, see DE-A-4 219 459) are hydrogenated to saturation at 4 bar in 20 ml of toluene using 0.05 g of platinum (10% on carbon). The catalyst is filtered off and 13 g (0.108 mol) of pivaloyl chloride are slowly added dropwise to the colourless filtrate under nitrogen. After the slightly exothermic reaction has abated, the mixture is stirred for another 1 hour at room temperature and diluted with 20 ml of water. The organic phase is washed with 4% NaOH solution, dried over MgSO$_4$ and freed of the toluene on a rotary evaporator. This gives 13.5 g (45%) of the compound 110 which is in the form of a colourless oil.

$^1$H-NMR (300 MHz, CDCl$_3$): 3.63–3.54 m (1H), 3.38 t (CH$_2$), 1.92–1.48 m (6H), 1.27 s (t-Bu), 1.23 s (2×CH$_3$), 0.93 s (2×CH$_3$), 0.90 t (CH$_3$).

A 11: 1-Benzoyloxy-2,2,6,6-tetramethylpiperidin-4-yl benzoate (111)

Using 1-hydroxy-4-benzoyloxy-2,2,6,6-tetramethylpiperidine, prepared as described by: Kurumada T. et. al., loc. cit., and benzoyl chloride in a procedure otherwise similar to that for preparing the compound 101 gives an 83% yield of the compound 111 which is obtained in the form of colourless crystals; melting point. 138–140° C. (toluene/hexane).
Calculated for $C_{23}H_{27}NO_4$: 72.42% C, 7.13% H, 3.67% N; found: 72.28% C, 7.20% H, 3.70% N.

A 12: 2,2,6,6-Tetramethyl-4-propoxypiperidin-1-yl acetate (112)

A mixture of 21.4 g (0.1 mol) of 4-propoxy-2,2,6,6-tetramethylpiperidine N-oxide (for preparation, see DE-A-4 219 459) and 11 g (0.108 mol) of acetic anhydride is hydrogenated to saturation at 4 bar over 0.15 g of platinum (10% on carbon). The catalyst is filtered off and the filtrate is diluted with 50 ml of t-butyl methyl ether, washed with cold 12% NaOH solution, 5% HCl and finally water, dried over MgSO$_4$ and freed of the solvent on a rotary evaporator. This gives 18.1 g (70%) of the compound 112 which is in the form of a colourless oil.

$^1$H-NMR (300 MHz, CDCl$_3$): 3.60–3.50 m (1H), 3.34 t (CH$_2$), 2.05 s (CH$_3$CO), 1.90–1.49 m (6H), 1.15 s (2×CH$_3$), 1.05 s (2×CH$_3$), 0.87 t (CH$_3$).

A 13: Bis(4-benzoyloxy-2,2,6,6-tetramethylpiperidin-1-yl) hexanedicarboxylate (113)

Using 1-hydroxy-4-benzoyloxy-2,2,6,6-tetramethylpiperidine, prepared as described by: Kurumada T. et. al., loc. cit., and adipoyl chloride in a procedure otherwise similar to that for preparing the compound 101 gives an 81% yield of the compound 113 which is obtained in the form of colourless crystals; melting point: 130–135° C. (dichloromethane/acetonitrile).
Calculated for $C_{38}H_{52}N_2O_8$: 68.65% C, 7.88% H, 4.21% N. found: 68.58% C, 8.07% H, 4.34% N.

A 14: Bis(4-benzoyloxy-2,2,6,6-tetramethylpiperidin-1-yl) oxalate (114)

Using 1-hydroxy-4-benzoyloxy-2,2,6,6-tetramethylpiperidine, prepared as described by: Kurumada T et. al., loc. cit., and oxalyl chloride in a procedure otherwise similar to that for preparing the compound 101 gives a 70% yield of the compound 114 which is obtained in the form of colourless crystals; melting point: 211–215° C. (dichloromethane/hexane).
Calculated for $C_{33}H_{44}N_2O_8$: 67.09% C, 7.29% H, 4.60% N; found: 66.89% C, 7.22% H, 4.56% N.

A 15: 1-tert-Butoxycarbonyloxy-2,2,6,6-tetramethylpiperidin-4-yl benzoate (115)

6.95 g (0.025 mol) of 1-hydroxy-4-benzoyloxy-2,2,6,6-tetramethylpiperidine, prepared as described by: T. Kurumada et. al., loc. cit., 0.15 g of 4-dimethylaminopyridine and 9.5 g (0.043 mol) of di-tert-butyl dicarbonate in 30 ml of THF are stirred at 45° C. for 30 hours. The reaction mixture is evaporated to dryness on a rotary evaporator. Chromatography of the residue on silica gel using hexane ethyl acetate 9:1 gives 6.2 g (66%) of the compound 115, which, after recrystallization from dichloromethane/hexane, melts at 109–111° C.
Calculated for $C_{21}H_{31}NO_5$: 66.82% C, 8.28% H, 3.71% N; found: 66.83% C, 7.96% H, 3.65% N.

A 16: 1-Diphenylphosphinoyloxy-2,2,6,6-tetramethylpiperidin-4-yl benzoate (116)

Using 1-hydroxy-4-benzoyloxy-2,2,6,6-tetramethylpiperidine, prepared as described by: Kurumada T. et. al., loc. cit., and diphenylphosphinic chloride in a procedure otherwise similar to that for preparing the compound 101 gives an 84% yield of the compound 116 which is obtained in the form of colourless crystals; melting point: 169–173° C. (dichloromethane/hexane).
Calculated for $C_{28}H_{32}NO_4P$: 70.43% C, 6.75% H, 2.93% N; found: 70.25% C, 6.67% H, 2.79% N.

A 17: 1-Ethylcarbamoyloxy-2,2,6,6-tetramethylpiperidin-4-yl ethylcarbamate (117)

20 ml (0.26 mol) of ethyl isocyanate are added dropwise under nitrogen to 10.0 g (0.058 mol) of 1,4-dihydroxy-2;2,6,6-tetramethylpiperidine, prepared as described by Paleos C. M. et al., loc. cit., in 100 ml of 1,2-dichloroethane. The mixture is stirred at 70° C. for 30 hours and then evaporated to dryness on a rotary evaporator. Recrystallization of the residue from xylene gives 14.4 g (77%) of the compound 117 as colourless crystals; melting point: 149–151° C.
Calculated for $C_{15}H_{29}N_3O_4$: 57.12% C, 9.27% H, 13.32% N; found: 57.42% C, 9.28% H, 13.02% N.

A 18: 1-Phenylcarbamoyloxy-2,2,6,6-tetramethylpiperidin-4-yl phenylcarbamate (118)

The compound 118 is prepared using phenyl isocyanate in a procedure similar to that for preparing the compound 117, and is obtained in a 64% yield as colourless crystals; melting point: 188–190° C.

$^1$H-NMR (300 MHz, CDCl$_3$): 8.7 bs (NH), 7.49–7.08 m (10 ArH), 6.63 bs (NH), 5.20–5.10 m (1H), 2.33–1.72 m (4H), 1.42 s (2×CH$_3$), 1.27 s (2×CH$_3$).

A 19: 1-Acetoxy-2,2-diethyl-6,6-dimethylpiperidin-4-yl acetate (119)

2,2-Diethyl-6,6-dimethyl-4-hydroxypiperidine N-oxide (for preparation, see German Patent Application 199 49 352.9) is hydrogenated using a method analogous to Example A 10 to give the corresponding hydroxylamine. The crude hydroxylamine is acetylated by means of acetic anhydride using a method analogous to Example A 1. The compound 119 is obtained in a 62% yield as a yellowish oil.

$^1$H-NMR (300 MHz, CDCl$_3$): 5.10–5.0 m (1H), 2.05 s (CH$_3$CO), 2.03 s (CH$_3$CO), 1.95–1.52 m (8H), 1.28 s (CH$_3$), 1.10 s (CH$_3$), 0.98–0.83 m (2×CH$_3$).

A 20: 4-Acetoxy-2,6-diethyl-2,3,6-trimethylpiperidin-1-yl acetate (120)

The compound 120 is prepared from 2,6-diethyl-2,3,6-trimethyl-4-hydroxypiperidine N-oxide using a method analogous to Example A 19 as a slightly yellowish oil.

$^1$H-NMR (300 MHz, CDCl$_3$): 5.40–4.85 m (1H), 2.23–0.8 m (28H).

A 21: 4-Acetoxy-2,6-diethyl-2,3,6-trimethylpiperidin-1-yl 2,2-dimethylpropionate (121)

2,6-Diethyl-2,3,6-trimethyl-4-hydroxypiperidine N-oxide (for preparation, see German Patent Application 199 49 352.9) is acetylated using a method analogous to Example A 1 and converted by a method analogous to Example A 10 into the compound 121 which is obtained in the form of a colourless oil.

$^1$H-NMR (300 MHz, CDCl$_3$): 5.36–4.83 m (1H), 2.20–0.77 m (34H).

A 22: 4-tert-Butyl-2,2-diethyl-6,6-dimethyl-3-oxopiperazin-1-yl acetate (122)

4-tert-Butyl-2,2-diethyl-6,6-dimethylpiperazin-3-one N-oxide (for preparation, see German Patent Application 19949 352.9) is reduced to the corresponding hydroxylamine using a method analogous to Example A 10 and converted by acetylation using a method analogous to Example 1 into the oily compound 122.

$^1$H-NMR (300 MHz, CDCl$_3$): 3.24–3.15 m (2H), 2.04 s (CH$_3$CO), 2.04–1.72 m (2×CH$_2$), 1.40 s (t-Bu), 1.19 s (CH$_3$), 1.12 s (CH$_3$), 0.99–0.91 m (2 CH$_3$).

A 23: 4-tert-Butyl-2,2,6,6-tetraethyl-3-oxopiperazin-1-yl acetate (123)

4-tert-Butyl-2,2,6,6-tetraethylpiperazin-3-one N-oxide (for preparation, see German Patent Application 199 49 352.9) is converted by a method similar to Example A 22 into the oily compound 123.

$^1$H-NMR (300 MHz, CDCl$_3$): 3.21–3.16 m (2H), 2.05 s (CH$_3$CO), 2.05–1.46 m (4×CH$_2$), 1.43 s (t-Bu), 1.00–0.87 m (4×CH$_3$).

A 24: 4-tert-Butyl-2,2,6,6-tetraethyl-3-oxopiperazin-1-yl benzoate (124)

The procedure of Example A 23 is repeated using benzoyl chloride to give the compound 124 which is obtained in the form of colourless crystals; melting point: 91–93° C.

Calculated for C$_{23}$H$_{36}$N$_2$O$_3$: 71.10% C, 9.34% H, 7.21% N; found: 71.12% C, 9.42% H, 7.18% N.

A 25: 4-tert-Butyl-2,2,6,6-tetraethyl-3-oxopiperazin-1-yl 2,2-dimethylpropionate (125)

The procedure of Example A 23 is repeated using pivaloyl chloride to give the compound 125 which is obtained in the form of colourless crystals; melting point: 58–60° C.

Calculated for C$_{21}$H$_{40}$N$_2$O$_3$: 68.44% C, 10.94% H, 7.60% N; found: 68.29% C, 10.43% H, 7.49% N.

A 26: 2,2,6,6-Tetramethyl-4-(2,2,2-trifluoracetoxy)-piperidin-1-yl trifluoroacetate (126)

The procedure of Example A 6 is repeated using trifluoroacetic anhydride to give the compound 126 which is obtained in the form of colourless crystals.

$^1$H-NMR (300 MHz, CDCl$_3$): 5.34–5.24 m (1H), 2.31–1.87 m (4H), 1.33 s (2×CH$_3$), 1.19 s (2×CH$_3$).

A 27: 1-Trifluoroacetoxy-4-tert-butyl-2,2-diethyl-6,6-dimethylpiperazin-3-one (127)

The procedure of Example A 22 is repeated using trifluoroacetic anhydride to give the compound 127 which is obtained as a colourless oil.

$^1$H-NMR (300 MHz, CDCl$_3$): 3.27–3.14 m (2H), 2.20–0.95 m (16H), 1.46 s (t-Bu).

A 28: 4-(N-Acetyl-N-2,2-dimethylpropionylamino)-2,2,6,6-tetramethylpiperidin-1-yl 2,2-dimethylpropionate (128)

A solution of 21 g (0.098 mol) of 1-acetylaminotetramethylpiperidine 1-oxide (Fluka) in 170 ml of THF is hydrogenated over 0.5 g of platinum catalyst (5% on carbon) at room temperature and 3 bar until no more hydrogen is absorbed. The catalyst is filtered off and the filtrate is evaporated on a rotary evaporator. The colourless, crystalline residue is dissolved in 100 ml of pyridine and admixed with 13.7 ml (0.11 mol) of pivaloyl chloride. After stirring at room temperature for 1 hour, the mixture is poured into 250 ml of ice-water, the precipitate formed is filtered off with suction and recrystallized from acetonitrile. This gives 4.6 g of the title compound (128) in the form of colourless crystals; melting point: 169–173° C.

$^1$H-NMR (300 MHz, CDCl$_3$): 4.04–3.96 m (1H), 2.32–2.24 m (2H), 2.16 s (COCH$_3$), 1.65–1.60 (m, 2H), 1.28 s (t-Bu), 1.27 s (t-Bu), 1.25 s (2×CH$_3$), 1.20 s (2×CH$_3$).

A 29: 4-Acetylamino-2,2,6,6-tetramethylpiperidin-1-yl 2,2-dimethylpropionate (129)

The aqueous filtrate after isolation of the compound 128 from Example 28 is extracted 3× with 100 ml of dichloromethane. The extracts are washed 8× with 20 ml of water and evaporated on a rotary evaporator. The residue is dissolved in 20 ml of dichloromethane, washed with 10 ml of 10% NaOH and evaporated again. Recrystallization of the residue from toluene/hexane gives 4.68 g of the title compound 129; melting point: 128–135° C.

$^1$H-NMR (300 MHz, CDCl$_3$): 5.92 bs (NH), 4.29–4.18 m (1H), 1.96 s (COCH$_3$), 1.89–1.83 m (2H), 1.67–1.59 (m, 2H), 1.28 s (t-Bu), 1.27 s (2×CH$_3$), 1.06 s (2×CH$_3$).

A 30: 4-Acetylamino-2,2,6,6-tetramethylpiperidin-1-yl acetate (130)

A solution of 21.4 g (0.1 mol) of 4-acetylaminotetramethylpiperidine 1-oxide (Fluka) and 0.1 g of 4-dimethylaminopyridine in 150 ml of acetic anhydride is hydrogenated over 0.5 g of platinum catalyst (5% on carbon) at room temperature and 3 bar until no more hydrogen is absorbed. The catalyst is filtered off and the filtrate is evaporated on a rotary evaporator. Recrystallization of the residue from acetonitrile gives 8.85 g of the title compound 130 as colourless crystals; melting point: 129–32° C.

¹H-NMR (300 MHz, CDC₃): 5.66 bs (NH), 4.29–4.16 m (1H), 2.10 s (COCH₃), 1.96 s (COCH₃), 1.89–1.84 m (2H), 1.62–1.54 (m, 2H), 1.25 s (2×CH₃), 1.08 s (2×CH₃).

A 31: Bis[1-(2,2-dimethylpropionyloxy)-2,2,6,6-tetramethylpiperidin-4-yl]-decanedioate (131)

15.3 g (0.03 mol) of bis(2,2,6,6-tetramethyl-1-oxypiperidin-4-yl) sebacate (prepared as described in *Polym. Degrad. Stab.* (1982), 4(1), 1–16) are converted by a method similar to Example A 28 into 16,8 g of the title compound 131; melting point: 93–97° C.

¹H-NMR (300 MHz, CDCl₃): 5.12–5.03 m (2H), 2.29–1.92 m (4H), 1.91–1.57 (14H), 1.32–1.23 (36H), 1.08 s (12H).

A 32: 4(N-Acetyl-N-n-butylamino)-2,2,6,6-tetramethylpiperidin-1-yl 2,2-dimethylpropionate (132)

26.95 g (0.1 mol) of 4-(N-acetyl-N-n-butylamino)-2,2,6,6-tetramethylpiperidine 1-oxide (prepared as described in WO 00/03965) are converted by a method similar to Example A 28 into 26 g of the title compound 132 which is obtained as colourless crystals; melting point: 81–94° C.

Calculated for C₂₀H₃₈N₂O₃: 67.75% C, 10.80% H, 7.90% N; found 67.74% C, 10.78% H, 7.87% N.

A 33: 2,6-Diethyl-2,3,6-trimethyl-4-oxopiperidin-1-yl acetate (133)

10.95 g (0.052 mol) of 2,6-diethyl-2,3,6-trimethyl-4-oxopiperidine 1-oxide (for preparation, see DE-A 19909767) are converted by a method similar to Example A 30 into the title compound (133) which is obtained as a colourless oil; yield: 11.9 g.

Calculated for C₁₄H₂₅NO₃: 65.85% C, 9.87% H, 5.49% N; found 65.71% C, 9.64% H, 5.39% N.

A 34: 2,2,6,6-Tetramethyl-4-oxopiperidin-1-yl acetate (134)

The title compound is prepared by the method given in *J. Chem. Soc. Perkin Trans.* 1, 9, 2243 (1991).

A 35: 4-tert-Butyl-2,2-diethyl-6,6-dimethyl-3-oxopiperazin-1-yl phenylcarbamate (135)

4-tert-Butyl-2,2-diethyl-6,6-dimethylpiperazin-3-one N-oxide (for preparation, see German Patent Application 199 49 352.9) is reduced to the corresponding hydroxylamine by a method analogous to Example A-10 and converted by a method analogous to Example A 18 using phenyl isocyanate into the compound 135 which is obtained in the form of colourless crystals; melting point: 160–163° C.

Calculated for C₂₁H₃₃N₃O₃: 67.17% C, 8.86% H, 11.19% N; found 67.21% C, 8.84% H, 11.06% N.

A 36: 4-tert-Butyl-2,2-diethyl-6,6-dimethyl-3-oxopiperazin-1-yl diphenylacetate (136)

4-tert-Butyl-2,2-diethyl-6,6-dimethylpiperazin-3-one N-oxide (for preparation, see German Patent Application 199 49 352.9) is reduced to the corresponding hydroxylamine by a method analogous to Example 10 and converted by a method analogous to Example 25 using diphenylacetyl chloride into the compound 136 which is obtained in the form of colourless crystals; melting point: about 109° C.

¹H-NMR (300 MHz, CDCl₃): 7.38–7.26 m (10H), 5.0 s (1H), 3.22–3.00 m (2H), 1.93–1.61 m (4H), 1.40 s (9H), 1.12 s (3H), 0.98 s (3H), 0.97–0.81 m (6H).

A 37: 2,6-Diethyl-2,3,6-trimethylpiperidin-1-yl acetate (137)

2,6-Diethyl-2,3,6-trimethylpiperidine 1-oxide (for preparation, see U.S. Pat. No. 4,131,599) is converted by a method analogous to Example A 30 into the compound 137 which is obtained in the form of a colourless oil.

¹H-NMR (300 MHz, CDCl₃): 2.05 s (3H), 2.0–0.79 m (24H).

A 38: 2,6-Diethyl-2,3,6-trimethylpiperidin-1-yl stearate (138)

2,6-Diethyl-2,3,6-trimethylpiperidine 1-oxide (for preparation, see U.S. Pat. No. 4,131,599) is converted by a method analogous to Example A 30 using stearoyl chloride into the compound 137 which is obtained in the form of a colourless oil.

¹H-NMR (300 MHz, CDCl₃): 2.29 t (2H), 1.81–0.78 m (57H).

A 39: 3,3,8,8,10,10-Hexamethyl-1,5-dioxa-9-azaspiro[5.5]undec-9-yl acetate (139)

3,3,8,8,10,10-Hexamethyl-1,5-dioxa-9-azaspiro[5.5]undecane 9-oxide (for method of preparation, see EP-A-574 666) is converted by a method analogous to Example A 30 into the compound 139 which is obtained in the form of colourless crystals; melting point: 109–111° C.

¹H-NMR (300 MHz, CDCl₃): 3.48 bs (4H), 2.26 d (2H), 2.1 s (3H), 1.8 d (2H), 1.29 s (6H), 1.09 s (6H), 0.97 s (6H).

A 40: 7,9-Diethyl-6,7,9-trimethyl-1,4-dioxa-8-azaspiro[4.5]dec-8-yl acetate (140)

7,9-Diethyl-6,7,9-trimethyl-1,4-dioxa-8-azaspiro[4.5]decane 8-oxide (for preparation, see U.S. Pat. No. 4,105,626) is converted by a method analogous to Example A 30 into the compound 140 which is obtained as a colourless oil.

¹H-NMR (300 MHz, CDCl₃): 4.09–3.76 m (4H), 2.25–0.79 m (22H), 2.04 s (3H).

A 41: 8-Acetoxy-7,9-diethyl-6,7,9-trimethyl-1,4-dioxa-8-azaspiro[4.5]dec-2-ylmethyl acetate (141)

A solution of 10.25 g (0.035 mol) of 7,9-diethyl-6,7,9-trimethyl-1,4-dioxa-8-azaspiro[4.5]dec-2-yl)methanol 8-oxide (for method of preparation, see U.S. Pat. No. 4,105,626) is stirred with a solution of 20 g of sodium ascorbate in 40 ml of water under nitrogen for 4 hours. The colourless organic phase is separated off and evaporated on a rotary evaporator. The hydroxylamine derivative obtained in this way is converted by a method analogous to Example A 1 using acetic anhydride into the compound 141 which is obtained in the form of a colourless oil.

¹H-NMR (300 MHz, CDCl₃): 4.39–3.21 m (5H), 2.16–0.83 m (28H).

A 42: 8,1 O-Diethyl-3,3,7,8,10-pentamethyl-1,5-dioxa-9-azaspiro[5.5]undec-9-yl acetate (142)

8,10-Diethyl-3,3,7,8,10-pentamethyl-1,5-dioxa-9-azaspiro[5.5]undecane 9-oxide (for method of preparation, see U.S. Pat. No. 4,105,626) is converted by a method analogous to Example A 30 into the compound 142 which is obtained in the form of a colourless oil.

¹H-NMR (300 MHz, CDCl₃): 3.74–2.58 m (4H), 2.04 s (3H), 1.96–0.68 m (28H).

A 43: 3-Acetoxymethyl-3,8,10-triethyl-7,8,10-trimethyl-1,5-dioxa-9-azaspiro[5.5]undec-9-yl acetate (143)

3,8,10-Triethyl-7,8,10-trimethyl-1,5-dioxa-9-azaspiro[5.5]undec-3-ylmethanol (for method of preparation, see U.S. Pat. No. 4,105,626) is converted by a method analogous to Example A 30 into the compound 143 which is obtained as a colourless oil.

¹H-NMR (300 MHz, CDCl₃): 4.37–2.58 m (6H), 2.04 s (3H), 2.08–0.81 m (30H).

A 44: 9-Acetoxy-3,8,10-triethyl-7,8,10-trimethyl-1,5-dioxa-9-azaspiro[5.5]undec-3-ylmethyl stearate (144)

12 g (0.037 mol) of 3,8,10-triethyl-7,8,10-trimethyl-1,5-dioxa-9-azaspiro[5.5]undec-3-ylmethanol (for method of preparation, see U.S. Pat. No. 4,105,626) are dissolved in 40 ml of pyridine and admixed with 11.7 g (0.039 mol) of stearoyl chloride. After stirring for 18 hours at room temperature, the reaction mixture is diluted with 200 ml of water and extracted with 2×50 ml of methyl-t-butylether. After distilling off the solvent, the resulting stearoyl nitroxide is converted by a method analogous to Example A 30 into the compound 144 which is obtained in the form of a colourless oil.

$^1$H-NMR (300 MHz, CDCl$_3$): 4.39–2.58 m (6H), 2.32 t (2H), 2.04 s (3H), 1.91–0.80 m (62H).

A 45: 1-Acetoxy-2,2,6,6-tetramethylpiperidin-4-yl stearate (145)

2,2,6,6-Tetramethylpiperidin-4-yl stearate 1-oxide (for preparation, see WO 99/67298) is converted by a method similar to Example A 30 into the compound 145 which is obtained in the form of colourless crystals, melting point: 63–70° C.

$^1$H-NMR (300 MHz, CDCl$_3$): 5.12–5.03 m (1H), 2.29–2.22 t (2H), 2.06 s (3H), 1.93–0.84 m (49H).

A 46: 1-Acetoxy-2,6-diethyl-2,3,6-trimethylpiperidin-4-yl stearate (146)

2,6-Diethyl-2,3,6-trimethylpiperidin-4-yl stearate 1-oxide (for preparation, see DE-A-199 49 352.9) is converted by a method similar to Example A 30 into the compound 146 which is obtained in the form of a colourless oil.

Calculated for C$_{32}$H$_{61}$NO$_4$: 73.37% C, 11.74% H, 2.67% N; found 73.39% C, 11.5.8% H, 2.58% N.

A 47: Bis(1-acetoxy-2,2,6,6-tetramethylpiperidin-4-yl) decanedioate (147)

The (2,2,6,6-tetramethylpiperidin-4-yl 1-oxide) diester of decanedioate, for preparation, see WO 99/05108, is converted by a method similar to Example A 30 into the compound 147 which is obtained in the form of colourless crystals; melting point: 81–94° C.

Calculated for C$_{32}$H$_{56}$N$_2$O$_8$: 64.40% C, 9.46% H, 4.69% N; found 64.18% C, 9.44% H, 4.61% N.

A 48: Bis(1-acetoxy-2,2,6,6-tetramethylpiperidin-4-yl) terephthalate (148)

The (2,2,6,6-tetramethylpiperidin-4-yl 1-oxide) diester of terephthalic acid (for preparation, see Z. Naturforsch., B: Chem. Sci. 55(7), 567–575 (2000)) is converted by a method similar to Example A 30 into the compound 148 which is obtained in the form of colourless crystals; melting point: 206–212° C.

Calculated for C$_{30}$H$_{44}$N$_2$O$_3$: 64.27% C, 7.91% H, 5.00% N; found 63.79% C, 7.93% H, 4.87% N.

A 49: 4-{[4,6-bis-(1-acetoxy-2,2,6,6-tetramethylpiperidin-4-yl)butylamino[1,3,5]triazin-2-yl]butylamino}-2,2,6,6-tetramethylpiperidin-1-yl acetate (149)

18.5 ml of peracetic acid (40% in acetic acid) are added dropwise to a solution of 12.85 g (0.018 mol) of N,N',N''-tributyl-N,N',N''-tris-(2,2,6,6-tetramethylpiperidin-4-yl)[1,3,5]triazin-2,4,6-triamine (for preparation, see EP-A-107,615) in 95 ml of dichloromethane. The solution is stirred for 20 hours, washed with water and 10% NaHCO$_3$ solution and evaporated. 25 ml of tetrahydrofuran, 7.2 ml of acetic anhydride and 2.8 g of platinum catalyst (5% on carbon) are added to the residue and the mixture is hydrogenated to saturation at a hydrogen pressure of 4 bar. The catalyst is filtered off and the filtrate is evaporated on a rotary evaporator. The residue is slurried in 30 ml of acetonitrile, filtered and dried. This gives 10.3 g of the compound 149 as a colourless powder; melting point: 232–244° C.

$^1$H-NMR (300 MHz, CDCl$_3$): 5.37–5.29 m (3H), 3.32–3.29 m (6H), 2.08 s (9H), 1.96–1.87 t (6H), 1.61–1.49 m (18H), 1.28 s (18H), 1.11 s (18H), 0.92–0.87 t (9H).

A 50: Polymer (150) of
a) 2,4,6-trichloro-1,3,5-triazine
b) 4-{6-[1-(2,2-dimethylpropionyloxy)-2,2,6,6-tetramethylpiperidin-4-ylamino]hexylamino}-2,2,6,6-tetramethylpiperidin-1-yl 2,2-dimethylpropionate
c) 4-butylamino-2,2,6,6-tetramethylpiperidin-1-yl 2,2-dimethylpropionate
d) dibutylamine.

25 g of CHIMASSORB®2020 (manufacturer: Ciba SC) are converted using a method similar to Example A 49 using pivaloyl chloride into 199 of polymer 150 which is obtained as a colourless powder; melting point: 140–160° C.

$^1$H-NMR (300 MHz, CDCl$_3$): 5.06–4.25 m, 3.1–2.9 m, 1.95–0.58 m

A 51: Polymer (151) of:
a) 2,4,6-trichloro-1,3,5-triazine
b) 4-[6-(1-acetoxy-2,2,6,6-tetramethylpiperidin-4-ylamino)hexylamino]-2,2,6,6-tetramethylpiperidin-1-yl acetate
c) 4-butylamino-2,2,6,6-tetramethylpiperidin-1-yl acetate
d) dibutylamine.

25 g of CHIMASSORB® 2020 (manufacturer: Ciba SC) are converted by a method similar to Example A 49 using acetic anhydride into 25.3 g of polymer 151 which is obtained as a colourless powder; melting point: 154–164° C.

Elemental analysis: 64.48% C, 9.81% H, 15.19% N.

A 52: Polymer (152) of
a) 2,6-diethyl-2,3,6-trimethylpiperidine-1,4-diol
b) terephthalic acid.

2,6-Diethyl-2,3,6-trimethyl-4-hydroxypiperidine N-oxide (for preparation, see German Patent Application 199 49 352.9) is hydrogenated to the corresponding hydroxylamine using a method similar to Example A 10. 10.7 g (0.05 mol) of this hydroxylamine are dissolved in 100 ml of pyridine, and 10.15 g (0.05 mol) of terephthalic dichloride are slowly added dropwise to this solution. The mixture is stirred under nitrogen at 30° C. for 20 hours. 1.9 ml of acetic anhydride are added and after 1 hour the mixture is diluted with 500 ml of water. The precipitate formed is filtered off with suction, washed with water and dried. This gives 17.8 g of polymer 152 which is obtained in the form of a colourless powder; melting point: 190–210° C.

Elemental analysis: 65.17% C, 7.71% H, 3.45% N.

A 53: Polymer (153) of:
a) 2,6-diethyl-2,3,6-trimethylpiperidine-1,4-diol
b) isophthalic acid.

Using a method analogous to Example A 52, 11.8 g (0.055 mol) of 2,6-diethyl-2,3,6-trimethyl-1,4-dihydroxypiperidine and 11.15 g (0.055 mol) of isophthalic dichloride are converted into 19.55 g of polymer 153 which is obtained in the form of a colourless powder; melting point: 206–215° C.

$^1$H-NMR (300 MHz, CDCl$_3$): 8.73 bs, 8.72 bs, 5.65–5.17 m, 2.59–0.64 m.

A 54: Polymer (154) of
a) 2,6-diethyl-2,3,6-trimethylpiperidine-1,4-diol
b) isophthalic acid
c) terephthalic acid.

Using a method analogous to Example A 49, 11.8 g (0.055 mol) of 2,6-diethyl-2,3,6-trimethyl-1,4-dihydroxypiperidine, 5.57 g (0.0275 mol) of terephthalic dichloride and 5.57 g (0.0275 mol) of isophthalic dichloride are converted into 16.85 g of polymer 154 which is obtained as a colourless powder; melting point: 212–218° C.

$^1$H-NMR (300 MHz, CDCl$_3$): 8.74 bs, 8.28 bs, 8.16 bs, 7.62 bs, 5.64–5.05 m, 2.68–0.74 m.

A-55: Polymer (155) of
a) 2,6-diethyl-2,3,6-trimethylpiperidine-1,4-diol
b) adipic acid.

Using a method analogous to Example A 49, 11.8 g (0.055 mol) of 2,6-diethyl-2,3,6-trimethyl-1,4-dihydroxypiperidine and 10.08 g (0.055 mol) of adipoyl dichloride are converted into 16.1 g of polymer 155 which is obtained as a colourless, viscous oil.

$^1$H-NMR (300 MHz, CDCl$_3$): 5.29–4.80 m, 4.28–3.91 m, 2.55–0.77 m.

A-56: Polymer (156) of
a) 2,6-diethyl-2,3,6-trimethylpiperidine-1,4-diol
b) adipic acid
c) terephthalic acid.

Using a method analogous to Example A-49 11.8 g (0.055 mol) of 2,6-diethyl-2,3,6-trimethyl-1,4-dihydroxypiperidine, 5.57 g (0.0275 mol) of terephthalic dichloride and 5.03 g (0.0275 mol) of adipoyl dichloride are converted into 15.1 g of polymer 156 which is obtained as a colourless, amorphous solid; melting point: 112–120° C.

$^1$H-NMR (300 MHz, CDC): 8.13 m, 5.66–4.88 m, 2.37–0.77 m.

A-57: 4-Acetoxyimino-2,6-diethyl-2,3,6-trimethylpiperidin-1-yl acetate (157)

39.5 g (0.2 mol) of 2,6-diethyl-2,3,6-trimethyl-4-oxopiperidine (for preparation, see U.S. Pat. No. 4,131,599) in 40 ml of methanol are heated with 14.55 g of 50% aqueous hydroxylamine solution at 50° C. for 4 hours. The mixture is evaporated on a rotary evaporator, the residue is dissolved in 100 ml of toluene and washed 3× with 50 ml of water. 0.2 g of 4-dimethylaminopyridine and 20.8 ml (0.22 mol) of acetic anhydride are subsequently added and the mixture is stirred at 30° C. for 2 hours. It is then washed with aqueous NaHCO$_3$ solution, dried over magnesium sulfate and evaporated. This gives 34.95 g of 2,6-diethyl-2,3,6-trimethyl-4-acetoxyiminopiperidine.

25.45 g (0.1 mol) of this compound are dissolved in 100 ml of ethyl acetate and slowly added dropwise to 29.9 ml of 40% peracetic acid (40% in acetic acid). After stirring for 21 hours at room temperature, the mixture is washed with water and aqueous NaHCO$_3$ solution, dried over magnesium sulfate and evaporated. This gives 25.7 g of 2,6-diethyl-2,3,6-trimethyl-4-acetoxyiminopiperidine 1-oxide which is converted by a method similar to Example 30 into the compound 157 which is obtained in the form of a colourless oil.

CI-MS for C$_{16}$H$_{28}$N$_2$O$_4$ (312.41): found MH$^+$: 313.

A-58: 4-Acetoxy-2,2,6,6-tetramethylpiperidin-1-yl stearate (158)

2,2,6,6-Tetramethylpiperidin-4-yl acetate 1-oxide (for preparation, see DE-A-4,219,459) is reduced to the hydroxylamine derivative using a method analogous to Example A-10. Acylation with stearyl chloride by a method analogous to Example A-1 gives the title compound which is obtained in the form of colourless crystals; melting point: 55–58° C.

$^1$H-NMR (CDCl$_3$, 300 MHz): 5.11–5.04 m (1H), 2.37–2.32 t (2H), 2.03 s (Me), 1.94–0.86 m (49H).

A-59: 2,2,6,6-Tetramethyl-1-stearoyloxypiperidin-4-yl stearate (159)

2,2,6,6-Tetramethylpiperidin-4-yl stearate 1-oxide (for preparation, see WO 99/67298) is converted by a method similar to Example A-69 into the compound 159 which is obtained in the form of colourless crystals; melting point: 62–65° C.

$^1$H-NMR (CDCl$_3$, 300 MHz): 5.09–5.05 m (1H), 2.36–2.32 t (2H), 2.28–2.24 t (2H), 1.92–0.86 m (82H).

A-60: 4-Acetoxy-2,2,6,6-tetramethylpiperidin-1-yl 3-phenylacrylate (160)

2,2,6,6-Tetramethylpiperidin-4-yl acetate 1-oxide (for preparation, see DE-A-4,219,459) is reduced to the hydroxylamine derivative using a method analogous to Example 10. Acylation with cinnamoyl chloride using a method similar to Example A-1 gives the title compound which is obtained in the form of colourless crystals; melting point: 130–132° C.

$^1$H-NMR (CDCl$_3$, 300 MHz): 7.79–7.74 d (1H), 7.58–7.55 m (2H), 7.44–7.40 m (3H), 6.51–6.46 d (1H), 5.17–5.07 m (1H), 2.03 s (Me), 1.98–1.77 m (4H), 1.31 s (2×Me), 1.5 s (2×Me).

A-61: 4-Acetoxy-2,2,6,6-tetramethylpiperidin-1-yl adamantane-1-carboxylate (161)

2,2,6,6-Tetramethylpiperidin-4-yl acetate 1-oxide (for preparation, see DE-A-4,219,459) is reduced to the hydroxylamine derivative using a method similar to Example 10. Acylation with adamantane-1-carboxylic chloride by a method similar to Example A-1 gives the title compound (161) which is obtained in the form of colourless crystals; melting point: 132–134° C.

$^1$H-NMR (CDCl$_3$, 300 MHz): 5.13–5.02 m (1H), 2.35–1.70 m (19H), 2.03 s (Me), 1.26 s (2×Me), 1.06 s (2×Me).

A-62: 1-Acetoxy-2,2-diethyl-6,6-dimethylpiperidin-4-yl stearate (162)

2,2-Diethyl-6,6-dimethyl-4-hydroxypiperidine N-oxide (for preparation, see German Patent Application 199 49 352.9) is esterified with stearoyl chloride using a method similar to Example A-1 and hydrogenated to the corresponding hydroxylamine using a method similar to Example A 10. The crude hydroxylamine is converted by acetylation using a method similar to Example A 1 into the title compound which is obtained in the form of colourless crystals; melting point: 41–44° C.

$^1$H-NMR (CDCl$_3$, 300 MHz): 5.10–5.02 m (1H), 2.30–2.25 t (2H), 2.06 s (Me), 1.98–0.86 m (53H).

A-63: 9,10-Dinonyl-octadecanedioic acid bis(1-acetoxy-2,2,6,6-tetramethyl-piperidin-4-yl) ester (163)

A mixture consisting of 114 g (0.2 mol) 9,10-dinonyl-octadecanedioic acid, 44 ml (0.4 mol) thionyl chloride and 0.1 ml DMF is slowly heated to 65° C. and stirred at this temperature until the evolution of gas has slowed down (3–4 h). 300 ml toluene are added. 100 ml toluene and and excess thionyl chloride are removed at the reduced pressure of 100 mbar. 292.1 g of a brown solution are obtained which contains 0.2 mol 9,10-dinonyl-octadecanedioyl dichloride.

4-Hydroxy-2,2,6,6-tetramethyl-piperidin-1-oxide is converted to the diester with the acid chloride of above in the presence of the base pyridine. The diester is then converted to the hydroxylamine by hydration according to the method of Example A-10. The raw hydroxylamine is then converted by acetylation into the title compound which is isolated as a yellowish oily liquid.

¹H-NMR (CDCl₃, 300 MHz): 5.12–5.04 m (2H), 2.28–2.25 t (4H), 2.1 s (6H), 2.04–0.83 m (96H).

A-64: 9,10-Dinonyl-octadecanedioic acid bis(1-acetoxy-2,6-diethyl-2,3,6-trimethyl-piperidin-4-yl) ester (164)

The title compound is obtained in a manner analogous to Example A-63 from 2,6-diethyl-4-hydroxy-2,3,6-trimethylpiperidine N-oxide and is isolated as a yellowish oily liquid.

¹H-NMR (CDCl₃, 300 MHz): 5.32–4.91 m (2H), 2.32–0.83 m (118H).

The structural formulae of these compounds are shown in Table 1 below:

TABLE 1

| Example No. | Compound No. | Structural formula |
|---|---|---|
| A1 | 101 | |
| A2 | 102 | |
| A3 | 103 | |
| A4 | 104 | |
| A5 | 105 | |
| A6 | 106 | |

TABLE 1-continued

| Example No. | Compound No. | Structural formula |
|---|---|---|
| A7 | 107 | |
| A8 | 108 | |
| A9 | 109 | |
| A10 | 110 | |
| A11 | 111 | |
| A12 | 112 | |

TABLE 1-continued

| Example No. | Compound No. | Structural formula |
|---|---|---|
| A13 | 113 | |
| A14 | 114 | |
| A15 | 115 | |
| A16 | 116 | |
| A17 | 117 | |
| A18 | 118 | |

TABLE 1-continued

| Example No. | Compound No. | Structural formula |
|---|---|---|
| A19 | 119 | |
| A20 | 120 | |
| A21 | 121 | |
| A22 | 122 | |
| A23 | 123 | |
| A24 | 124 | |

TABLE 1-continued

| Example No. | Compound No. | Structural formula |
|---|---|---|
| A25 | 125 | |
| A26 | 126 | |
| A27 | 127 | |
| A28 | 128 | |
| A29 | 129 | |
| A30 | 130 | |
| A31 | 131 | |

TABLE 1-continued
| Example No. | Compound No. | Structural formula |
|---|---|---|
| A32 | 132 | 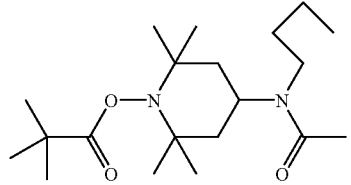 |
| A33 | 133 | 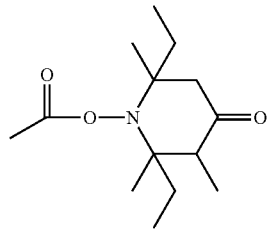 |
| A34 | 134 | 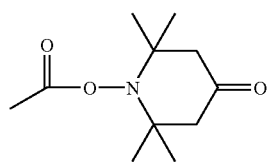 |
| A35 | 135 | 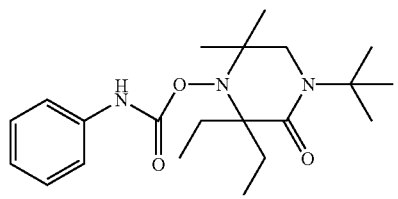 |
| A36 | 136 | 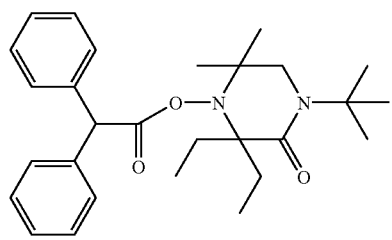 |
| A37 | 137 | 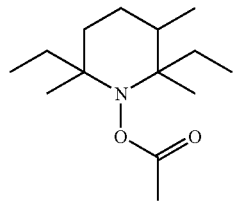 |
| A38 | 138 | 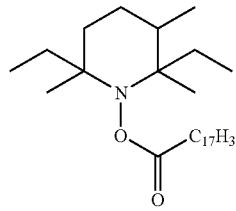 |

TABLE 1-continued
| Example No. | Compound No. | Structural formula |
|---|---|---|
| A39 | 139 | 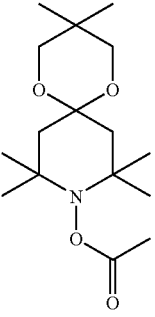 |
| A40 | 140 | 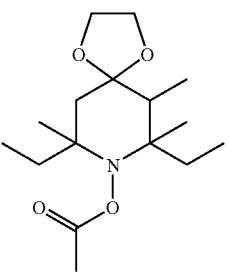 |
| A41 | 141 | 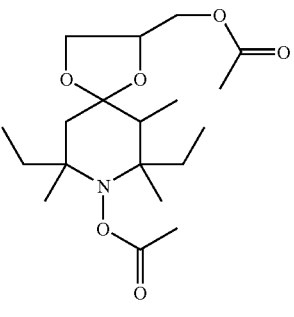 |
| A42 | 142 | 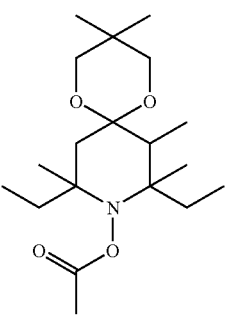 |

TABLE 1-continued

| Example No. | Compound No. | Structural formula |
| --- | --- | --- |
| A43 | 143 | |
| A44 | 144 | |
| A45 | 145 | |
| A46 | 146 | |

TABLE 1-continued
| Example No. | Compound No. | Structural formula |
|---|---|---|
| A47 | 147 | 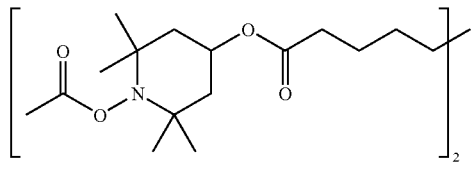 |
| A48 | 148 | 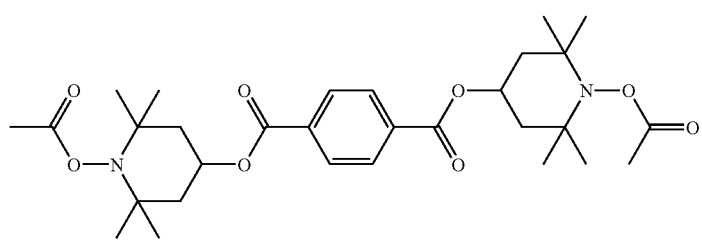 |
| A49 | 149 | 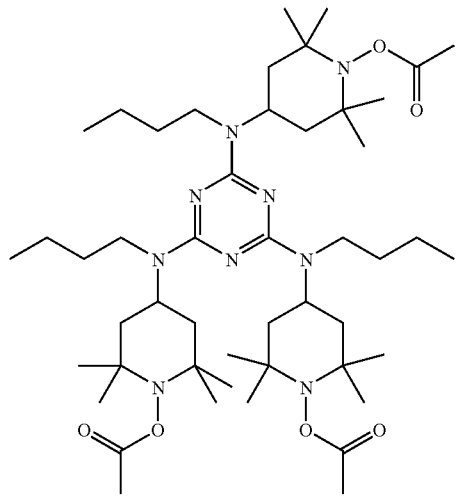 |
| A50 | 150 | Polymer of 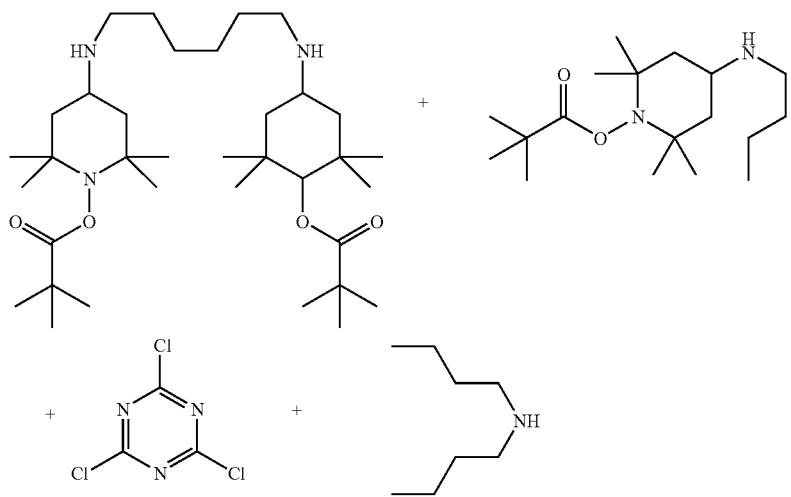 |

TABLE 1-continued
| Example No. | Compound No. | Structural formula |
|---|---|---|
| A50 | 150 | Polymer OF 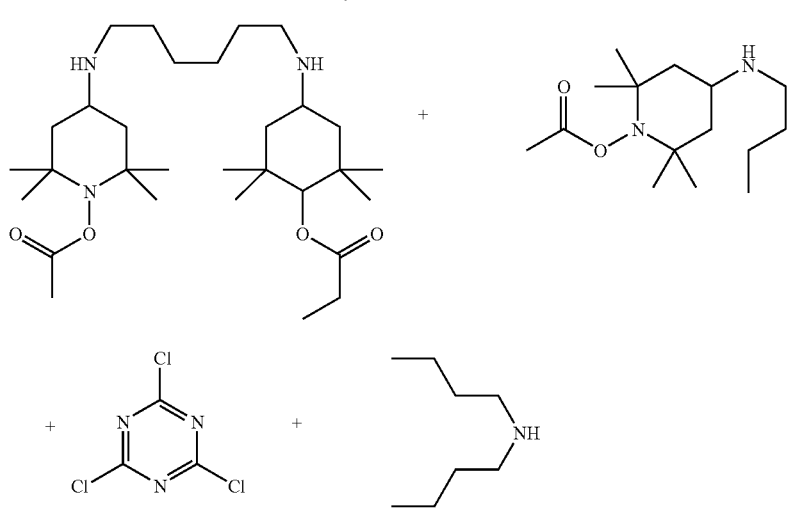 |
| A51 | 151 | Polymer of 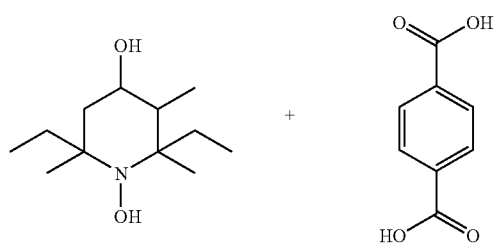 |
| A52 | 152 | Polymer of 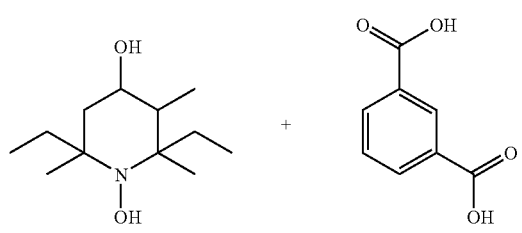 |
| A53 | 153 | Polymer of 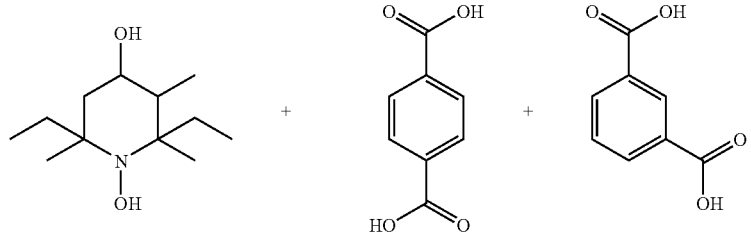 |

TABLE 1-continued

| Example No. | Compound No. | Structural formula |
|---|---|---|
| A54 | 154 | Polymer of 4-hydroxy-2,6-diethyl-2,3,6-trimethyl-1-hydroxypiperidine + terephthalic acid + isophthalic acid |
| A55 | 155 | Polymer of 4-hydroxy-2,6-diethyl-2,3,6-trimethyl-1-hydroxypiperidine + adipic acid |
| A56 | 156 | Polymer of 4-hydroxy-2,6-diethyl-2,3,6-trimethyl-1-hydroxypiperidine + terephthalic acid + adipic acid |
| A57 | 157 | 1-acetoxy-4-(acetoxyimino)-2,6-diethyl-2,3,6-trimethylpiperidine |
| A58 | 158 | 4-acetoxy-1-(long-chain acyloxy)-2,2,6,6-tetramethylpiperidine |

TABLE 1-continued
| Example No. | Compound No. | Structural formula |
|---|---|---|
| A59 | 1159 | 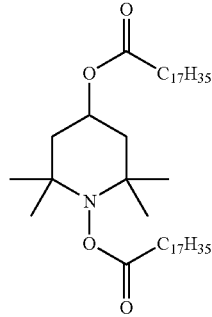 |
| A60 | 160 | 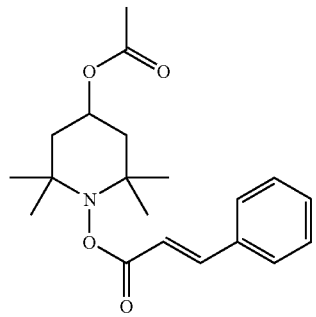 |
| A61 | 161 | 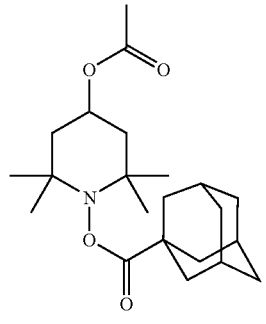 |
| A62 | 162 | 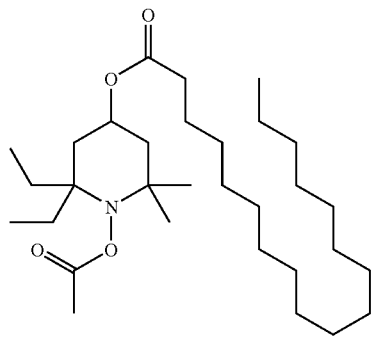 |

TABLE 1-continued

| Example No. | Compound No. | Structural formula |
|---|---|---|
| A63 | 163 | 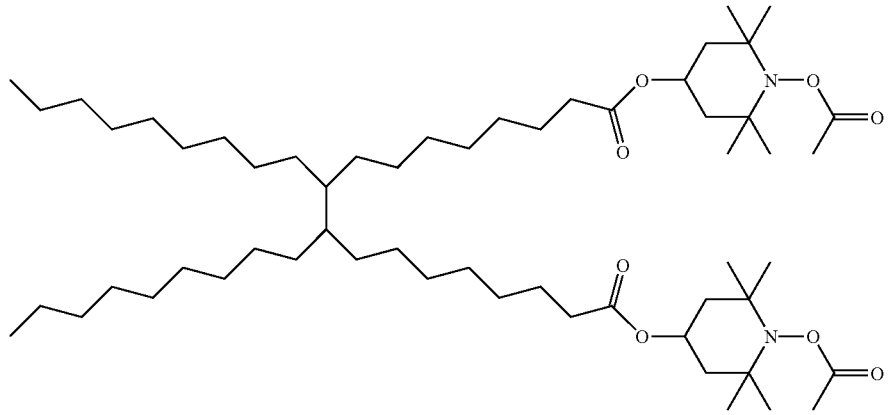 |
| A64 | 164 | 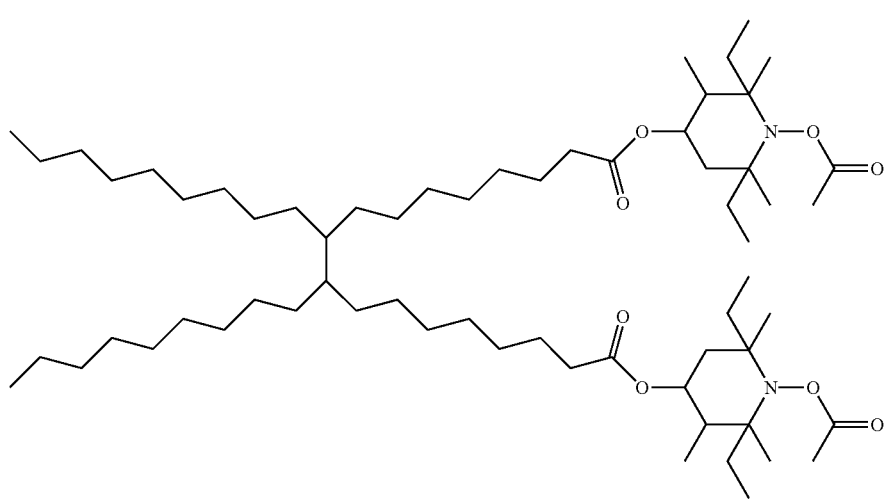 |

USE EXAMPLES

B) Polymerization Examples Using Selected Compounds from Table 1

Materials and Methods:
- All solvents and monomers are distilled under argon or under reduced pressure via a Vigreux column shortly before use.
- All reaction mixtures are freed of oxygen by purging with argon using the freeze/thaw technique and subsequently maintained under argon gas prior to the polymerization.
- The reactants are in the form of a clear homogeneous solution before commencement of the polymerization reaction.
- The monomer conversion is determined by weighing the residue after evaporation of unreacted monomer at 80° C. and 0.27 mbar for 20 hours and after the initiator used has been taken off.
- The polymers are characterized by GPC (gel permeation chromatography) and/or MALDI-MS (matrix assisted laser desorption ionization mass spectrometry).
- GPC: a two-piston production model pump RHEOS 4000 from FLUX INSTRUMENTS (represented by Ercatech AG, Bern, Switzerland) is used. The pump output is 1 ml/min. The chromatography is carried out on two PIgel 5 µm mixed-C columns from POLYMER INSTRUMENTS, Shropshire UK connected in series at 40° C. in THF. These columns are calibrated using polystyrene having $M_n$ values in the range from 200 to 2 000 000. The fractions are measured using an RI detector ERC-7515A from ERCATECH AG at 30° C.
- MALDI-MS: the measurements were carried out on a linear TOF (time of flight) MALDI-MS LDI-1700 from Linear Scientific Inc., Reno, USA. The matrix used is 2,5-dihydroxybenzoic acid, and the laser wavelength is 33 nm.

B 1: Polymerization of n-butyl Acrylate Using the Compound 101 at 145° C.

319 mg (1.17 mmol) of the compound 101 and 10 g (78 mmol) of n-butyl acrylate are placed in a 50 ml three-necked round-bottom flask provided with thermometer, condenser and magnetic stirrer and the mixture is degassed. The clear solution is heated to 145° C. under argon. It is stirred for another 1 hour at 145° C. cooled to 60° C. and the residual monomer is evaporated in a high vacuum. After conversion of 4 g (40%) of the monomer, a clear, colourless, viscous liquid is obtained. GPC: $M_n$=70 000, $M_w$=182 000, PD=2.6.

B 2: Polymerization of n-butyl Acrylate Using the Compound 101 at 120° C.

Starting mix: see Example B 1.

The clear solution is heated to 120° C. under argon. The mixture is stirred for another 2 hours at 120° C., cooled to 60° C. and the residual monomer is evaporated in a high vacuum. After conversion of 5 g (50%) of the monomer, a clear, colourless, viscous liquid is obtained. GPC: $M_n$=91 000, $M_w$=500 500, PD=5.5.

B 3: Polymerization of n-butyl Acrylate Using the Compound 102 at 145° C.

391 mg (1.17 mmol) of the compound 102 and 10 g (78 mmol) of n-butyl acrylate are placed in a 50 ml three-necked round-bottom flask provided with thermometer, condenser and magnetic stirrer and the mixture is degassed. The clear solution is heated to 145° C. under argon. It is stirred for another 2 hours at 145° C. cooled to 60° C. and the residual monomer is evaporated in a high vacuum. After conversion of 5.9 g (59%) of the monomer, a clear, colourless, viscous liquid is obtained. GPC: $M_n$=184 300, $M_w$=681 900, PD=3.7.

B 4: Polymerization of n-butyl Acrylate Using the Compound 123 at 130° C.

382 mg (1.17 mmol) of the compound 123 and 10 g (78 mmol) of n-butyl acrylate are placed in a 50 ml three-necked round-bottom flask provided with thermometer, condenser and magnetic stirrer and the mixture is degassed. The clear solution is heated to 130° C. under argon. It is stirred for another 5 hours at 130° C. cooled to 60° C. and the residual monomer is evaporated in a high vacuum. After conversion of 4.0 g (40%) of the monomer, a clear, colourless, viscous liquid is obtained. GPC: $M_n$=41 000, $M_w$=492 000, PD=12.0.

B 5: Polymerization of n-butyl Acrylate Using the Compound 124 at 110° C.

455 mg (1.17 mmol) of the compound 124 and 10 g (78 mmol) of n-butyl acrylate are placed in a 50 ml three-necked round-bottom flask provided with thermometer, condenser and magnetic stirrer and the mixture is degassed. The clear solution is heated to 110° C. under argon. It is stirred for another 2.5 hours at 110° C. cooled to 60° C. and the residual monomer is evaporated in a high vacuum. After conversion of 4.5 g (40%) of the monomer, a clear, colourless, viscous liquid is obtained. GPC: $M_n$=160 000, $M_w$=560 000, PD=3.5.

B 6: Polymerization of n-butyl Acrylate Using the Compound 125 at 100° C.

431 mg (1.17 mmol) of the compound 125 and 10 g (78 mmol) of n-butyl acrylate are placed in a 50 ml three-necked round-bottom flask provided with thermometer, condenser and magnetic stirrer and the mixture is degassed. The clear solution is heated to 100° C. under argon. It is stirred for another 3 hours at 100° C. cooled to 60° C. and the residual monomer is evaporated in a high vacuum. After conversion of 8.0 g (80%) of the monomer, a clear, colourless, viscous liquid is obtained. GPC: $M_n$=7 500, $M_w$=157 500, PD=21.0.

B 7 Polymerization of n-butylacrylate Using the Compound 152 at 145° C.

Starting Mix: 1.5 mol % 152 in n-butylacrylate (Bulk)

The clear solution is heated to 145° C. under argon. An immediate, strong exothermic reaction is observed. After conversion of 68.5% of the monomer, a clear, colourless, viscous liquid is obtained. GPC: $M_n$=28 525, PD=3.55.

B 7 Polymerization of n-butylacrylate Using the Compound 152 at 100° C.

Starting Mix: 1.5 mol % 152 in n-butylacrylate (Bulk)

The clear solution is heated to 100° C. under argon. After conversion of 5% of the monomer within 5 hours, a clear, colourless, viscous liquid is obtained. GPC: $M_n$=3550, PD=1.5.

B 7 Polymerization of n-butylacrylate Using the Compound 139 at 145° C.

Starting Mix: 1.5 mol % 152 in n-butylacrylate (Bulk)

The clear solution is heated to 145° C. under argon. After conversion of 32% of the monomer within 3 hours, a clear, colourless, viscous liquid is obtained. GPC: $M_n$=76 830, PD=4.7.

C) Controlled Degradation of Polypropylene by Means of NOR Compounds

General Procedure

Unless stated otherwise, commercial polypropylene (Profax® 6501, manufacturer: Montell) is extruded on a twin-screw extruder ZSK 25 from Werner & Pfleiderer at a temperature of $T_{max}$=270° C. (heating zones 1–6), a throughput of 4 kg/h and 100 rpm with addition of basic-level stabilization and the additives indicated in Tables 1–13, granulated in a water bath. The melt viscosity (MFR) is determined in accordance with ISO 1133. A large increase in the melt flow rate indicates substantial chain degradation.

Under the processing conditions indicated, addition of an NOR compound results in the PP used undergoing increased degradation, which is reflected in higher MFR values compared with the starting polymer (or the comparative examples). In contrast to the alkylated hydroxylamines, the hydroxylamine esters used according to the invention produce considerably greater polymer degradation (higher MFR values) at the same use concentration. Unless stated otherwise, the additives are made up of the test compound and in each case 0.1% of IRGANOX B 225, and 0.05% of calcium stearate. IRGANOX B 225 is a 1:1 mixture of Irgafos®168 and IRGANOX 1010.

TABLE 2

| Example | Additives | MFR (230/2.16) | MFR (190/2.16) |
| --- | --- | --- | --- |
| C 1*) | 0.1% IRGANOX B 225 0.05% of calcium stearate | 8.1 | 3.4 |
| C 2*) | 0.20% NOR 1 | 36.5 | 16.2 |
| C 3*) | 0.20% NOR 2 | 31.5 | 14.1 |
| C 4*) | 0.20% NOR 3 | 39.1 | 17.8 |
| C 5*) | 0.20% NOR 4 | 41.1 | 16.8 |
| C 6*) | 0.05% NOR 4 | 25.3 | 11.6 |
| C 7 | 0.20% 105 | >300 | 180 |
| C 8 | 0.05% 105 | 145 | 57.3 |
| C 9 | 0.05% 107 | 160 | 66.8 |
| C 10 | 0.05% 119 | >300 | 360 |
| C 11 | 0.05% 122 | 280 | 125 |

*)Comparison; Polymer: density = 0.79 g/cm$^3$; MFR$_{230/2.16}$ = 6.4 g/10 min

Compounds of the prior art used for the comparative experiments reported in Table 2:

NOR 1:
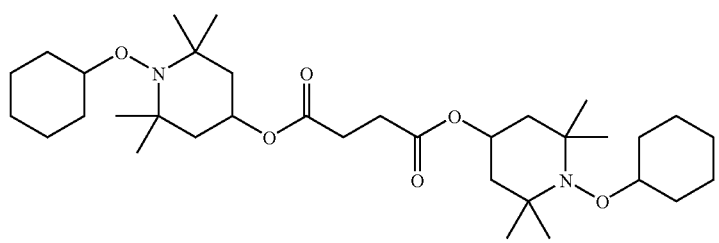

NOR 2:
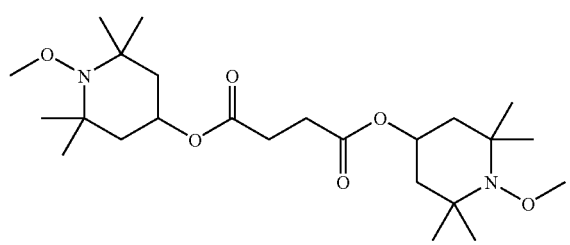

NOR 3:
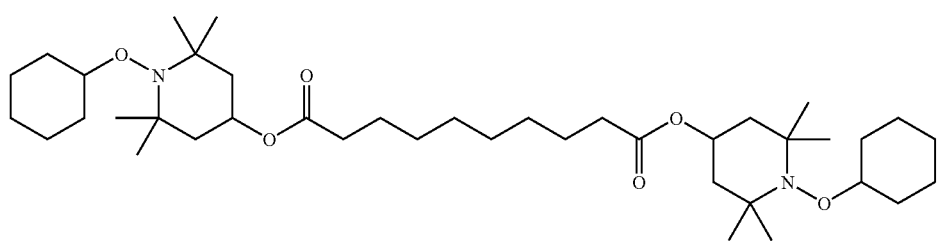

NOR 4:
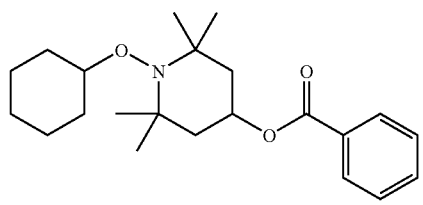

TABLE 3

| Example | Additives | MFR (230/2.16) |
|---|---|---|
| C 12 (Comparison) | 0.1% IRGANOX B 225 0.05% calcium stearate | 8.2 |
| C 12 | 0.2% 102 | 97.4 |
| C 13 | 0.2% 101 | 45.7 |

Polymer: density = 0.79 g/cm³; MFR$_{230/2.16}$ = 7.1 g/10 min.

TABLE 4

| Example | Additives | MFR (230/2.16) |
|---|---|---|
| C 14 (Comparison) | 0.1% IRGANOX B 225 0.05% calcium stearate | 7.9 |
| C 15 | 0.05% 106 | 67.1 |
| C 16 | 0.05% 109 | 44.9 |
| C 17 | 0.05% 123 | 75.0 |
| C 18 | 0.05% 113 | 46.0 |

Polymer: density = 0.79 g/cm³; MFR$_{230/2.16}$ = 6.8 g/10 min

TABLE 5

| Example | Additives | MFR (230/2.16) |
|---|---|---|
| C 19 (Comparison) | 0.1% IRGANOX B 225 0.05% calcium stearate | 8.2 |
| C 20 | 0.025% 106 | 78.8 |
| C 21 | 0.05% 106 | 184 |
| C 22 | 0.025% 120 | 343 |
| C 23 | 0.05% 106 | >>300 |

Polymer: density = 0.79 g/cm³; MFR$_{230/2.16}$ = 6.1 g/10 min

TABLE 6

Degradation of polypropylene by means of NOR-compounds at 250° C.

| Example | Additives | MFR* (230/2.16) |
|---|---|---|
| C 24 (Comparison) | 0.1% IRGANOX B 225[1] 0.05% calcium stearate | 6.2 |
| C 25 | 0.05% 106[1] | 17.0 |
| C 26 | 0.05% 129 | 14.4 |

TABLE 6-continued

Degradation of polypropylene by means of NOR-compounds at 250° C.

| Example | Additives | MFR* (230/2.16) |
|---|---|---|
| C 27 | 0.05% 128 | 15.5 |
| C 28 | 0.05% 132 | 15.4 |

Polymer: density = 0.79 g/cm$^3$; MFR$_{230/2.16}$ = 6.1 g/10 min

Preparation of Concentrates

Synthesis of Concentrates with Subsequent Degradation

The steps during extrusion are the same as in the general procedure (zone 1=35° C., zone 2=130° C., zone 3=170° C., zone 4=170° C., zone 5=170° C., zone 6=165° C.; polypropylene Profax® 6501, Montell). The addition of mineral oil (white oil) is a general method of improving homogenization of the additives.

TABLE 7

| Concentrate | Additives |
|---|---|
| K 1 | 2.00% 120 |
| K 2 | 1.00% mineral oil |
|  | 2.00% 120 |
| K 3 | 2.00% 106 |
| K 4 | 1.00% mineral oil |
|  | 2.00% 106 |

Polymer Degradation

The steps in extrusion are the same as in the general procedure (heating zones 1–6, T$_{max}$: 250° C.; polypropylene Profax® 6501, Montell).

TABLE 8

| Example | Additives | MFR (230/2.16) |
|---|---|---|
| Comparative Example | 0.10% IRGANOX B225 0.05% calcium stearate | 8.1 |
| C 29 | 1.25% K 1 | 39 |
| C 30 | 1.25% K 2 | 50 |
| C 31 | 1.25% K 3 | 20 |
| C 32 | 1.25% K 4 | 21 |

Sequential Degradation of Polypropylene

The steps during extrusion are the same as in the general procedure. In the first extrusion step, the polymer is extruded at 230° C. (heating zones 1–6, T$_{max}$=230° C.) and granulated. The extrudate is subsequently extruded again at 270° C. (heating zones 1–6, T$_{max}$: 270° C.; polypropylene Profax® 6501, Montell). The melt viscosities after the two extrusion steps are listed in Table 9.

TABLE 9

| Example | Additives | MFR (190/2.16)[1] | MFR (190/2.16)[2] |
|---|---|---|---|
| Comparative Example | 0.10% IRGANOX B225 0.05% calcium stearate | 1.7 | 2.7 |
| C 33 | 0.025% 106 | 2.4 | 6.1 |
| C 34 | 0.025% 120 | 4.6 | 27 |
| C 35 | 0.025% 106 0.025% 120 | 3.8 | 31 |
| C 36 | 0.025% 106 0.025% DTBPH | 7.1 | 15 |
| C 37 | 0.025% 120 0.025% DTBPH | 9.6 | 52 |

[1] after 1st extrusion;
[2] after 2nd extrusion;
[3] DTBPH: 2,5-bis-tert-butylperoxy-2,5-dimethylhexane Sequential Degradation of Polypropylene The steps in the extrusion are the same as in the general procedure (heating zones 1–6, T$_{max}$: 250° C.; polypropylene Profax® 6501, Montell). The hydroxylamine ester is added as a mixture in mineral oil.

TABLE 10

| Example | Additives | MFR (190/2.16) |
|---|---|---|
| C 38 | 0.10% IRGANOX B225 0.05% calcium stearate 0.25% mineral oil 0.025% 106 | 40 |
| C 39 | 0.10% IRGANOX 8225 0.05% calcium stearate 0.25% mineral oil 0.025% 120 | 76 |

Controlled Degradation Using Further NOR Compounds

The steps in the extrusion are the same as in the general procedure (heating zones 1–6, T$_{max}$: 250° C.; polypropylene Profax® 6501, Montell). The different amounts of additives mixed in result from a correction factor which takes account of the different molecular weights.

TABLE 11

| Example | Additives | MFR (190/2.16) |
|---|---|---|
| C 40 | 0.051% 150 | 55 |
| C 41 | 0.029% 142 | 31 |
| C 42 | 0.04% 140 | 52 |
| C 43 | 0.033% 143 | 50 |
| C 44 | 0.062% 144 | 62 |
| C 45 | 0.047% 145 | 16 |
| C 46 | 0.036% 141 | 42 |
| C 47 | 0.025% 152 | 23 |
| C 48 | 0.025% 155 | 74 |

Addition of Metal Salts

The steps in the extrusion are the same as in the general procedure (heating zones 1–6, T$_{max}$: 250° C.; polypropylene Profax® 6501, Montell). The addition of metal salts leads to improved MFR values at lower extrusion temperatures.

TABLE 12

| Example | Additives | MFR (230/2.16) |
|---|---|---|
| C 49 | 0.025% 120 | 9.5 |
| C 50 | 0.025% 120 0.10% of calcium oxide | 38 |
| C 51 | 0.025% 120 0.10% calcium carbonate | 39 |
| C 52 | 0.025% 120 0.10% zinc oxide | 41 |

Addition of Nitroxyl Radicals

The steps in the extrusion are the same as in the general procedure (heating zones 1–6, $T_{max}$: 250° C.; polypropylene Novolen® from Targor). The addition of metal salts reduces the degradation rate slightly and leads to polymers having improved melt properties.

TABLE 13

| Example | Additives | MFR (230/2.16) |
|---|---|---|
| C 53 | 0.10% IRGANOX B225 0.05% calcium stearate | 38 |
| C 54 | 0.025% 120 | 27 |
| C 55 | 0.025% 120 0.0021% nitroxyl A | 39 | nitroxyl A: bis(1-oxyl-2,2,6,6-tetramethylpiperidin-4-yl) decanedioate, Prostab ® 5415 (Ciba SC)

D: Controlled Increase in the Molecular Weight of Polyethylene

General Procedure 36 g of polyethylene (Lupolen® 1812 E, Elenac GmbH) are kneaded for 10 minutes under a nitrogen atmosphere in a Brabender mixer W 50 maintained at 220° C. (40 rpm). The additives are introduced into the mixing chamber at the beginning together with the polyethylene. After a reaction time of 10 minutes, mixing is stopped, the polymer composition is taken from the mixing chamber and prepressed at about 50 KN for 1 minute at 220° C. After comminution of the sample, the melt viscosity (MFR) is determined in accordance with ISO 1133.

The polymer used suffers a molecular weight decrease (greater MFR than in the case of the starting material RY 653) under process conditions (no additive, Example D1). In contrast to the comparative example, an increase in the molecular weight, expressed by a decrease in the MFR value, occurs in the example according to the invention (D2).

TABLE 14

Increase in the molecular weight of polyethylene

| Example | Additives | MFR (190° C./21.6) |
|---|---|---|
| D1 (Comparative Example) | — | 39.8 |
| D2 | 1.0% compound 120 | 19.9 |

*Polymer: density = 0.77 g/cm³; $MFR_{190/21.6}$ = 34 g/10 min

Extrusion

Commercial polyethylene (Hostalen® GB7250, Hoechst) is extruded on a twin-screw extruder ZSK 25 from Werner & Pfleiderer at a temperature of $T_{max}$: 270° C. (heating zones 1–6), a throughput of 4 kg/h and 100 rpm with addition of the additives indicated, granulated in a water bath and the melt viscosity (MFR) is determined in accordance with ISO 1133. A decrease in the melt flow rate indicates an increase in the chain length (increase in the molecular weight).

Under the processing conditions employed, the HDPE used experiences an increase in the molecular weight as a result of the addition of a hydroxylamine ester, which is reflected in lower MFR values compared with the comparative example.

TABLE 15

| Example | Additives | MFR (190° C./21.6) |
|---|---|---|
| D3 (Comparative Example) | — | 7.2 |
| D4 | 0.05% 120 | 6.3 |

*Polymer: density = 0.77 g/cm³; $MFR_{190/21.6}$ = 34 g/10 min

What is claimed is:

1. A process for reducing the molecular weight of polypropylene, propylene copolymers or polypropylene blends, said process comprising heating the polypropylene, propylene copolymers or polypropylene blends at a temperature between 160° C. and 280° C. in the presence of at least one hydroxylamine ester or a polymer of a hydroxylamine ester containing the group of the formula:

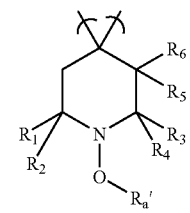

(I)

where
$R_a'$ is a monoacyl or diacyl radical;
$R_1$–$R_4$ are each $C_1$–$C_6$alkyl; and
$R_5$ and $R_6$ are each, independently of one another, hydrogen, $C_1$–$C_6$alkyl or $C_6$–$C_{10}$aryl; or
$R_5$ and $R_6$ are double bonded oxygen.

2. A process according to claim 1, characterised in that said hydroxylamine ester is a compound belonging to the group consisting of sterically hindered amine derivatives of the formula:

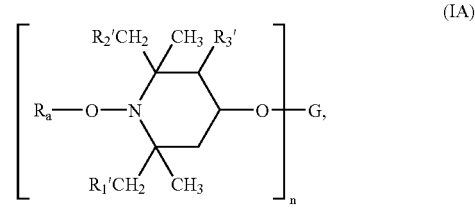

(IA)

where n is an integer from 1 to 4, $R_a$ is acyl and $R_1'$, $R_2'$ and $R_3'$ are each, independently of one another, hydrogen or methyl; and G has the following meanings:
when n=1,
hydrogen, $C_1$–$C_{18}$alkyl which may be interrupted by one or more oxygen atoms, 2-cyanoethyl, benzyl, glycidyl, the monovalent radical of an aliphatic, cycloaliphatic, araliphatic, unsaturated or aromatic carboxylic acid, carbamic acid or phosphorus-containing acid or a monovalent silyl radical, preferably the acyl radical of an aliphatic carboxylic acid having from 2 to 18 C-atoms, of a cycloaliphatic carboxylic acid having from 7 to 15 C-atoms, of an α,β-unsaturated carboxylic acid having from 3 to 5 C-atoms or of an aromatic carboxylic acid having from 7 to 15 C-atoms, where the carboxylic acid may be substituted in the aliphatic, cycloaliphatic or aromatic part by from 1 to 3 —COOZ$^1$ groups, where Z$^1$ is hydrogen, C$_1$–C$_{20}$alkyl, C$_3$–C$_{12}$alkenyl, C$_5$–C$_7$cycloalkyl, phenyl or benzyl; or when n=2, C$_2$–C$_{12}$alkylene, C$_4$–C$_{12}$alkenylene, xylylene, the divalent acid radical of an aliphatic, cycloaliphatic, araliphatic or aromatic dicarboxylic acid, dicarbamic acid or phosphorus-containing acid, or a divalent silyl radical, preferably the acyl radical of an aliphatic dicarboxylic acid having from 2 to 36 C-atoms, of a cycloaliphatic or aromatic dicarboxylic acid having from 8 to 14 C-atoms or of an aliphatic, cycloaliphatic or aromatic dicarbamic acid having from 8 to 14 C-atoms, where the dicarboxylic acid may be substituted in the aliphatic, cycloaliphatic or aromatic part by 1 or 2 —COOZ$^1$ groups, where Z$^1$ is as defined above; or when n=3, the trivalent acid radical of an aliphatic, cycloaliphatic or aromatic tricarboxylic acid, where the radical may be substituted in the aliphatic, cycloaliphatic or aromatic part by —COOZ$^1$, where Z$^1$ is as defined above, or the trivalent acid radical of an aromatic tricarbamic acid or a phosphorus-containing acid, or a trivalent silyl radical; or, when n=4, the tetravalent acid radical of an aliphatic, cycloaliphatic or aromatic tetracarboxylic acid.

3. A process according to claim 2, characterised in that said hydroxylamine ester is a compound of formula (IA), in which n is 1 or 2, R$_1$', R$_2$' and R$_3$' are each hydrogen and R$_a$ is C$_2$–C$_{18}$alkanoyl or C$_3$–C$_6$alkenoyl and G is the acyl radical of an aliphatic monocarboxylic acid having from 12 to 18 C-atoms or the diacyl radical of an aliphatic dicarboxylic acid having from 4 to 12 C-atoms is added.

4. A process according to claim 1, characterised in that said hydroxylamine ester is a compound belonging to the group of sterically hindered amines of the formula:

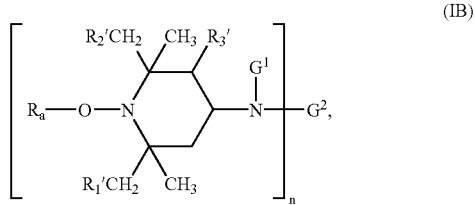

(IB)

where n is 1 or 2 and R$_a$, R$_1$', R$_2$' and R$_3$' are as defined under the formula IA;

G$^1$ is hydrogen, C$_1$–C$_{12}$alkyl, C$_2$–C$_5$hydroxyalkyl, C$_5$–C$_7$cycloalkyl, C$_7$–C$_8$aralkyl, C$_2$–C$_{18}$alkanoyl, C$_3$–C$_5$alkenoyl or benzoyl or a group:

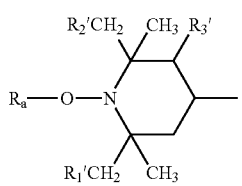

where R$_a$, R$_1$', R$_2$' and R$_3$' are as defined above; and

G$^2$ has the following meanings:

when n=1, hydrogen, C$_1$–C$_{18}$alkyl, C$_3$–C$_8$alkenyl, C$_5$–C$_7$cycloalkyl, C$_1$–C$_4$alkyl which bears a hydroxy, cyano, alkoxycarbonyl or carbamido group as substituent, glycidyl or a group —CH$_2$—CH(OH)-Z or CONH-Z, where Z is hydrogen, methyl or phenyl; or when n=2, C$_2$–C$_{12}$alkylene, C$_6$–C$_{12}$arylene, xylylene or —CH$_2$CH(OH)—CH$_2$— or —CH$_2$—CH(OH)—CH$_2$—O-D-O— group, where D is C$_2$–C$_{10}$alkylene, C$_6$–C$_{15}$arylene, C$_6$–C$_{12}$cycloalkylene;

or, provided that G$^1$ is not alkanoyl, alkenoyl or benzoyl, G$^2$ may also be 1-oxo-C$_2$–C$_{12}$alkylene, the divalent radical of an aliphatic, cycloaliphatic or aromatic dicarboxylic acid or dicarbamic acid or the —CO— group;

or, when n=1, G$^1$ and G$^2$ may together be the divalent radical of an aliphatic, cycloaliphatic or aromatic 1,2-dicarboxylic acid or 1,3-dicarboxylic acid.

5. A process according to claim 1, characterised in that said hydroxylamine ester is a compound belonging to the group of sterically hindered amines of the formula:

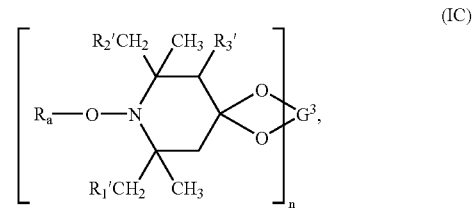

(IC)

where n is 1 or 2 and R$_a$, R$_1$', R$_2$' and R$_3$' are as defined under the formula IA; and G$^3$ is C$_2$–C$_8$alkylene, C$_2$–C$_8$hydroxyalkylene or C$_4$–C$_{22}$acyloxyalkylene when n=1 or is the group (—CH$_2$)$_2$C(CH$_2$—)$_2$ when n=2.

6. A process according to claim 1, characterised in that said hydroxylamine ester is a compound bejonging to the group of sterically hindered amines of the formulae:

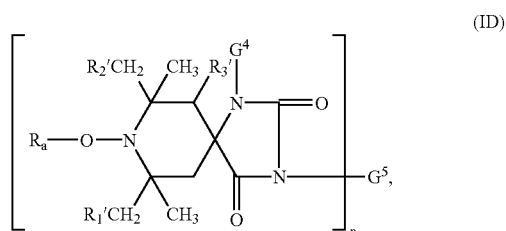

(ID)

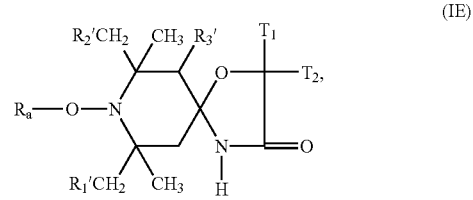

(IE)

-continued

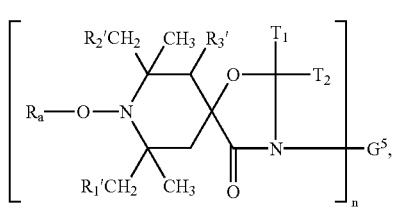

(IF)

where
n is 1 or 2 and $R_a$, $R_1'$, $R_2'$ and $R_3'$ are as defined under the formula IA; and
$G^4$ is hydrogen, $C_1$–$C_{12}$alkyl, allyl, benzyl, glycidyl or $C_2$–$C_6$alkoxyalkyl; and
$G^5$ has the following meanings:
when n=1,
hydrogen, $C_1$–$C_{12}$alkyl, $C_3$–$C_5$alkenyl, $C_7$–$C_9$aralkyl, $C_5$–$C_7$cycloalkyl, $C_2$–$C_4$hydroxyalkyl, $C_2$–$C_6$alkoxyalkyl, $C_6$–$C_{10}$aryl, glycidyl or a group: —$(CH_2)_p$—COO-Q or —$(CH_2)_p$—O—CO-Q, where p is 1 or 2 and Q is $C_1$–$C_4$alkyl or phenyl; or
when n=2,
$C_2$–$C_{12}$alkylene, $C_4$–$C_{12}$alkenylene, $C_6$–$C_{12}$arylene, the group —$CH_2$—CH(OH)—$CH_2$—O-D-O—$CH_2$—CH(OH)—$CH_2$—, where D is $C_2$–$C_{10}$-alkylene, $C_6$–$C_{15}$arylene or $C_6$–$C_{12}$-cycloalkylene, or the group —$CH_2CH(OZ')CH_2$—$(OCH_2$—$CH(OZ')CH_2)_2$—, where Z' is hydrogen, $C_1$–$C_{18}$alkyl, allyl, benzyl, $C_2$–$C_{12}$-alkanoyl or benzoyl;
$T^1$ and $T^2$ are each, independently of one another, hydrogen, $C_1$–$C_{18}$alkyl, $C_6$–$C_{10}$aryl or $C_7$–$C_9$aralkyl, each of which may be substituted by halogen or $C_1$–$C_4$-alkyl, or
$T^1$ and $T^2$ together with the carbon atom connecting them form a $C_5$–$C_{14}$cycloalkane ring.

7. A process according to claim 1, characterised in that said hydroxylamine ester is a compound of the formula:

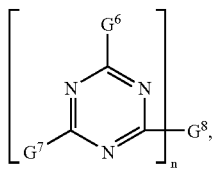

(IG)

where
n=1 or 2 and $G^6$ is a group:

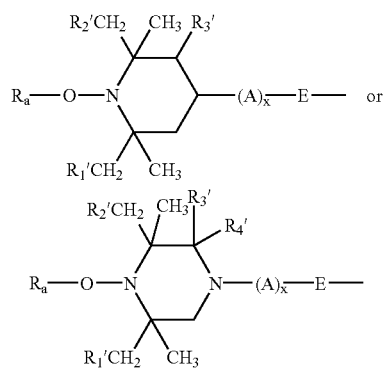

where $R_a$, $R_1'$, $R_2'$ and $R_3'$ are as defined under the formula IA, and $R_3'$ and $R_4'$ are each hydrogen or methyl or together form the substituent =O;
E is —O— or —$NG^1$-,
A is $C_2$–$C_6$-alkylene or —$(CH_2)_3$—O—, and x is either 0 or 1;
$G^1$ is hydrogen, $C_1$–$C_{12}$alkyl, $C_2$–$C_5$hydroxyalkyl or $C_5$–$C_7$cycloalkyl;
$G^7$ is identical to $G^6$ or is one of the groups —$NG^9G^{10}$, —$OG^{11}$, —$NHCH_2OG^{11}$ or —$N(CH_2OG^{11})_2$;
when n=1, $G^8$ is identical to $G^6$ or $G^7$; and,
when n=2, $G^8$ is the group -E-B-E-, where B is $C_2$–$C_8$-alkylene or $C_2$–$C_8$-alkylene interrupted by 1 or 2 —$NG^9$- groups, and $G^9$ is $C_1$–$C_{12}$alkyl, cyclohexyl, benzyl or $C_1$–$C_4$hydroxyalkyl or the groups:

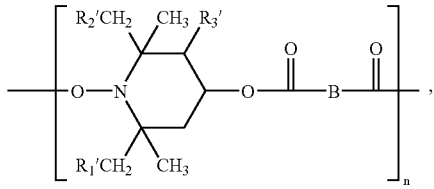

$G^{10}$ is $C_1$–$C_{12}$-alkyl, cyclohexyl, benzyl or $C_1$–$C_4$-hydroxyalkyl, and $G^{11}$ is hydrogen, $C_1$–$C_{12}$-alkyl or phenyl; and
$G^9$ and $G^{10}$ are together $C_4$–$C_5$-alkylene or $C_4$–$C_5$oxaalkylene.

8. A process according to claim 1, characterised in that said hydroxylamine ester is a compound of the formula:

(IH)

$$\left[ \begin{array}{c} R_2'CH_2 \quad CH_3 \quad R_3' \\ \phantom{X} \\ \text{—O—N} \quad \text{—O—} \overset{O}{\underset{\|}{C}} \text{—B—} \overset{O}{\underset{\|}{C}} \\ R_1'CH_2 \quad CH_3 \end{array} \right]_n$$

where n is an integer greater than two and $R_1'$, $R_2'$ and $R_3'$ are as defined under the formula IA; and B is a bivalent substituent.

9. A process for reducing the molecular weight of polypropylene, propylene copolymers or polypropylene blends, said process comprising heating the polypropylene, propylene copolymers or polypropylene blends at a temperature between 160° C. and 280° C. in the presence of at least one hydroxylamine ester of the formula:

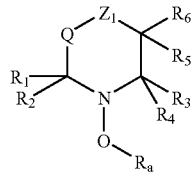

(Ia)

where, $R_a$ is an acyl radical selected from the group consisting of —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl, —C(=O)—N($C_1$–$C_6$alkyl)$_2$, —P(=O)—$C_1$–$C_{19}$alkyl, —P(=O)$_2$—$C_1$–$C_{19}$alkyl, —P(=O)—$C_6$–$C_{10}$aryl, —P=O(—$C_1$–$C_{19}$alkyl)$_2$, —P=O(—$C_6$–$C_{10}$aryl)$_2$, —P(=O)—O—$C_1$–$C_6$alkyl, —P(=O)—O—$C_6$–$C_{10}$aryl, —P=O(—O—$C_1$–$C_6$alkyl)$_2$, —P=O(—O—$C_6$–$C_{10}$aryl)$_2$, —P(—O—$C_1$–$C_6$alkyl)$_2$ and —P(—O—$C_6$–$C_{10}$aryl)$_2$;

$R_1$–$R_4$ are each $C_1$–$C_6$alkyl;

$R_5$ and $R_6$ are each, independently of one another, hydrogen, $C_1$–$C_6$alkyl or $C_6$–$C_{10}$aryl; or $R_5$ and $R_6$ are together oxygen;

Q is a direct bond or a bivalent radical —($CR_7R_8$)— or —($CR_7R_8$—$CR_9R_{10}$)—, where $R_7$, $R_8$, $R_9$ and $R_{10}$ are each, independently of one another, hydrogen or $C_1$–$C_6$alkyl; and $Z_1$ is oxygen or a bivalent radical —$NR_{11}$— or —($CR_{12}R_{13}$)—, where $R_{11}$ is hydrogen, $C_1$–$C_6$alkyl, $C_6$–$C_{10}$aryl or the acyl radical $R_a$ as defined above; or, independently of one another, $R_{12}$ and $R_{13}$ are each hydrogen or $C_1$–$C_6$alkyl, or one of the radicals $R_{12}$ and $R_{13}$ is hydrogen or $C_1$–$C_6$alkyl and the other is $C_1$–$C_6$alkyl, $C_1$–$C_6$alkoxy, $C_6$–$C_{10}$aryloxy, acyloxy selected from the group consisting of —O—C(=O)—H, —O—C(=O)—$C_1$–$C_{19}$alkyl, —O—C(=O)—$C_1$–$C_{54}$alkenyl, —O—C(=O)—$C_6$–$C_{10}$aryl, —O—C(=O)—$C_1$–$C_{36}$alkenyl-$C_6$–$C_{10}$aryl, —O—C(=O)—O—$C_1$–$C_6$alkyl, —O—C(=O)—O—$C_6$–$C_{10}$aryl, —O—C(=O)—NH—$C_1$–$C_6$alkyl, —O—C(=O)—NH—$C_6$–$C_{10}$aryl and —O—C(=O)—N($C_1$–$C_6$alkyl)$_2$, $C_1$–$C_6$alkylamino, di-$C_1$–$C_6$alkylamino, $C_6$–$C_{10}$arylamino, acylamino selected from the group consisting of —NH—C(=O)—H, —NH—C(=O)—$C_1$–$C_{19}$alkyl, —NH—C(=O)—$C_1$–$C_{54}$alkenyl, —NH—C(=O)—$C_6$–$C_{10}$aryl, —NH—C(=O)—$C_1$–$C_{36}$alkenyl-$C_6$–$C_{10}$aryl, —NH—C(=O)—O—$C_1$–$C_{19}$alkyl, —NH—C(=O)—O—$C_6$–$C_{10}$aryl, —NH—C(=O)—NH—$C_1$–$C_6$alkyl, —NH—C(=O)—NH—$C_6$–$C_{10}$aryl and —NH—C(=O)—N($C_1$–$C_6$alkyl)$_2$, diacylamino selected from the group consisting of —N[—C(=O)—$C_1$–$C_{19}$alkyl]$_2$, —N[—C(=O)—$C_6$–$C_{10}$aryl]$_2$, —N[—C(=O)—$C_1$–$C_6$alkylene—C(=O)—], —N[—C(=O)—$C_2$–$C_6$alkenylene-C(=O)—] and phthalimido or N-acyl-N—$C_1$–$C_6$alkylamino;

or the two radicals $R_{12}$ and $R_{13}$ are together oxo; or a compound of the formula Ib, where $R_a$ is an acyl radical selected from the group consisting of —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl and —C(=O)—N($C_1$–$C_6$alkyl)$_2$;

$R_1$–$R_4$ are each $C_1$–$C_6$alkyl;

A are substituents on the phenyl rings; and m is an integer from one to four; or a compound of the formula Ic, where $R_a$ is an acyl radical selected from the group consisting of —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl, —C(=O)—N($C_1$–$C_6$alkyl)$_2$, —P(=O)—$C_1$–$C_{19}$alkyl, —P(=O)$_2$—$C_1$–$C_{19}$alkyl, —P(=O)—$C_6$–$C_{10}$aryl, —P=O(—$C_1$–$C_{19}$alkyl)$_2$, —P=O(—$C_6$–$C_{10}$aryl)$_2$, —P(=O)—O—$C_1$–$C_6$alkyl, —P(=O)—O—$C_6$–$C_{10}$aryl, —P=O(—O—$C_1$–$C_6$alkyl)$_2$, —P=O(—O—$C_6$–$C_{10}$aryl)$_2$, —P(—O—$C_1$–$C_6$alkyl)$_2$ and —P(—O—$C_6$–$C_{10}$aryl)$_2$;

$R_b$ is hydrogen, carbamoyl, $C_1$–$C_6$alkylcarbamoyl, di-$C_1$–$C_6$alkylcarbamoyl or is as defined for $R_a$;

$R_c$ and $R_d$ are each, independently of one another, hydrogen, $C_1$–$C_{20}$alkyl or $C_6$–$C_{10}$aryl; and $R_1$–$R_3$ are each $C_1$–$C_6$alkyl or $C_6$–$C_{10}$aryl; or a compound of the formula:

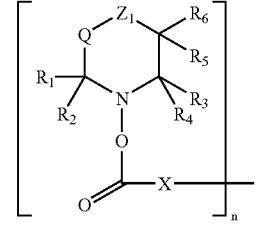

(Id)

where n is two;

X is a direct bond or the monovalent radical of a $C_1$–$C_{18}$alkylene bridge;

$R_1$–$R_4$ are each $C_1$–$C_6$alkyl;

$R_5$ and $R_6$ are each, independently of one another, hydrogen, $C_1$–$C_6$alkyl or $C_6$–$C_{10}$aryl; or $R_5$ and $R_6$ are together oxygen;

Q is a direct bond or a bivalent radical —($CR_7R_8$)— or —($CR_7R_8$—$CR_9R_{10}$)—, where $R_7$, $R_8$, $R_9$ and $R_{10}$ are each, independently of one another, hydrogen or $C_1$–$C_6$alkyl; and $Z_1$ is oxygen or a bivalent radical —$NR_{11}$— or —($CR_{12}R_{13}$)—, where $R_{11}$ is hydrogen, $C_6$–$C_{10}$aryl or $C_1$–$C_6$alkyl or, independently of one another, one of the radicals $R_{12}$ and $R_{13}$ is hydrogen or $C_1$–$C_6$alkyl and the other is $C_1$–$C_6$alkyl, $C_1$–$C_6$alkoxy, $C_6$–$C_{10}$aryloxy, acyloxy selected from the group consisting of —O—C(=O)—H, —O—C(=O)—$C_1$–$C_{19}$alkyl, —O—C(=O)—$C_1$–$C_{54}$alkenyl, —O—C(=O)—$C_6$–$C_{10}$aryl, —O—C(=O)—

$C_1$–$C_{36}$alkenyl-$C_6$–$C_{10}$aryl, —O—C(=O)—O—$C_1$–$C_6$alkyl, —O—C(=O)—O—$C_6$–$C_{10}$aryl, —O—C(=O)—NH—$C_1$–$C_6$alkyl, —O—C(=O)—NH—$C_6$–$C_{10}$aryl and —O—C(=O)—N($C_1$–$C_6$alkyl)$_2$, $C_1$–$C_6$alkylamino, di-$C_1$–$C_6$alkylamino, $C_6$–$C_{10}$arylamino, acylamino selected from the group consisting of —NH—C(=O)—H, —NH—C(=O)—$C_1$–$C_{19}$alkyl, —NH—C(=O)—$C_1$–$C_{54}$alkenyl, —NH—C(=O)—$C_6$–$C_{10}$aryl, —NH—C(=O)—$C_1$–$C_{36}$alkenyl-$C_6$–$C_{10}$aryl, —NH—C(=O)—O—$C_1$–$C_{19}$alkyl, —NH—C(=O)—O—$C_6$–$C_{10}$aryl, —NH—C(=O)—NH—$C_1$–$C_6$alkyl, —NH—C(=O)—NH—$C_6$–$C_{10}$aryl and —NH—C(=O)—N($C_1$–$C_6$alkyl)$_2$, diacylamino selected from the group consisting of —N[—C(=O)—$C_1$–$C_{19}$alkyl]$_2$, —N[—C(=O)—$C_6$–$C_{10}$aryl]$_2$, —N[—C(=O)—$C_1$–$C_6$alkylene-C(=O)—], —N[—C(=O)—$C_2$–$C_6$alkenylene-C(=O)—] and phthalimido or N-acyl-N—$C_1$–$C_6$alkylamino;

or the two radicals $R_{12}$ and $R_{13}$ are together oxo; or a compound of the formula:

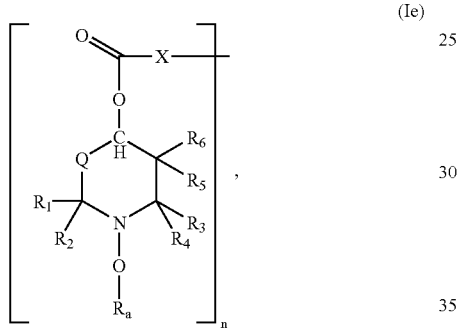

(Ie)

where n is two $R_a$ is an acyl radical selected from the group consisting of —C(=O)—H, —C(=O)—$C_1$–$C_{19}$alkyl, —C(=O)—$C_2$–$C_{19}$alkenyl, —C(=O)—$C_2$–$C_4$alkenyl-$C_6$–$C_{10}$aryl, —C(=O)—$C_6$–$C_{10}$aryl, —C(=O)—O—$C_1$–$C_6$alkyl, —C(=O)—O—$C_6$–$C_{10}$aryl, —C(=O)—NH—$C_1$–$C_6$alkyl, —C(=O)—NH—$C_6$–$C_{10}$aryl and —C(=O)—N($C_1$–$C_6$alkyl)$_2$;

X is a direct bond or the monovalent radical of a $C_1$–$C_{18}$alkylene bridge;

$R_1$–$R_4$ are each $C_1$–$C_6$alkyl;

$R_5$ and $R_6$ are each, independently of one another, hydrogen $C_1$–$C_6$alkyl or $C_6$–$C_{10}$aryl; or $R_5$ and $R_6$ are together oxygen; and Q is a direct bond or a bivalent radical —(CR$_7$R$_8$)— or —(CR$_7$R$_8$—CR$_9$R$_{10}$)—, where $R_7$, $R_8$, $R_9$ and $R_{10}$ are each, independently of one another, hydrogen or $C_1$–$C_6$alkyl.

10. A process according to claim 1, wherein the temperature is between 200° C. and 270° C.

11. A process according to claim 1, characterised in that said hydroxylamine ester is added to a blend of polypropylene with polyethylene selected from the group consisting of high density polyethylene (HDPE), high molecular weight high density polyethylene (HMW HDPE), ultra high molecular weight high density polyethylene (UHMW HDPE), medium density polyethylene (MDPE), low density polyethylene (LDPE), linear low density polyethylene (LL-DPE), branched low density polyethylene (BLDPE) and ethylene-propylene-diene terpolymers (EPDM) containing small proportions of diene.

12. A process according to claim 9, characterised in that said hydroxylamine ester is a compound of formula (Ia) in which $R_a$ is an acyl radical selected from the group consisting of —C(=O)—$C_1$–$C_{19}$alkyl, trifluoroacetyl, benzoyl, —C(=O)—O—$C_1$–$C_6$alkyl, $C_1$–$C_6$alkylcarbamoyl and phenylcarbamoyl;

$R_1$–$R_4$ are each $C_1$–$C_6$alkyl;

$R_5$ and $R_6$ are each, independently of one another, hydrogen or $C_1$–$C_6$alkyl;

Q is the bivalent radical —(CR$_7$R$_8$)—, where $R_7$ and $R_8$ are each hydrogen; and $Z_1$ is the bivalent radical —(CR$_{12}$R$_{13}$)—, where, independently of one another, one of the radicals $R_{12}$ and $R_{13}$ is hydrogen and the other is etherified or esterified hydroxy selected from the group consisting of $C_1$–$C_6$alkoxy, benzoyloxy, —O—C(=O)—$C_1$–$C_{19}$alkyl, trifluoroacetoxy, $C_1$–$C_6$alkylcarbamoyloxy and phenylcarbamoyloxy.

13. A process according to claim 3, characterised in that said hydroxylamine ester is a compound of the formula

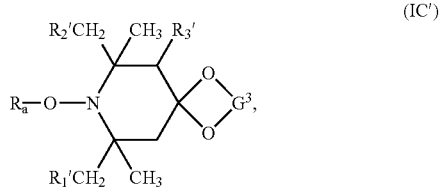

(IC')

where $R_a$, $R_1'$, $R_2'$ and $R_3'$ are as defined under the formula IA and $G^3$ is $C_2$–$C_8$alkylene or $C_4$–$C_{22}$acyloxyalkylene.

14. A process according to claim 1, wherein the polypropylene, propylene copolymers or polypropylene blends and hydroxylamine ester or polymer of a hydroxylamine ester are heated at a temperature between 160° C. and 280° C. for from about 10 seconds to 20 minutes.

15. A process according to claim 1, wherein the hydroxylamine ester or polymer of a hydroxylamine ester is added to the polypropylene, propylene copolymers or polypropylene blends at a temperature below the temperature at which degradation takes place and then susequently heated at a temperature between 160° C. and 280° C.

* * * * *